US012653535B2

(12) United States Patent
Seddon et al.

(10) Patent No.: US 12,653,535 B2
(45) Date of Patent: Jun. 16, 2026

(54) MAGNETIC ANASTOMOSIS DEVICES WITH VARYING MAGNETIC FORCE AT A DISTANCE

(71) Applicant: G.I. Windows, Inc., Westwood, MA (US)

(72) Inventors: Dane T. Seddon, Boston, MA (US); Peter F. Sugar, Charlestown, MA (US)

(73) Assignee: G.I. Windows, Inc., Canton, MA (US)

( * ) Notice: Subject to any disclaimer, the term of this patent is extended or adjusted under 35 U.S.C. 154(b) by 164 days.

(21) Appl. No.: 18/538,901

(22) Filed: Dec. 13, 2023

(65) Prior Publication Data

US 2024/0215981 A1 Jul. 4, 2024

Related U.S. Application Data

(63) Continuation of application No. PCT/US2022/025432, filed on Apr. 19, 2022.

(60) Provisional application No. 63/211,130, filed on Jun. 16, 2021.

(51) Int. Cl.
| | |
|---|---|
| *A61B 17/11* | (2006.01) |
| *A61B 17/00* | (2006.01) |

(52) U.S. Cl.
CPC .... *A61B 17/1114* (2013.01); *A61B 17/00234* (2013.01); *A61B 2017/00818* (2013.01); *A61B 2017/00876* (2013.01); *A61B 2017/1139* (2013.01)

(58) Field of Classification Search
CPC .............. A61B 1/018; A61B 17/00234; A61B 17/0218; A61B 17/0485; A61B 17/06166; A61B 17/1114; A61B 17/320016; A61B 18/082; A61B 18/1492; A61B 2017/0034; A61B 2017/00349; A61B 2017/00477; A61B 2017/00818; A61B 2017/00876; A61B 2017/00986; A61B 2017/0619; A61B 2017/0649; A61B 2017/1139; A61B 2017/22069; A61B 2018/141;

(Continued)

(56) References Cited

U.S. PATENT DOCUMENTS

| | | | |
|---|---|---|---|
| 4,197,840 | A | 4/1980 | Beck et al. |
| 4,538,130 | A | 8/1985 | Gluckstern et al. |
| 5,300,910 | A | 4/1994 | Unkelbach et al. |

(Continued)

FOREIGN PATENT DOCUMENTS

| | | |
|---|---|---|
| CN | 105011985 A | 11/2015 |
| CN | 205379345 U | 7/2016 |

(Continued)

OTHER PUBLICATIONS

Author Unknown, "An Innovative Implant for the Creation of Anastomosis," PLIO, retrieved from the internet at: https://pliosurgical. com/, Jan. 19, 2024 (13 pages).

(Continued)

*Primary Examiner* — Mohamed G Gabr
(74) *Attorney, Agent, or Firm* — Nutter McClennen & Fish LLP

(57) ABSTRACT

The invention provides systems, devices, and methods for the delivery, deployment, and positioning of magnetic compression devices at a desired site so as to improve the accuracy of anastomoses creation between tissues, organs, or the like.

20 Claims, 80 Drawing Sheets

(58) Field of Classification Search
CPC .... A61B 2018/1425; A61B 2018/1427; A61B
2090/037; A61B 2090/378
See application file for complete search history.

(56) References Cited

U.S. PATENT DOCUMENTS

| | | | |
|---|---|---|---|
| 5,320,629 | A | 6/1994 | Noda et al. |
| 5,381,784 | A | 1/1995 | Adair |
| 5,431,670 | A | 7/1995 | Holmes |
| 5,595,562 | A | 1/1997 | Grier |
| 5,690,656 | A | 11/1997 | Cope et al. |
| 6,129,668 | A | 10/2000 | Haynor et al. |
| 6,132,458 | A | 10/2000 | Staehle et al. |
| 6,190,303 | B1 | 2/2001 | Glenn et al. |
| 6,273,895 | B1 | 8/2001 | Pinchuk et al. |
| 6,352,543 | B1 | 3/2002 | Cole |
| 6,371,964 | B1 | 4/2002 | Vargas et al. |
| 6,478,210 | B2 | 11/2002 | Adams et al. |
| 6,537,284 | B1 | 3/2003 | Inoue |
| 6,632,229 | B1 | 10/2003 | Yamanouchi et al. |
| 6,652,540 | B1 | 11/2003 | Cole et al. |
| 6,699,263 | B2 | 3/2004 | Cope |
| 6,719,768 | B1 | 4/2004 | Cole et al. |
| 6,802,847 | B1 | 10/2004 | Carson et al. |
| 6,827,718 | B2 | 12/2004 | Hutchins et al. |
| 6,932,827 | B2 | 8/2005 | Cole |
| 7,282,057 | B2 | 10/2007 | Surti et al. |
| 7,618,427 | B2 | 11/2009 | Oritz et al. |
| 7,641,638 | B2 | 1/2010 | Waxman et al. |
| 7,760,059 | B2 | 7/2010 | Higuchi |
| 7,909,837 | B2 | 3/2011 | Crews et al. |
| 8,043,290 | B2 | 10/2011 | Harrison et al. |
| 8,118,821 | B2 | 2/2012 | Mouw |
| 8,142,454 | B2 | 3/2012 | Harrison et al. |
| 8,262,680 | B2 | 9/2012 | Swain et al. |
| 8,439,915 | B2 | 5/2013 | Harrison et al. |
| 8,506,516 | B2 | 8/2013 | Kassab et al. |
| 8,518,062 | B2 | 8/2013 | Cole et al. |
| 8,556,919 | B2 | 10/2013 | Aguirre et al. |
| 8,603,121 | B2 | 12/2013 | Surti et al. |
| 8,623,036 | B2 | 1/2014 | Harrison et al. |
| 8,679,139 | B2 | 3/2014 | Aguirre et al. |
| 8,685,046 | B2 | 4/2014 | Viola |
| 8,728,105 | B2 | 5/2014 | Aguirre |
| 8,794,243 | B2 | 8/2014 | Deem et al. |
| 8,828,031 | B2 | 9/2014 | Fox et al. |
| 8,828,032 | B2 | 9/2014 | McWeeney et al. |
| 8,845,663 | B2 | 9/2014 | Chmura |
| 8,864,781 | B2 | 10/2014 | Surti et al. |
| 8,870,899 | B2 | 10/2014 | Beisel et al. |
| 8,915,915 | B2 | 12/2014 | Harrison et al. |
| 9,168,041 | B2 | 10/2015 | Zaritsky et al. |
| 9,226,753 | B2 | 1/2016 | Surti et al. |
| 9,320,524 | B2 | 4/2016 | Gagner et al. |
| 9,421,015 | B2 | 8/2016 | Gagner et al. |
| 9,456,820 | B2 | 10/2016 | Gagner et al. |
| 9,492,173 | B2 | 11/2016 | McWeeney et al. |
| 9,539,010 | B2 | 1/2017 | Gagner et al. |
| 9,763,664 | B2 | 9/2017 | Beisel et al. |
| 9,801,635 | B2 | 10/2017 | Gagner et al. |
| 9,877,724 | B2 | 1/2018 | Gagner et al. |
| 9,943,335 | B2 | 4/2018 | Gittard et al. |
| 10,039,550 | B2 | 8/2018 | Altman |
| 10,159,487 | B2 | 12/2018 | Gagner et al. |
| 10,182,821 | B2 | 1/2019 | Lukin et al. |
| 10,285,703 | B2 | 5/2019 | Viola |
| 10,342,544 | B2 | 7/2019 | Bakos et al. |
| 10,376,400 | B2 | 8/2019 | McGuckin, Jr. |
| 10,448,954 | B2 | 10/2019 | McWeeney et al. |
| 10,517,600 | B2 | 12/2019 | Beisel et al. |
| 10,555,735 | B2 | 2/2020 | Bakos et al. |
| 10,568,630 | B2 | 2/2020 | Hernandez et al. |
| 10,595,869 | B2 | 3/2020 | Beisel et al. |
| 10,624,643 | B2 | 4/2020 | Hunt et al. |
| 10,624,644 | B2 | 4/2020 | Bakos et al. |
| 10,631,865 | B2 | 4/2020 | Bakos et al. |
| 10,667,817 | B2 | 6/2020 | Gagner et al. |
| 10,682,143 | B2 | 6/2020 | Hernandez et al. |
| 10,779,831 | B2 | 9/2020 | Lukin et al. |
| 10,813,642 | B2 | 10/2020 | Beisel et al. |
| 10,952,732 | B2 | 3/2021 | Binmoeller et al. |
| 11,039,838 | B2 | 6/2021 | Binmoeller et al. |
| 11,311,298 | B2 | 4/2022 | Gagner et al. |
| 11,432,873 | B2 | 9/2022 | Brown et al. |
| 2002/0055674 | A1 | 5/2002 | Ben-Haim et al. |
| 2002/0143347 | A1 | 10/2002 | Cole et al. |
| 2003/0149422 | A1 | 8/2003 | Muller |
| 2003/0176767 | A1 | 9/2003 | Long et al. |
| 2004/0034377 | A1 | 2/2004 | Sharkawy et al. |
| 2004/0059280 | A1 | 3/2004 | Makower et al. |
| 2005/0020958 | A1 | 1/2005 | Paolini et al. |
| 2005/0080439 | A1 | 4/2005 | Carson et al. |
| 2005/0256503 | A1 | 11/2005 | Hall |
| 2005/0277966 | A1 | 12/2005 | Ewers et al. |
| 2005/0283235 | A1 | 12/2005 | Kugler et al. |
| 2006/0036267 | A1 | 2/2006 | Saadat et al. |
| 2006/0271107 | A1 | 11/2006 | Harrison et al. |
| 2006/0282106 | A1 | 12/2006 | Cole et al. |
| 2007/0106312 | A1 | 5/2007 | Vargas et al. |
| 2007/0276378 | A1 | 11/2007 | Harrison et al. |
| 2008/0051626 | A1 | 2/2008 | Sato et al. |
| 2008/0086192 | A1 | 4/2008 | WasDyke et al. |
| 2008/0114384 | A1 | 5/2008 | Chang et al. |
| 2008/0183272 | A1 | 7/2008 | Wood et al. |
| 2008/0200933 | A1 | 8/2008 | Bakos et al. |
| 2008/0200934 | A1 | 8/2008 | Fox |
| 2008/0208105 | A1 | 8/2008 | Zelickson et al. |
| 2008/0208224 | A1 | 8/2008 | Surti et al. |
| 2008/0243225 | A1 | 10/2008 | Satasiya et al. |
| 2008/0262523 | A1 | 10/2008 | Makower et al. |
| 2009/0048618 | A1 | 2/2009 | Harrison et al. |
| 2009/0062824 | A1 | 3/2009 | Berg et al. |
| 2009/0125042 | A1 | 5/2009 | Mouw |
| 2009/0227828 | A1 | 9/2009 | Swain et al. |
| 2010/0010508 | A1 | 1/2010 | Takahashi et al. |
| 2010/0010610 | A1 | 1/2010 | Grevious |
| 2010/0036399 | A1 | 2/2010 | Viola |
| 2010/0056861 | A1 | 3/2010 | Spivey |
| 2010/0099947 | A1 | 4/2010 | Sato et al. |
| 2010/0179510 | A1 | 7/2010 | Fox et al. |
| 2011/0009886 | A1 | 1/2011 | Gagner et al. |
| 2011/0098731 | A1 | 4/2011 | Whitbrook et al. |
| 2011/0118765 | A1 | 5/2011 | Aguirre |
| 2011/0144560 | A1 | 6/2011 | Gagner et al. |
| 2011/0160751 | A1 | 6/2011 | Granja Filho |
| 2011/0160752 | A1 | 6/2011 | Aguirre |
| 2011/0295055 | A1 | 12/2011 | Albrecht et al. |
| 2011/0295285 | A1 | 12/2011 | Mcweeney et al. |
| 2012/0022572 | A1 | 1/2012 | Braun et al. |
| 2012/0197062 | A1 | 8/2012 | Requarth |
| 2012/0238796 | A1 | 9/2012 | Conlon |
| 2012/0259350 | A1 | 10/2012 | Gagner et al. |
| 2012/0330330 | A1 | 12/2012 | Gagner et al. |
| 2013/0138126 | A1 | 5/2013 | Gagner et al. |
| 2013/0150873 | A1 | 6/2013 | Gagner et al. |
| 2013/0253548 | A1 | 9/2013 | Harrison et al. |
| 2013/0253550 | A1 | 9/2013 | Beisel et al. |
| 2013/0325042 | A1 | 12/2013 | Fabian et al. |
| 2014/0018824 | A1 | 1/2014 | Julian et al. |
| 2014/0019468 | A1 | 1/2014 | Federoff et al. |
| 2014/0066709 | A1 | 3/2014 | Mirza et al. |
| 2014/0188246 | A1 | 7/2014 | Aronson et al. |
| 2014/0194689 | A1 | 7/2014 | Carrillo, Jr. et al. |
| 2014/0236064 | A1 | 8/2014 | Binmoeller et al. |
| 2014/0243592 | A1 | 8/2014 | Kato et al. |
| 2014/0277342 | A1 | 9/2014 | Roeder et al. |
| 2014/0303657 | A1 | 10/2014 | Kim et al. |
| 2014/0309669 | A1 | 10/2014 | Fabian et al. |
| 2014/0309670 | A1 | 10/2014 | Bakos et al. |
| 2014/0343583 | A1 | 11/2014 | McWeeney et al. |
| 2014/0379065 | A1 | 12/2014 | Johnson et al. |
| 2015/0057687 | A1 | 2/2015 | Gittard et al. |
| 2015/0164508 | A1 | 6/2015 | Hernandez et al. |
| 2015/0182224 | A1 | 7/2015 | Altman |

(56) References Cited

U.S. PATENT DOCUMENTS

| | | |
|---|---|---|
| 2016/0022266 A1 | 1/2016 | Lukin et al. |
| 2016/0235442 A1 | 8/2016 | Palese et al. |
| 2016/0262761 A1* | 9/2016 | Beisel ................. A61B 17/1114 |
| 2016/0287257 A1 | 10/2016 | Fabian et al. |
| 2016/0324523 A1 | 11/2016 | Lukin et al. |
| 2016/0367236 A1 | 12/2016 | Leeflang et al. |
| 2016/0374683 A1 | 12/2016 | Gagner et al. |
| 2017/0035425 A1 | 2/2017 | Fegelman et al. |
| 2017/0265866 A1 | 9/2017 | Ryou et al. |
| 2018/0028186 A1 | 2/2018 | Yamanouchi |
| 2018/0028187 A1 | 2/2018 | Gagner et al. |
| 2018/0193061 A1 | 7/2018 | Gittard et al. |
| 2018/0214149 A1 | 8/2018 | Hunt et al. |
| 2018/0214150 A1 | 8/2018 | Bakos et al. |
| 2018/0214152 A1 | 8/2018 | Bakos et al. |
| 2018/0263625 A1 | 9/2018 | Lukin et al. |
| 2018/0296218 A1 | 10/2018 | Binmoeller et al. |
| 2018/0361127 A1 | 12/2018 | Gray et al. |
| 2019/0133587 A1 | 5/2019 | Gagner et al. |
| 2019/0133678 A1 | 5/2019 | Pate et al. |
| 2019/0183507 A1 | 6/2019 | Baillargeon |
| 2019/0216460 A1 | 7/2019 | Kopelman |
| 2019/0261998 A1 | 8/2019 | Altman et al. |
| 2019/0274687 A1* | 9/2019 | Wang ................. A61B 17/1114 |
| 2020/0008834 A1 | 1/2020 | Cauche et al. |
| 2020/0129283 A1 | 4/2020 | Swensgard et al. |
| 2020/0138438 A1 | 5/2020 | Harrison et al. |
| 2020/0170776 A1 | 6/2020 | Folan |
| 2020/0187947 A1 | 6/2020 | Hernandez et al. |
| 2020/0222049 A1 | 7/2020 | McWeeney et al. |
| 2020/0229968 A1 | 7/2020 | Galloway |
| 2020/0246009 A1 | 8/2020 | Gagner et al. |
| 2020/0323530 A1 | 10/2020 | Sharma |
| 2021/0100554 A1 | 4/2021 | Seddon et al. |
| 2021/0161532 A1 | 6/2021 | Beisel et al. |
| 2021/0169485 A1 | 6/2021 | Beisel et al. |
| 2021/0169486 A1 | 6/2021 | Gagner et al. |
| 2021/0244414 A1 | 8/2021 | Lukin et al. |
| 2022/0087678 A1 | 3/2022 | Gagner et al. |
| 2022/0104956 A1 | 4/2022 | Pham et al. |
| 2022/0257252 A1 | 8/2022 | Todd et al. |
| 2023/0165585 A1 | 6/2023 | McWeeney et al. |
| 2023/0172608 A1 | 6/2023 | Lukin et al. |
| 2023/0190269 A1 | 6/2023 | Tinkham et al. |
| 2023/0255624 A1 | 8/2023 | Wallace et al. |
| 2023/0389923 A1 | 12/2023 | Tinkham et al. |
| 2023/0389924 A1 | 12/2023 | Seddon et al. |
| 2024/0041460 A1 | 2/2024 | Seddon |
| 2024/0041461 A1 | 2/2024 | Tinkham et al. |
| 2024/0065694 A1 | 2/2024 | Seddon |
| 2024/0074751 A1 | 3/2024 | Tinkham et al. |
| 2024/0074755 A1 | 3/2024 | Mann et al. |
| 2024/0074759 A1 | 3/2024 | Sugar et al. |

FOREIGN PATENT DOCUMENTS

| | | |
|---|---|---|
| DE | 3011742 A1 | 10/1981 |
| EP | 1894514 A2 | 3/2008 |
| EP | 1493391 B1 | 12/2009 |
| EP | 2207488 B1 | 9/2012 |
| EP | 2538852 A1 | 1/2013 |
| EP | 3267905 A1 | 1/2018 |
| EP | 2260752 B1 | 3/2018 |
| EP | 3573542 A1 | 12/2019 |
| EP | 3487418 A4 | 4/2020 |
| EP | 4115949 A1 | 1/2023 |
| JP | 2003530916 A | 10/2003 |
| JP | 2006271832 A | 10/2006 |
| JP | 2008508939 A | 3/2008 |
| JP | 2011500159 A | 1/2011 |
| JP | 2015139592 A | 8/2015 |
| JP | 2017/521223 A | 8/2017 |
| JP | 202198077 A | 7/2021 |
| KR | 20150102567 A | 9/2015 |
| RU | 2018266 C1 | 8/1994 |
| SU | 1708313 A1 | 1/1992 |
| SU | 1725851 A1 | 4/1992 |
| WO | 01/087398 A2 | 11/2001 |
| WO | 01/93920 A2 | 12/2001 |
| WO | 2009048954 A1 | 4/2009 |
| WO | 2011085006 A2 | 7/2011 |
| WO | 2011/103400 A1 | 8/2011 |
| WO | 2013009886 A1 | 1/2013 |
| WO | 2013/176993 A1 | 11/2013 |
| WO | 2014055193 A1 | 4/2014 |
| WO | 2016082481 A1 | 6/2016 |
| WO | 2016/145414 A1 | 9/2016 |
| WO | 2018022180 A1 | 2/2018 |
| WO | 2018/138632 A1 | 8/2018 |
| WO | 2019077218 A1 | 4/2019 |
| WO | 2019232526 A1 | 12/2019 |
| WO | 2019232527 A1 | 12/2019 |
| WO | 2020/196336 A1 | 10/2020 |
| WO | 2021/203910 A1 | 10/2021 |
| WO | 2021/207821 A1 | 10/2021 |
| WO | 2022/061117 A1 | 3/2022 |
| WO | 2022/132351 A1 | 6/2022 |
| WO | 2022/171349 A1 | 8/2022 |

OTHER PUBLICATIONS

European Patent Office, Communication pursuant to Article 94(3) EPC for Application No. 19810895.3, dated Feb. 13, 2023 (3 pages).

Extended European Search Report of the European Patent Office, Application No. 19810895.3, dated Feb. 7, 2022, 10 pages.

Gagner, M., "Duodeno-Ileal Anastomosis with Self-Assembling Magnets: Initial Concepts and Basis of This Operation", Obesity Surgery 32, 932-933 (2022).

International Search Report and Written Opinion issued for Application No. PCT/US2016/031547 dated Oct. 18, 2016, 18 pages.

International Search Report and Written Opinion of the International Searching Authority, Application No. PCT/US2019035202, mailed Aug. 8, 2019, 6 pages.

International Search Report and Written Opinion of the International Searching Authority, Application No. PCT/US2022/25343, mailed Jul. 18, 2022, 14 pages.

International Search Report and Written Opinion of the International Searching Authority, Application No. PCT/US2022/25353, mailed Jun. 30, 2022, 12 pages.

International Search Report and Written Opinion of the International Searching Authority, for Application No. PCT/US2011/020229, with a date of mailing of Jun. 21, 2013, 6 pages.

International Search Report and Written Opinion of the International Searching Authority, for Application No. PCT/US2013/041641, dated Oct. 18, 2013, 4 pages.

International Search Report and Written Opinion of the International Searching Authority, for Application No. PCT/US2015/041498 dated Nov. 17, 2015, 17 pages.

International Search Report and Written Opinion of the International Searching Authority, for Application PCT/US2016/022209, dated May 30, 2016.

International Search Report and Written Opinion of the International Searching Authority, for Application PCT/US22/25338, dated Aug. 19, 2022, 14 pages.

International Search Report and Written Opinion of the International Searching Authority, for Application PCT/US23/29416, dated Dec. 7, 2023, 9 pages.

International Search Report and Written Opinion of the International Searching Authority, for Application PCT/US23/29432, dated Nov. 14, 2023, 7 pages.

Invitation to Pay Additional Fees and, Where Applicable, Protest Fee, from the International Search Authority, Application No. PCT/US2022/025338, mailed Jun. 23, 2022, 2 pages.

Invitation to Pay Additional Fees and, Where Applicable, Protest Fee, from the International Search Authority, Application No. PCT/US2022/025370, mailed Jun. 24, 2022, 3 pages.

Japanese Office Action for Japanese Patent Application No. 2021-034336 dated Dec. 17, 2021, 3 pages.

(56)         References Cited

OTHER PUBLICATIONS

Japanese Office Action, Notice of Reasons for Refusal, Japanese Patent Application No. 2020-567134 dated Feb. 21, 2023.

Japanese Penultimate Office Action for Japanese Patent Application No. 2021-034336 dated Aug. 1, 2022, 9 pages.

Japanese Search Report, Japanese Application No. 2020-567134, dated Feb. 13, 2023, 28 pages.

Supplementary Partial European Search Report for Application No. EP 13793804.9 dated Jan. 15, 2016, 9 pages.

International Search Report and Written Opinion of the International Searching Authority, for Application PCT/2023/031863, dated Jan. 22, 2024, 8 pages.

International Search Report and Written Opinion of the International Searching Authority, for Application PCT/US2023/031861, dated Feb. 2, 2024, 9 pages.

International Search Report and Written Opinion of the International Searching Authority, for Application PCT/US2023/035976, dated Feb. 2, 2024, 11 pages.

Jamshidi, et al., "Magnamosis: magnetic compression anastomosis with comparison to suture and staple techniques," Journal of Pediatric Surgery, vol. 4, Issue 1, pp. 222-228. Jan. 20, 2009 (Jan. 20, 2009). [Retrieved on May 12, 2023]. Retrieved from the Internet: <URL: https://dotorg/10.1016/j.jpedsurg.2008.10.044>. entire document.

* cited by examiner

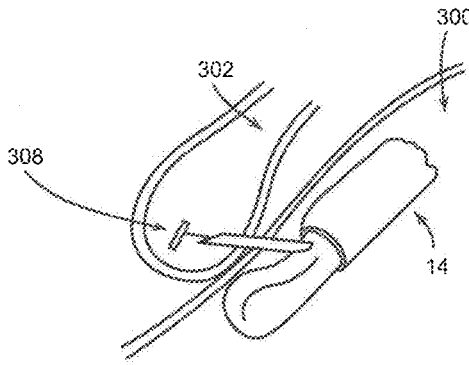
FIG. 25A
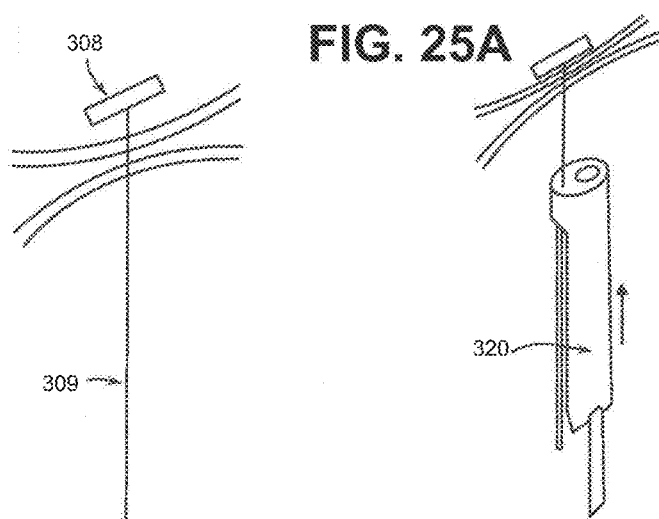
FIG. 25B FIG. 25C

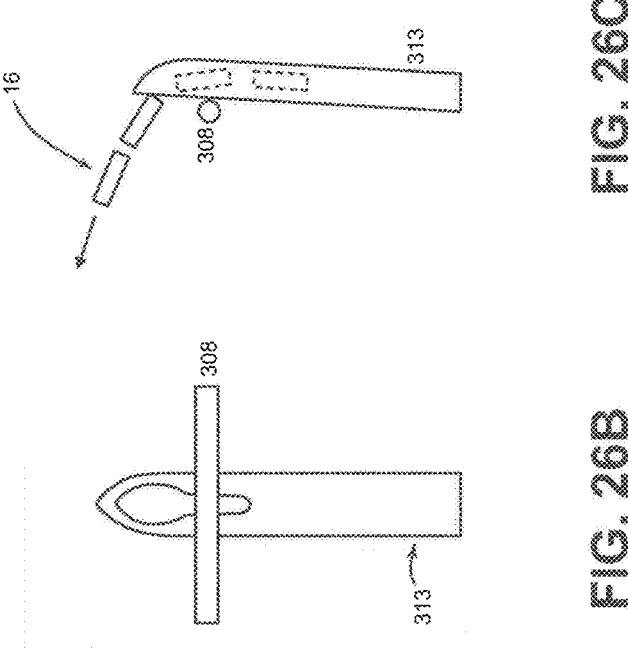
FIG. 26C
FIG. 26B
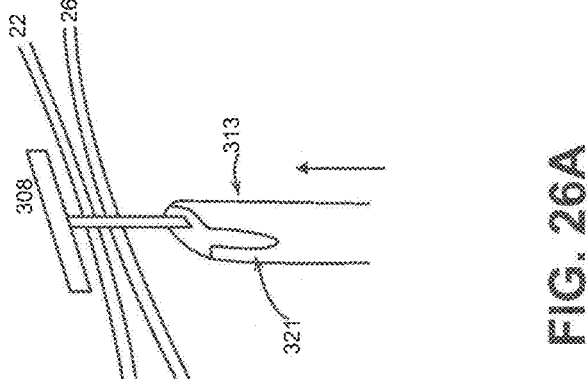
FIG. 26A

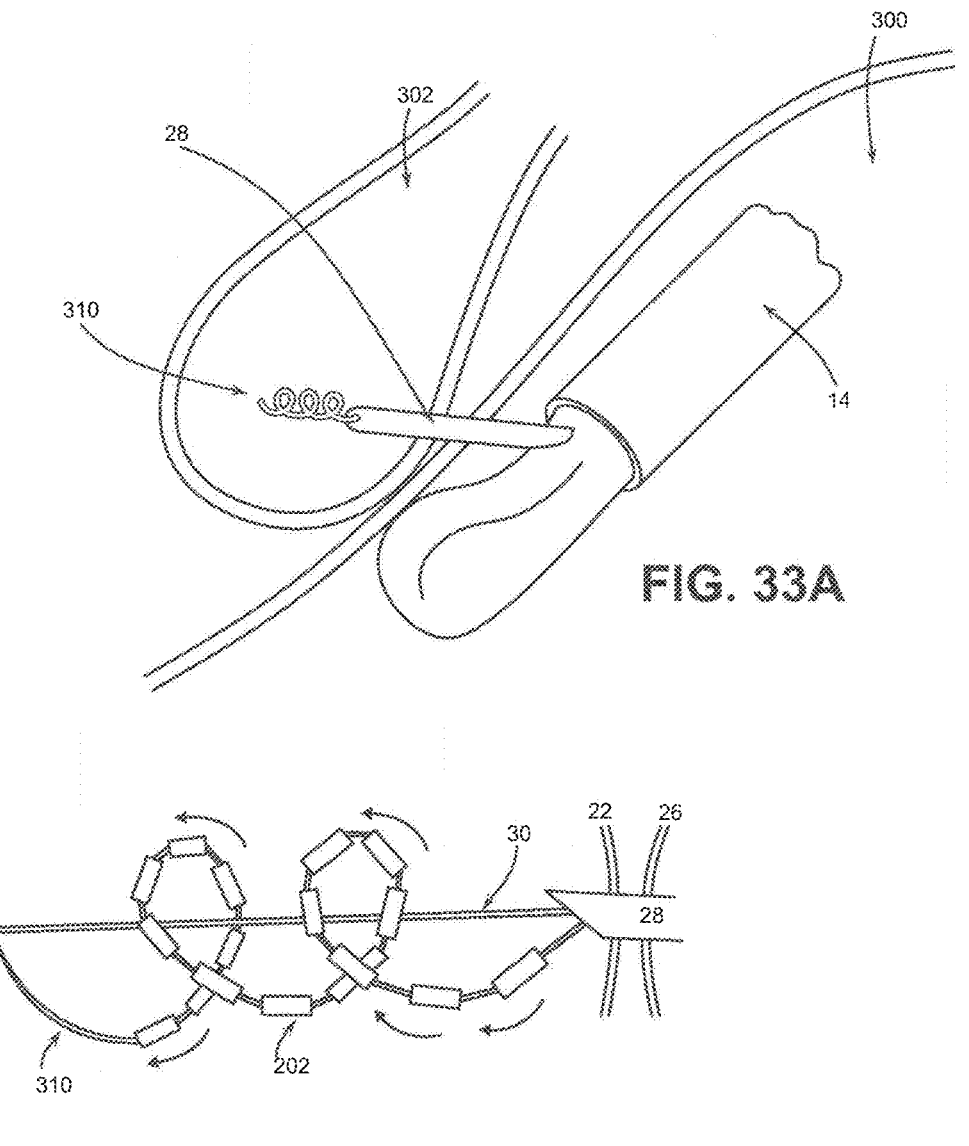
FIG. 33A
FIG. 33B
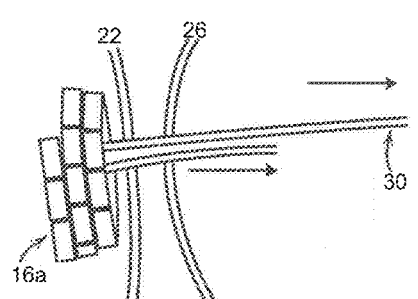
FIG. 33C

FIG. 45

Flexible Endoscopes General Diameter Guide for Endoscopy Brushes

| SCOPE TYPE | INSERTION TUBE OUTER DIAMETER | WORKING LENGTH | INSTRUMENT CHANNEL INTERNAL DIAMETER | HEALTHMARK ENDO BRUSHES | ENDOBRUSH DIAMETER RANGE | OLYMPUS COLOR GUIDE |
|---|---|---|---|---|---|---|
| ADULTS | | | | | | |
| GASTROSCOPE | 9.0 mm - 11.4 mm | 1030 mm - 1050 mm | 2.8mm - 3.8mm | CC-250, CC-374 | 2.6 - 3.2 mm, 3.7 - 4.3 mm | |
| DUODENSCOPE | 10.8 mm - 12.5 mm | 1235 mm - 1250 mm | 3.2mm - 4.2mm | CC-250, CC374 | 2.6 - 3.2 mm, 3.7 - 4.3 mm | |
| COLONOSCOPE | 12.9 mm - 13.7 mm | 1330 mm - 1680 mm | 3.7mm - 4.2mm | CC-374 | 3.7 - 4.3 mm | |
| SIGMOIDOSCOPE | 12.8 mm - 13.2 mm | 700 mm - 730 mm | 3.7mm - 4.2mm | CC-374 | 3.7 - 4.3 mm | |
| ENTEROSCOPE | 10.5 mm - 11.7 mm | 2200 mm - 2500 mm | 2.8mm - 3.8mm | CC-250, CC-374 | 2.6 - 3.2 mm, 3.7 - 4.3 mm | |
| BRONCHOSCOPE | 5.7 mm - 6.0 mm | 550 mm - 600 mm | 2.0mm - 2.8mm | CC-172, CC-250 | 1.7 - 2.2 mm, 2.6 - 3.2 mm | |
| URETEROSCOPE | 2.8 mm - 3.3 mm | 670 mm - 700 mm | 1.2mm | CC-172 | 1.7 - 2.2 mm | |
| CYSTOSCOPE | 5.4 mm - 5.5 mm | 380 mm | 2.2mm - 2.4mm | CC-172, CC-250 | 1.7 - 2.2 mm, 2.6 - 3.2 mm | |
| RHINO-LARYNGOSCOPE | 2.6 mm - 4.9 mm | 300 mm - 365 mm | N/A - 2.0 | CC-172 | 1.7 - 2.2 mm | |
| LAPARO-THORACOSCOPE | 7.0 mm | 270 mm | 2.8 mm | CC-250 | 2.6 - 3.2 mm | |
| MOBILE AIRWAY SCOPE | 4.1 mm - 5.2 mm | 600 mm | 1.5 mm - 2.6 mm | CC-172, CC-250 | 1.7 - 2.2 mm, 2.6 - 3.2 mm | |
| CHOLEDOCHOSCOPE | 2.8 mm - 5.2 mm | 380 mm - 700 mm | 1.2 mm - 2.2 mm | CC-110, CC-172 | 1.2 mm, 1.7 - 2.2 mm | white |
| PEDIATRICS | | | | | | |
| GASTROSCOPE | 5.9 mm - 6.0 mm | 1030 mm - 1050 mm | 2.0 mm | CC-172 | 1.7 - 2.2 mm | |
| COLONOSCOPE | 11.5 mm - 11.6mm | 1680 mm - 1700 mm | 3.2 mm - 3.8 mm | CC-250, CC-374 | 2.6-3.2mm, 3.7 - 4.3 mm | |
| BRONCHOSCOPE | 4.4 mm - 5.1 mm | 600 mm | 2.0 mm | CC-172 | 1.7 - 2.2 mm | |

Figure 52B:
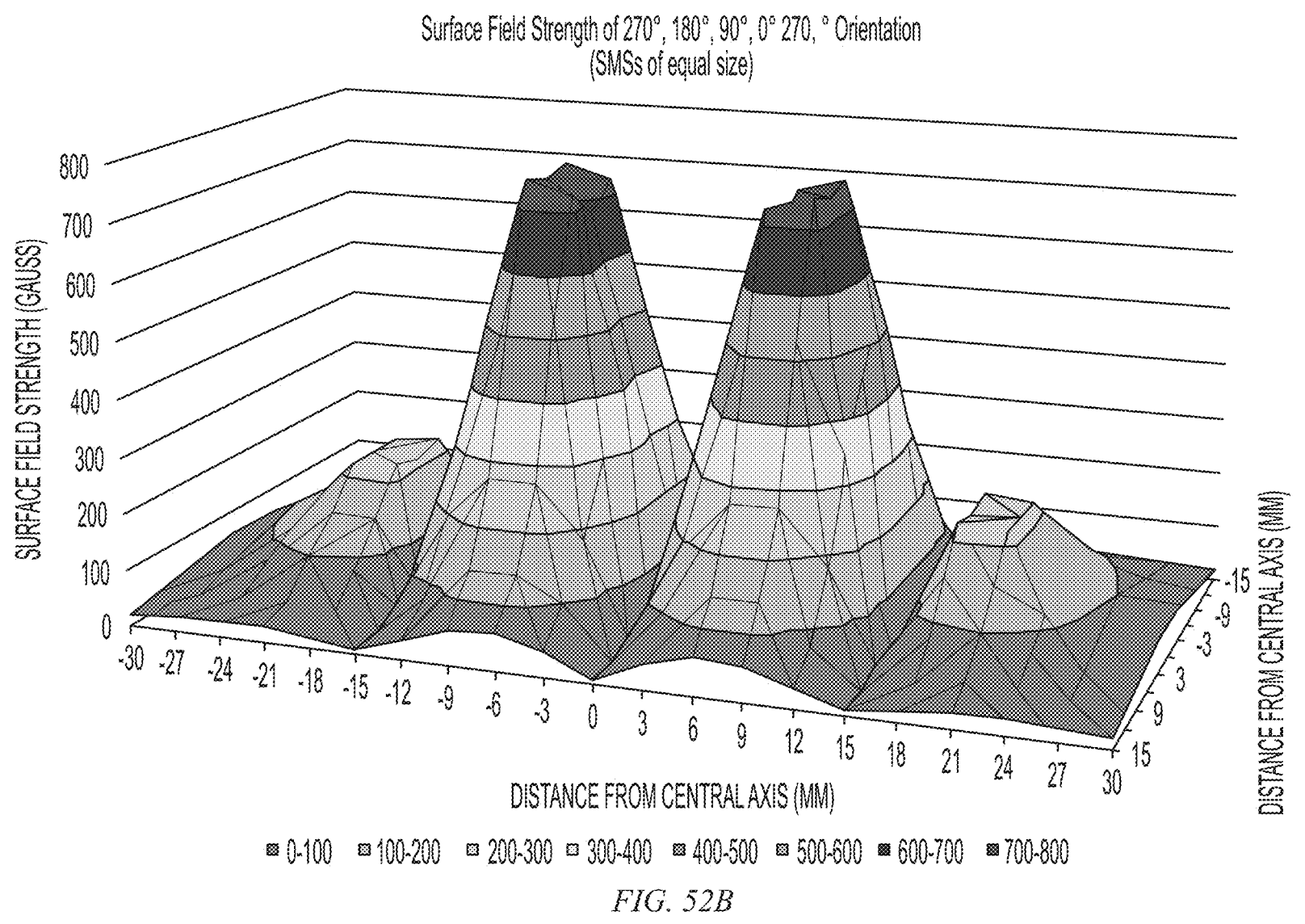

Surface Field Strength of 270°, 180°, 90°, 0° 270, ° Orientation (SMSs of equal size)

DISTANCE FROM CENTRAL AXIS (MM)

SURFACE FIELD STRENGTH (GAUSS)

DISTANCE FROM CENTRAL AXIS (MM)

Figure 52C:
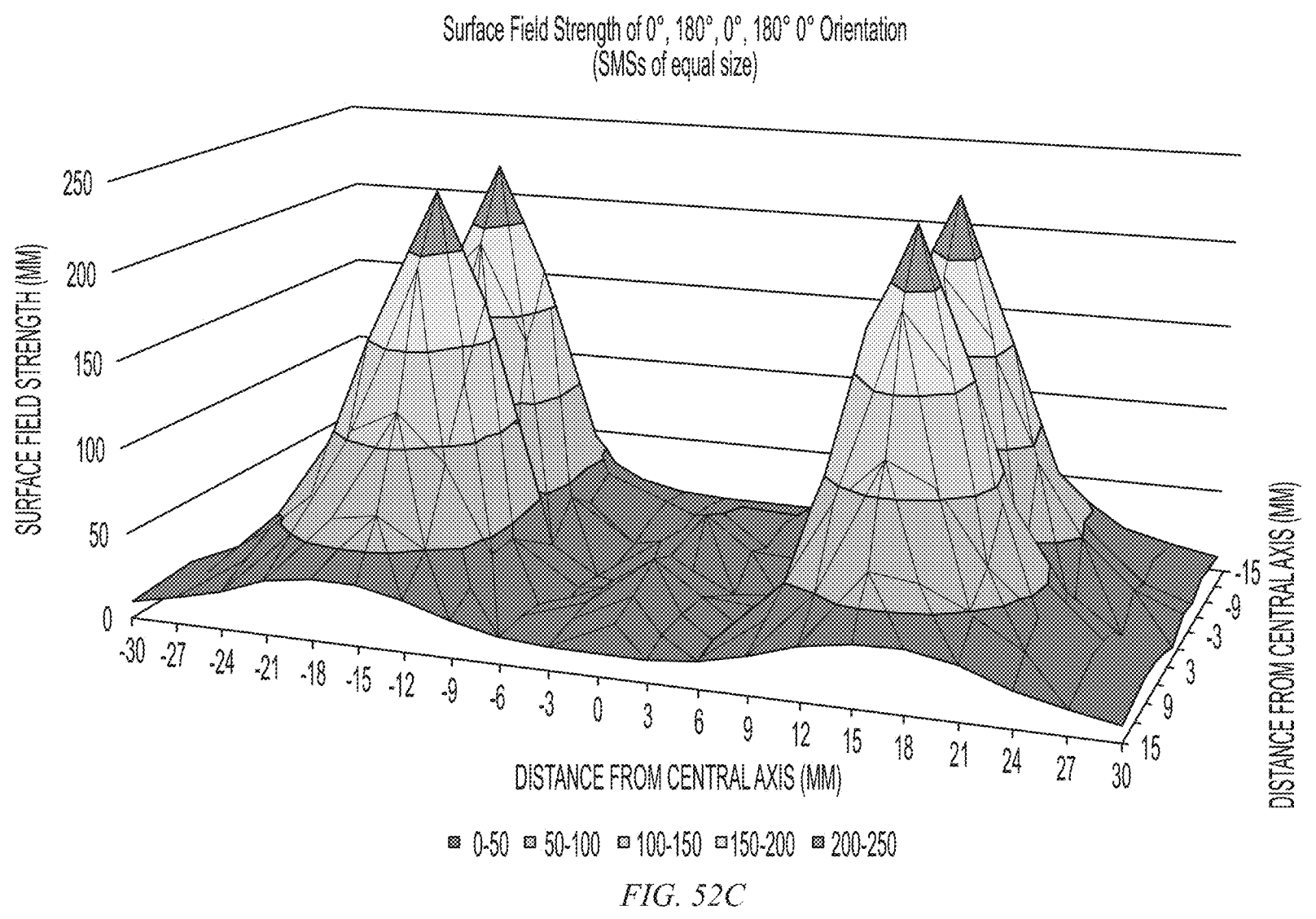

Surface Field Strength of 0°, 180°, 0°, 180° 0° Orientation (SMSs of equal size)

DISTANCE FROM CENTRAL AXIS (MM)

DISTANCE FROM CENTRAL AXIS (MM)

SURFACE FIELD STRENGTH (MM)

Figure 52D:
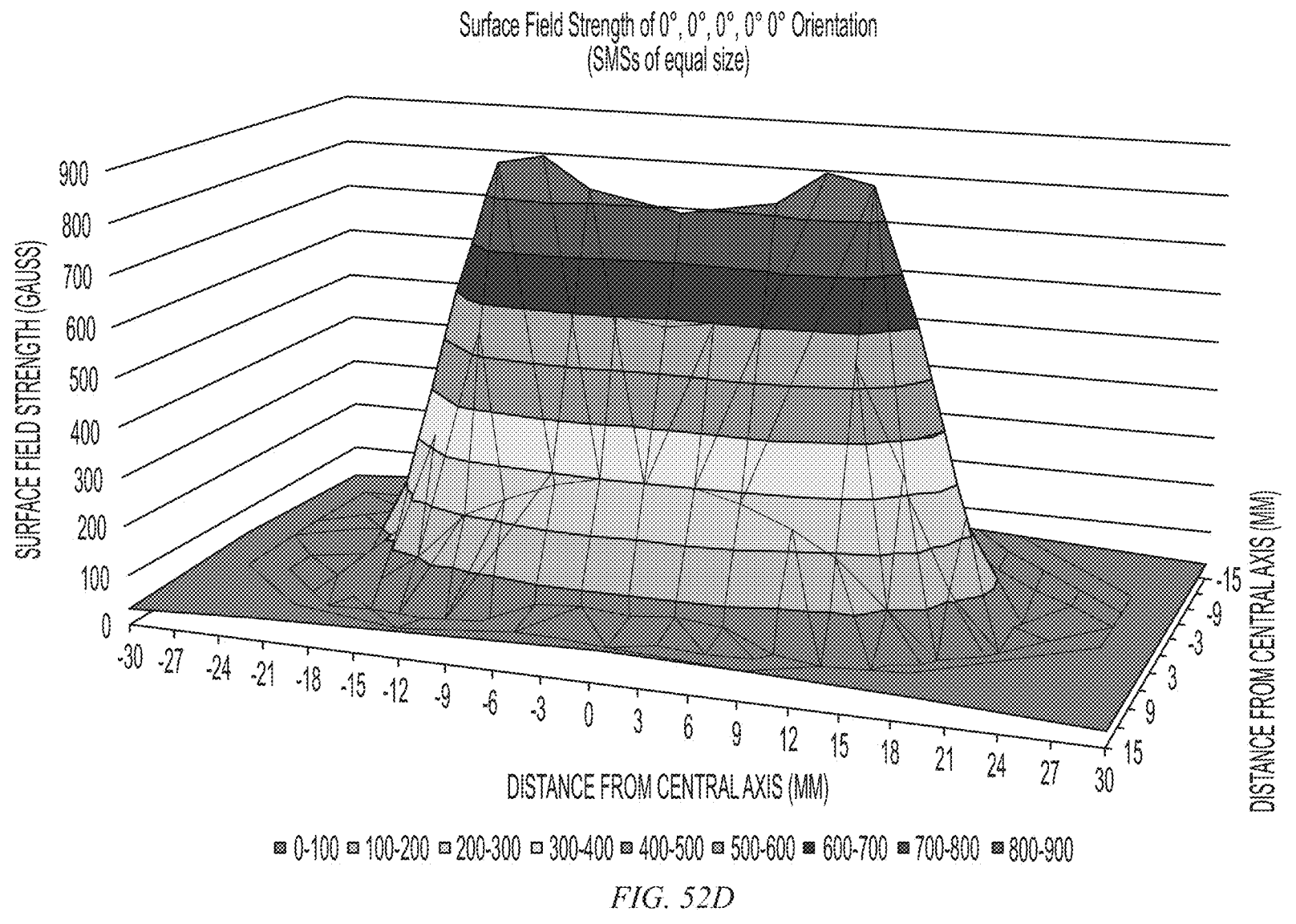

Surface Field Strength of 0°, 0°, 0°, 0° Orientation
(SMSs of equal size)

DISTANCE FROM CENTRAL AXIS (MM)

SURFACE FIELD STRENGTH (GAUSS)

DISTANCE FROM CENTRAL AXIS (MM)

MAGNETIC ANASTOMOSIS DEVICES WITH VARYING MAGNETIC FORCE AT A DISTANCE

CROSS-REFERENCE TO RELATED APPLICATIONS

This application is a continuation of International Application No. PCT/US2022/025432 filed Apr. 19, 2022, which claims the benefit of U.S. Provisional Application Ser. No. 63/211,130 entitled Magnetic Anastomosis Devices with Varying Magnetic Force at a Distance having a filing date of Jun. 16, 2021, each of which is hereby incorporated by reference herein in its entirety.

The subject matter of this patent application may be related to the subject matter of U.S. patent application Ser. No. 17/108,840 entitled SYSTEMS, DEVICES, AND METHODS FOR FORMING ANASTOMOSES filed Dec. 1, 2020 issued Sep. 12, 2023 as U.S. Pat. No. 11,751,877, which is a continuation-in-part of, and therefore claims priority from, International Patent Application No. PCT/US2019/035202 having an International Filing Date of Jun. 3, 2019, which claims the benefit of, and priority to, U.S. Provisional Application Ser. No. 62/679,810, filed Jun. 2, 2018, U.S. Provisional Application Ser. No. 62/798,809, filed Jan. 30, 2019, and U.S. Provisional Application Ser. No. 62/809,354, filed Feb. 22, 2019, the contents of each of which are hereby incorporated by reference herein in their entireties.

FIELD OF THE INVENTION

The invention relates to deployable magnetic compression devices, and, more particularly, to systems, devices, and methods for the delivery, deployment, and positioning of magnetic compression devices at a desired site so as to improve the accuracy of anastomoses creation between tissues, organs, or the like.

BACKGROUND

Bypasses of the gastroenterological (GI), cardiovascular, or urological systems are typically formed by cutting holes in tissues at two locations and joining the holes with sutures or staples. A bypass is typically placed to route fluids (e.g., blood, nutrients) between healthier portions of the system, while bypassing diseases or malfunctioning tissues. The procedure is typically invasive, and subjects a patient to risks such as bleeding, infection, pain, and adverse reaction to anesthesia. Additionally, a bypass created with sutures or staples can be complicated by post-operative leaks and adhesions. Leaks may result in infection or sepsis, while adhesions can result in complications such as bowel strangulation and obstruction. While traditional bypass procedures can be completed with an endoscope, laparoscope, or robot, it can be time consuming to join the holes cut into the tissues. Furthermore, such procedures require specialized expertise and equipment that is not available at many surgical facilities.

As an alternative to sutures or staples, surgeons can use mechanical couplings or magnets to create a compressive anastomosis between tissues. For example, compressive couplings or paired magnets can be delivered to tissues to be joined. Because of the strong compression, the tissue trapped between the couplings or magnets is cut off from its blood supply. Under these conditions, the tissue becomes necrotic and degenerates, and at the same time, new tissue grows around points of compression, e.g., on the edges of the coupling. With time, the coupling can be removed, leaving a healed anastomosis between the tissues.

Nonetheless, the difficulty of placing the magnets or couplings limits the locations that compressive anastomosis can be used. In most cases, the magnets or couplings have to be delivered as two separate assemblies, requiring either an open surgical field or a bulky delivery device. For example, existing magnetic compression devices are limited to structures small enough to be deployed with a delivery conduit e.g., an endoscopic instrument channel or laparoscopic port. When these smaller structures are used, the formed anastomosis is small and suffers from short-term patency. Furthermore, placement of the magnets or couplings can be imprecise, which can lead to anastomosis formation in locations that is undesirable or inaccurate.

Thus, there still remains a clinical need for reliable devices and minimally-invasive procedures that facilitate compression anastomosis formation between tissues in the human body.

SUMMARY

Various embodiments of the invention provide improved devices and techniques for minimally-invasive formation of anastomoses within the body. Such devices and techniques facilitate faster and less-expensive treatments for chronic diseases such as obesity and diabetes. Such techniques also reduce the time and pain associated with palliative treatments for diseases such as cancers.

An embodiment of the invention may include one or more field controlled magnetic arrays (FCMAs), wherein each FCMA includes a support structure having a receptacle configured to receive and secure a plurality of small magnetic segments (SMSs). The SMSs may be individually oriented within the FCMA.

The receptacle is some embodiments may be configured to allow each SMS to be individually oriented with the FCMA, with their north magnetic poles at an orientation of 0°, 45°, 90°, 135°, 180°, 225°, 270°, or 315° with respect to a plane in the FCMA. In some embodiments, the SMSs may be individually oriented with their north magnetic poles at an orientation of 0°, 45°, 90°, 135°, 180°, 225°, 270°, or 315° with respect to a second plane in the FCMA.

In some embodiments of the invention, two or more of the SMSs may be different heights, different widths, different magnetic strengths, and/or different shapes. The shape of the SMSs may include, but are not limited to, rounded or rectangular.

In some embodiments, the invention may include an exoskeleton comprising a pocket capable of receiving an FCMA. The pocket may have an indentation capable of holding the FCMA in place. Some embodiments may include a securement device configured to secure the FCMA within the exoskeleton. The securement device may include, but not limited to, a screw and/or a band.

In various embodiments, the SMSs are arranged linearly within the FCMA.

In some embodiments, the FCMAs are arranged in a polygonal shape, including but not limited to an octagon. In some embodiments, the FCMAs may be arranged on the exterior circumference of the polygon, and/or may be arranged on the interior circumference of the polygon.

In some embodiments, two or more FCMAs are configured to secure a plurality of SMSs, wherein the SMSs are of varying heights. The two or more FCMAs may be configured to interlock.

Some embodiments of the invention may include an exoskeleton configured to secure an FCMA, wherein each FCMA is configured to secure a plurality of individually oriented SMSs. The exoskeleton may include a securement device configured to secure the FCMA within the exoskeleton. The securement device may be, but is not limited to, a screw and/or a band.

BRIEF DESCRIPTION OF THE DRAWINGS

Features and advantages of the claimed subject matter will be apparent from the following detailed description of embodiments consistent therewith, which description should be considered with reference to the accompanying drawings.

FIG. 9 illustrates the use of monopolar energy for piercing and accessing the gallbladder.

FIG. 10 illustrates the use of a fine aspiration needle (FNA) for piercing and accessing the gallbladder.

FIG. 11 illustrates the use of a corkscrew-type needle for piercing and accessing the gallbladder.

FIG. 12 illustrates the use of a guidewire passed through the bile duct.

FIG. 14 illustrates a T-bar member. FIG. 15 illustrates a nitinol coil (e.g., "pig tail"). FIG. 16 illustrates a balloon member of a catheter. FIG. 17 illustrates a malecot catheter.

FIGS. 25A, 25B, 25C, 25D, 25E illustrate a technique of accessing the gallbladder and delivering a pair of magnetic anastomosis devices for the formation of an anastomosis the gallbladder tissue and adjacent tissue (i.e., stomach or duodenum tissue).

FIGS. 26A, 26B, 26C illustrate a variation of the procedure and devices illustrated in FIGS. 25A-25E in that the deployment sheath includes a notch on a distal end thereof configured to engage the T-bar upon advancement through the enterotomy, thereby pushing the T-bar to the side to allow for subsequent delivery and deployment of the magnetic anastomosis device.

FIGS. 33A, 33B, and 33C illustrate a method of accessing the gallbladder, via endoscopic ultrasound guided access and utilizing a needle for access into the gallbladder, and subsequent delivery of a coiled stack of magnetic segments configured to serve the distal anastomosis device to correspondingly mate with a proximal magnetic anastomosis device positioned on the other side to subsequently compress tissue there between to form an anastomosis.

FIG. 45 provides a listing of some exemplary working channel sizes considered usable/feasible to deploy a magnetic array with a cage to produce an anastomosis.

FIG. 52B shows surface field strength of a configuration having orientations of 270°, 180°, 90°, 0°, 270° with equal size SMSs.

FIG. 52C shows surface field strength of a configuration having orientations of 0°, 180°, 0°, 180°, 0° with equal size SMSs.

FIG. 52D shows surface field strength of a configuration having orientations of 0°, 0°, 0°, 0°, 0° with equal size SMSs.

Figure 1:
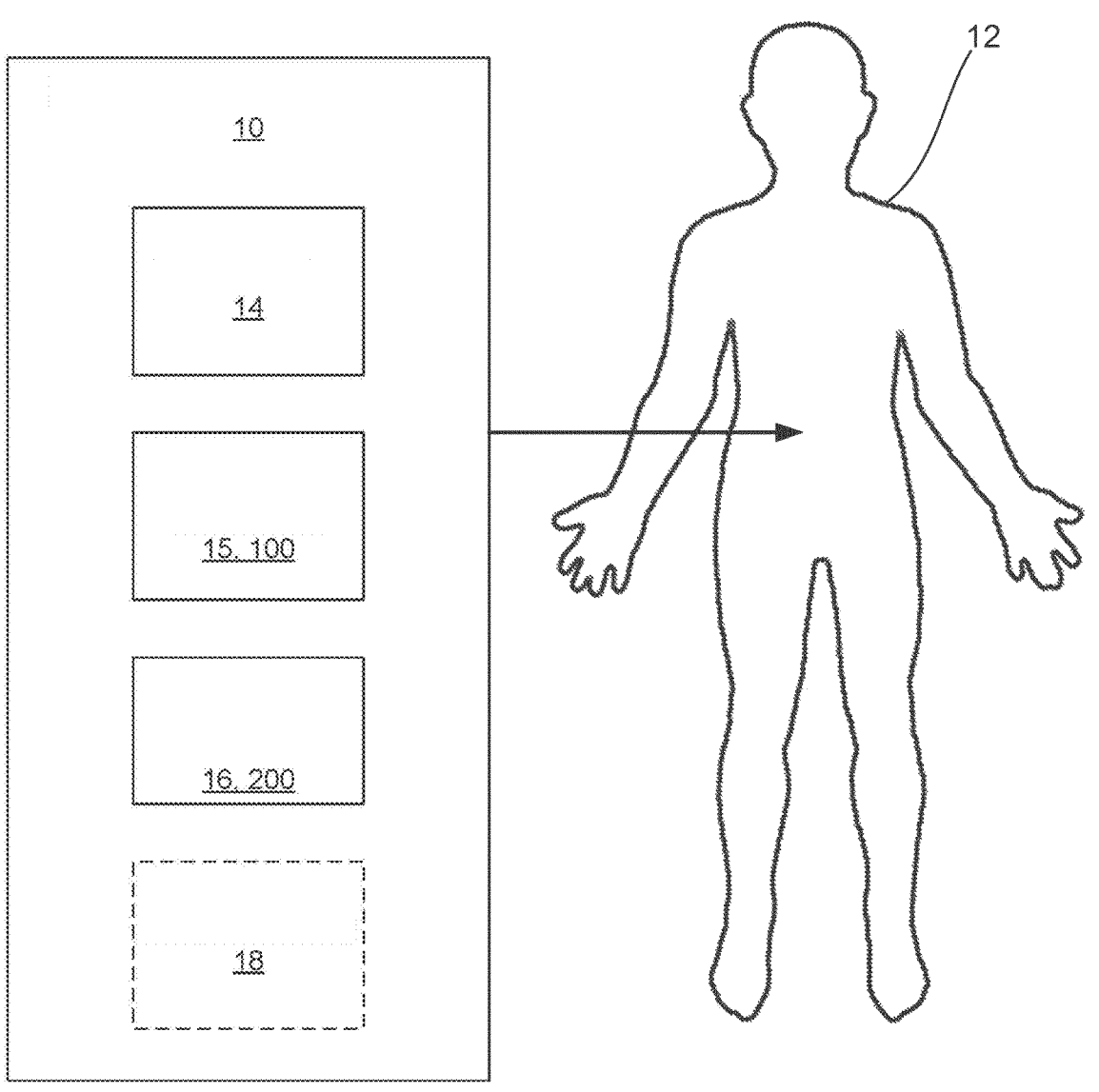
FIG. 1 is a schematic illustration of an anastomosis formation system consistent with the present disclosure.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

Exemplary embodiments provide improved devices and techniques for minimally-invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer.

The system generally includes an access device configured to be provided within a hollow body of a patient and assist in the formation of an anastomosis at a target site (a desired anatomical location) within the hollow body for formation of an anastomosis between a first portion of tissue of the hollow body at the target site and a second portion of tissue of the hollow body. The access device is configured to provide access to the first and second portions of tissue of the hollow body and further deliver and position first and second implantable magnetic anastomosis devices relative to the first and second portions of tissue or adjacent tissue for the formation of an anastomosis between tissues at the target site. The first and second implantable magnetic anastomosis devices are configured to be magnetically attracted to one another through a defined tissue area of the combined thickness of a wall of the tissues at the target site and exert compressive forces on the defined area to form the anastomosis.

The systems, devices, and methods described herein include, but are not limited to, various access devices for accessing a hollow body of the patient, such as a gallbladder, and securing positioning of the access device for the subsequent placement of one of a pair of magnetic anastomosis compression devices. The systems, devices, and methods described herein further include various delivery devices for delivering at least one of the pair of magnetic anastomosis compression devices to the target site, wherein, in some instances, a delivery device consistent with the present disclosure may assist in the deployment of at least one of the pair of magnetic anastomosis compression devices and subsequent securing to the target site and/or coupling the pair of magnetic anastomosis compression devices to one another. The systems, devices, and methods described herein include various embodiments of magnetic anastomosis compression devices and various designs for transitioning from a compact delivery configuration to a larger deployed configuration, generally by way of self-assembling design.

More specifically, exemplary embodiments provide a system including a delivery device for introducing and delivering, via a minimally-invasive technique, a pair of magnetic assemblies between adjacent organs to bridge walls of tissue of each organ together to thereby form a passage therebetween (i.e., an anastomosis). The delivery device is particularly useful in delivering the pair of magnetic assemblies to a target site within the gastrointestinal tract to thereby form anastomosis between gastric and gallbladder walls to provide adequate drainage from the gallbladder when blockage is occurring (due to disease or other health-related issues).

Accordingly, exemplary embodiments provide improved devices and techniques for minimally invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer.

FIG. 1 is a schematic illustration of an anastomosis formation system 10 for providing improved placement of magnetic anastomosis devices at a desired site so as to improve the accuracy of anastomoses creation between tissues within a patient 12. The system 10 generally includes an access device 14, a delivery device 15, 100, magnetic anastomosis devices 16, 200, and an imaging modality 18.

The access device 14 may generally include a scope, including, but not limited to, an endoscope, laparoscope, catheter, trocar, or other delivery device. For most applications described herein, the access device 14 is an endoscope, including a delivery needle configured to deliver the magnetic anastomosis devices 16, 200. Accordingly, the system 10 of the present disclosure relies on a single endoscope 14 for the delivery of the two magnetic devices 16, 200. As will be described in greater detail herein, a surgeon may advance the endoscope 14 within a hollow body of the patient 12 and position the endoscope 14 at the desired anatomical location for formation of the anastomosis based on a visual depiction of the location of the target site as provided by an imaging modality 18. For example, the imaging modality 18 may include a display in which an image, or other visual depiction, is displayed to the surgeon illustrating a target site when performing a medical imaging procedure, including, but not limited to, ultrasound (US), wavelength detection, X-ray-based imaging, illumination, computed tomography (CT), radiography, and fluoroscopy, or a combination thereof. The surgeon may then rely on such a visual depiction when advancing the endoscope 14 through the hollow body so as to position the access device 14 at a portion of tissue adjacent to the other portion of tissue at the target site, thereby ensuring the placement of the magnetic devices 16, 200 is accurate.

It should be noted that the hollow body through which the access device 14 may pass includes, but is not limited to, the stomach, gallbladder, pancreas, duodenum, small intestine, large intestine, bowel, vasculature, including veins and arteries, or the like.

In some embodiments, self-assembling magnetic devices are used to create a bypass in the gastrointestinal tract. Such bypasses can be used for the treatment of a cancerous obstruction, weight loss or bariatrics, or even treatment of diabetes and metabolic disease (i.e., metabolic surgery).

Figure 2:
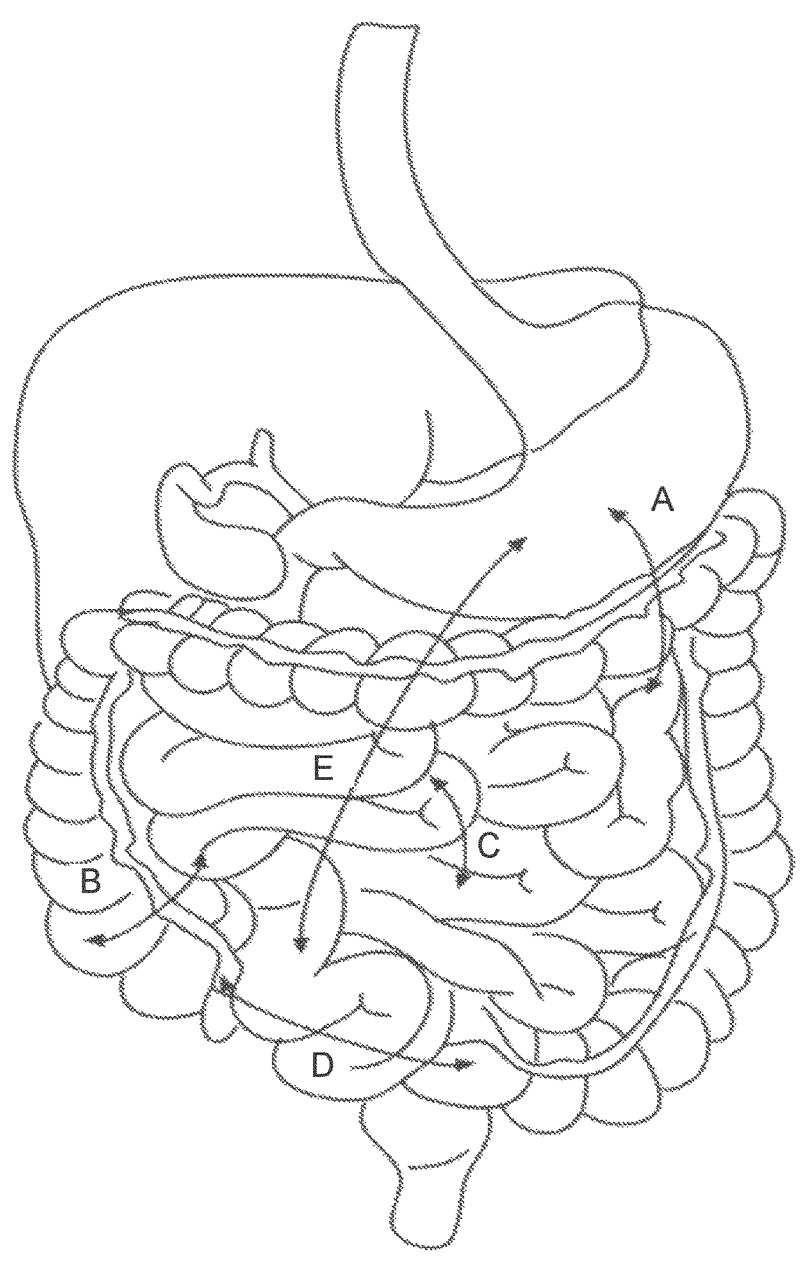
FIG. 2 shows several potential anatomical targets for anastomosis formation, where arrow A is stomach to small intestine, arrow B is small intestine to large intestine, arrow C is small intestine to small intestine, arrow D is large intestine to large intestine, and arrow E is stomach to large intestine.

FIG. 2 illustrates the variety of gastrointestinal anastomotic targets that may be addressed with the devices of certain exemplary embodiments, such targets include stomach to small intestine (A), stomach to large intestine (E), small intestine to small intestine (C), small intestine to large intestine (B), and large intestine to large intestine (D). Accordingly, exemplary embodiments provide improved devices and techniques for minimally-invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer.

For example, if the hollow body through which the access device 14 may pass is a bowel of the patient 12, the first portion may be a distal portion of the bowel and the second portion may be a proximal portion of the bowel. The bowel includes any segment of the alimentary canal extending from the pyloric sphincter of the stomach to the anus. In some embodiments, an anastomosis is formed to bypass diseased, mal-formed, or dysfunctional tissues. In some embodiments, an anastomosis is formed to alter the "normal" digestive process in an effort to diminish or prevent other diseases, such as diabetes, hypertension, autoimmune, or musculoskeletal disease. It should be noted that the system may be used for the formation of an anastomosis between a first portion of tissue of the hollow body at the target site and an adjacent tissue of a second hollow body (e.g., portal between the stomach and the gallbladder, the duodenum and the gallbladder, stomach to small intestine, small intestine to large intestine, stomach to large intestine, etc.).

Figure 3:
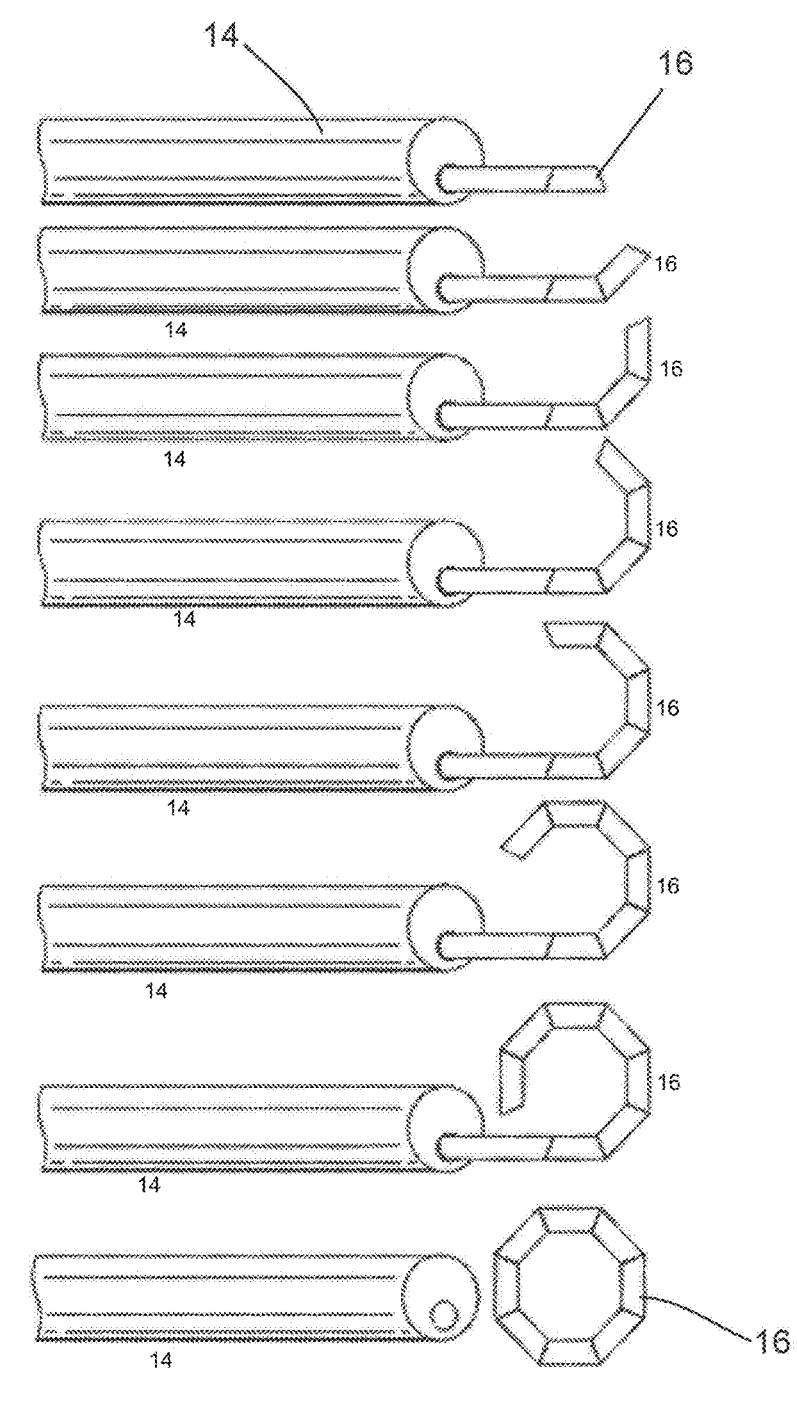
FIG. 3 shows an exemplary magnetic anastomosis device delivered through an endoscope instrument channel such that the individual magnet segments self-assemble into a larger magnetic structure—in this particular case, an octagon.

In an endoscopic procedure, the self-assembling magnetic devices 16, 100 can be delivered using a single endoscope 14. Deployment of a magnetic device 16 is generally illustrated in FIG. 3. As shown, exemplary magnetic anastomosis devices 16 may be delivered through an endoscope 14 such that individual magnet segments self-assemble into a larger magnetic structure—in this particular case, an octagon. When used with the techniques described herein, the devices 16 allow for the delivery of a larger magnetic structures than would otherwise be possible via a small delivery conduit, such as in a standard endoscope, if the devices were deployed as a completed assembly. Larger magnet structures, in turn, allow for the creation of larger anastomoses that are more robust, and achieve greater surgical success. For example, in some cases, resulting anastomosis may have a 1:1 aspect ratio relative to the final dimensions of the assembled magnetic devices. However, exemplary embodiments allow for larger aspect ratios (i.e., a larger anastomosis to form relative to the dimensions of the magnetic assemblies). In particular, prior art systems and methods that include the use of magnets for creating anastomosis are generally limited based on the dimensions of the working channel of the scope or catheter used for delivering such magnets, which, in turn, limits the resulting size of the anastomosis. However, the magnetic assembly design of exemplary embodiments overcome such limitations. For example, the design of the magnetic assembly, notably the coupling of multiple magnetic segments to one another via an exoskeleton, allow for any number of segments to be included in a single assembly, and thus the resulting anastomosis has a greater size relative to the dimensions of the working channel of the scope. For example, in some embodiments, the resulting anastomosis may include an aspect ratio in the range of 2:1 to 10:1 or greater. Such aspect ratios are described in greater detail with regard to FIGS. 44A, 44B, 44C, and 44D.

Because the magnetic devices are radiopaque and echogenic, the devices can be positioned using fluoroscopy, direct visualization (trans-illumination or tissue indentation), and ultrasound, e.g., endoscopic ultrasound. The devices 16 can also be ornamented with radiopaque paint or other markers to help identify the polarity of the devices during placement.

The magnetic anastomosis devices 16 generally comprise magnetic segments that can assume a delivery conformation and a deployed configuration. The delivery configuration is typically linear so that the device can be delivered to a tissue via a laparoscopic "keyhole" incision or with delivery via a natural pathway, e.g., via the esophagus, with an endoscope 14 or similar device. Additionally, the delivery conformation is typically somewhat flexible so that the device can be guided through various curves in the body. Once the device is delivered, the device will assume a deployed configuration of the desired shape and size by converting from the delivery configuration to the deployed configuration automatically. The self-conversion from the delivery configuration to the deployment configuration is directed by coupling structures that cause the magnetic segments to move in the desired way without intervention. Exemplary self-assembling magnetic anastomosis devices 16, such as self-closing, self-opening, and the like, are described in U.S. Pat. Nos. 8,870,898, 8,870,899, 9,763,664, and 10,182,821, the contents of each of which are incorporated by reference herein in their entirety.

Figure 4A:
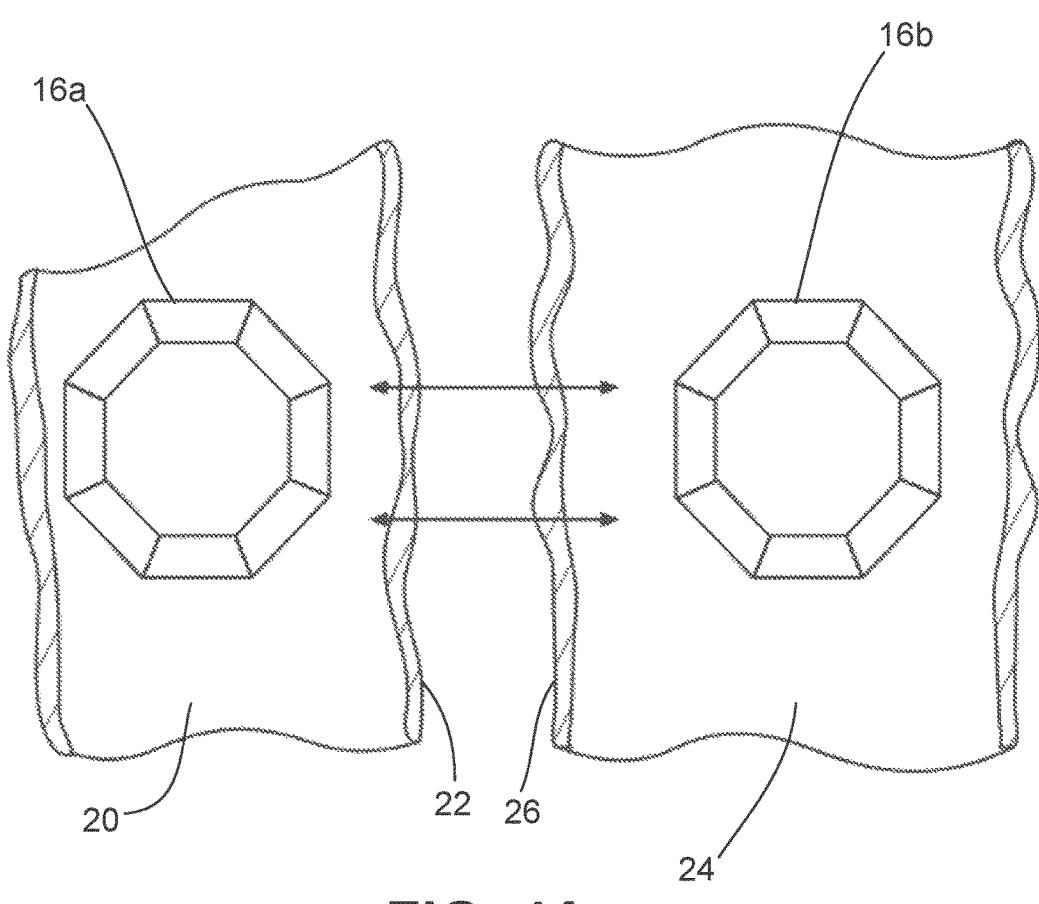
FIG. 4A depicts two magnetic anastomosis devices attracting each other through tissue. As shown, the devices each comprise eight magnetic segments, however alternate configurations are possible. Once the two devices mate, the tissue that is trapped between the devices will necrose, causing an anastomosis to form. Alternatively, the tissue bound by the devices may be perforated after the devices mate to create an immediate anastomosis.

In general, as shown in FIG. 4A, a magnetic anastomosis procedure involves placing a first and a second magnetic structures 16a, 16b adjacent to first and second portions 20, 24 of tissues 22, 26, respectively, thus causing the tissues 22, 26 to come together. Once the two devices 16a, 16b are brought into proximity, the magnetic structures 16a, 16b mate and bring the tissues 22, 26 together. With time, an anastomosis of the size and shape of the devices 16a, 16b will form and the devices will fall away from the tissue. In particular, the tissues 22, 26 circumscribed by the devices will be allowed to necrose and degrade, providing an opening between the tissues.

Figure 4B:
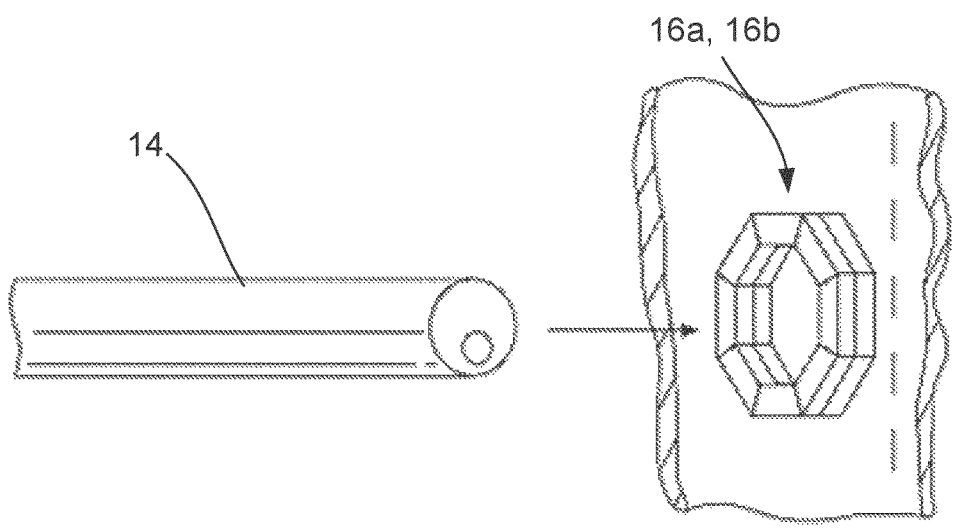
FIG. 4B shows the two magnetic anastomosis devices coupled together by magnetic attraction, capturing the intervening tissue. In some instances, the endoscope can be used to cut through the circumscribed tissue.

Alternatively, because the mated devices 16a and 16b create enough compressive force to stop the blood flow to the tissues 22, 26 trapped between the devices, a surgeon may create an anastomosis by making an incision in the tissues 22, 26 circumscribed by the devices, as shown in FIG. 4B.

In yet another embodiment, as will be described in greater detail herein, and shown in FIGS. 43A-43I, a surgeon may first cut into, or pierce, the tissues 22, 26, and then deliver a magnetic device 16a, 200a into a portion 20 of the hollow body so as to place device 16a, 200a around the incision on tissue 22. The surgeon may then place device 16b, 200b into portion 24 of the hollow body so as to deliver device 16b, 200b around the incision on tissue 26, and then allow the devices 16a, 200a and 16b, 200b to couple to one another, so that the devices 16a, 16b (200a, 200b) circumscribe the incision. As before, once the devices 16a, 16b (200a, 200b) mate, the blood flow to the incision is quickly cut off.

While the figures and structures of the disclosure are primarily concerned with annular or polygonal structures, it is to be understood that the delivery and construction techniques described herein can be used to make a variety of deployable magnetic structures. For example, self-assembling magnets can re-assemble into a polygonal structure such as a circle, ellipse, square, hexagon, octagon, decagon, or other geometric structure creating a closed loop. The devices may additionally include handles, suture loops, barbs, and protrusions, as needed to achieve the desired performance and to make delivery (and removal) easier. Yet still, in other embodiments, such as magnetic assembly 200 of FIG. 42, a magnetic assembly may comprise a pair of magnetic segments generally arranged in a linear alignment with one another (e.g., aligned in an end-to-end fashion) and coupled together via a flexible exoskeleton element. Such an embodiment will be described in greater detail herein.

Figure 5A:
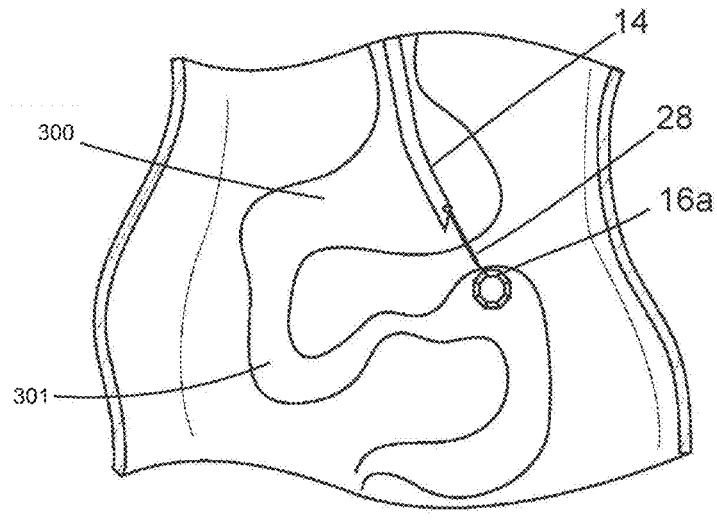
FIG. 5A shows the needle delivering a first magnetic device into a first portion of the hollow body at the target site.
Figure 5B:
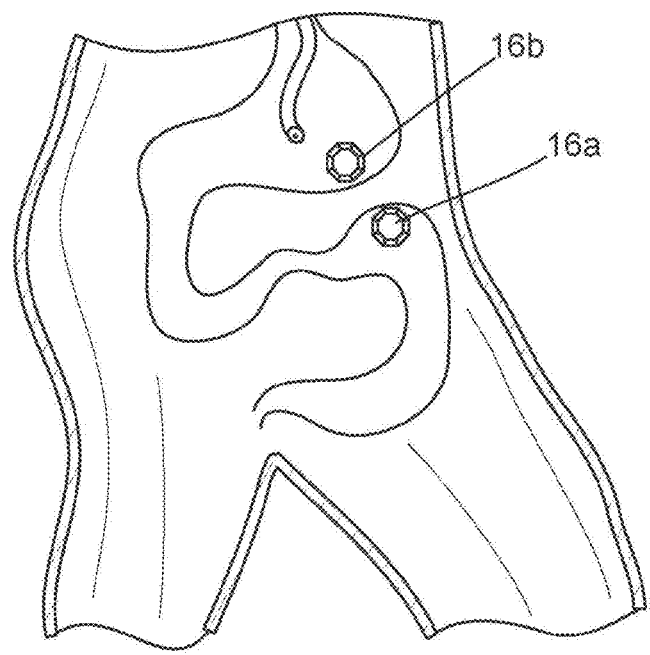
FIG. 5B shows subsequent deployment to of a second magnetic device into a second portion of the hollow body adjacent to the target site.

As previously described, the self-assembling magnetic anastomosis devices can be delivered to the target site via the access device 14. For example, as shown in FIG. 5A, the access device 14 may include a delivery needle 28 (e.g., an aspiration needle) used to deliver the first magnetic anastomosis device 16a into the lower small intestine (through the puncture), which is then followed by deployment to of a second magnetic device 16b into the upper small intestine at a location on the tissue adjacent to the target site (shown in FIG. 5B). It should be noted that the delivery can be guided with fluoroscopy or endoscopic ultrasound. Following self-assembly, these small intestine magnetic devices 16a, 16b couple to one another (e.g., magnetically attracted to one another) through a defined tissue area of the combined thickness of a wall of the tissues at the target site and exert compressive forces on the defined area to form the anastomosis.

Figure 6A:
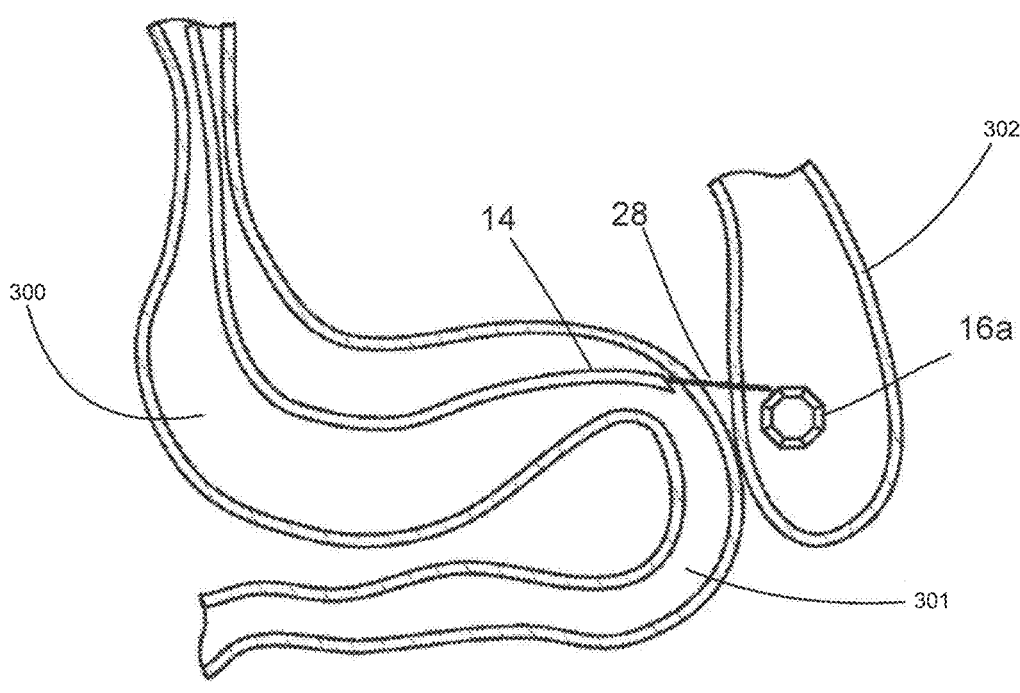
FIG. 6A shows endoscopic ultrasound guided needle delivery of a magnet assembly into the gallbladder which then couples with a second magnet assembly in the stomach or duodenum as shown in FIG. 6B.
Figure 6B:
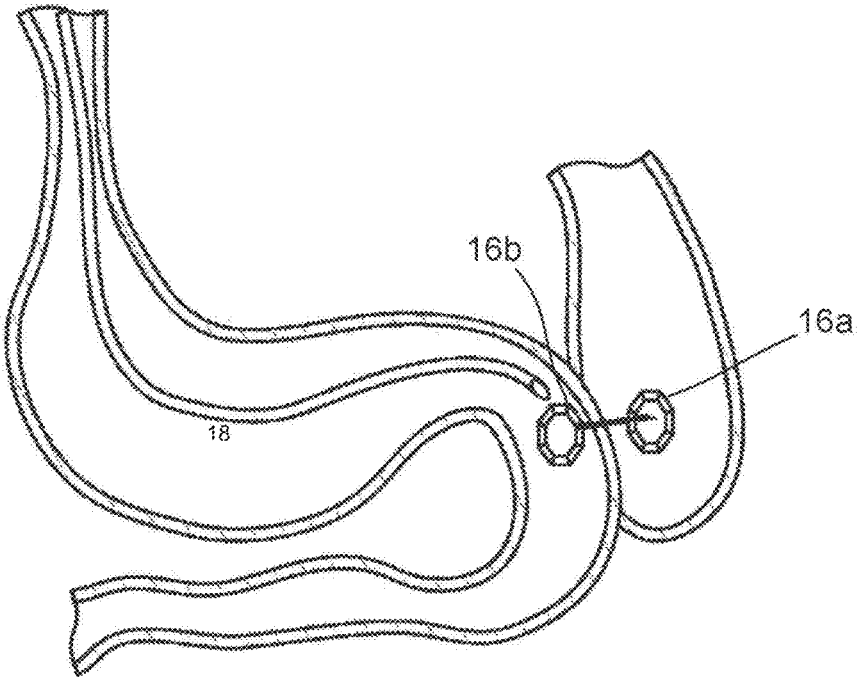

FIG. 6A shows endoscopic ultrasound guided needle 18 delivery of a magnet assembly 16a into the gallbladder 302 which then couples with a second magnet assembly 16b in the stomach 300 or duodenum 301 as shown in FIG. 6B. Accordingly, the described procedures may also be used with procedures that remove or block the bypassed tissues. For example, endoscopic ultrasound (EUS) can be used to facilitate guided transgastric or transduodenal access into the gallbladder 302 for placement of a self-assembling magnetic anastomosis device 16a. Once gallbladder 302 access is obtained, various strategies can be employed to maintain a patent portal between the stomach 300 and the gallbladder 302 or the duodenum 301 and the gallbladder 302. In another embodiment, gallstones can be endoscopically retrieved and fluid drained. For example, using the described methods, an anastomosis can be created between the gallbladder 302 and the stomach 300. Once the gallbladder 302 is accessed in a transgastric or transduodenal fashion, the gallstones can be removed. Furthermore, the gallbladder mucosa can be ablated using any number of modalities, including but not limited to argon plasma coagulation (APC), photodynamic therapy (PDT), sclerosant (e.g., ethanolamine or ethanol).

Figure 7:
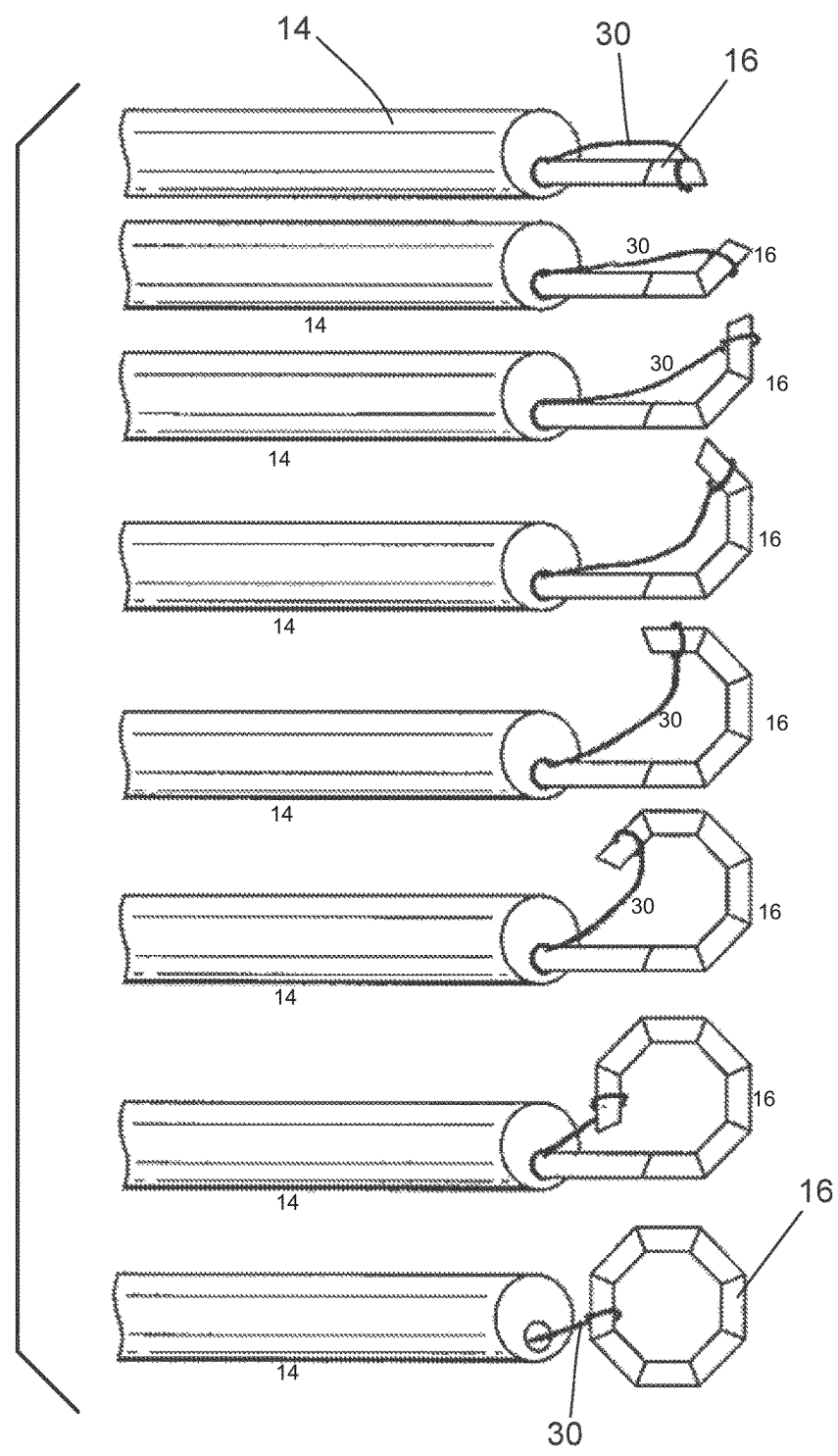
FIG. 7 illustrates a single guide element for deploying and manipulating a magnetic anastomosis device.
Figure 8A:
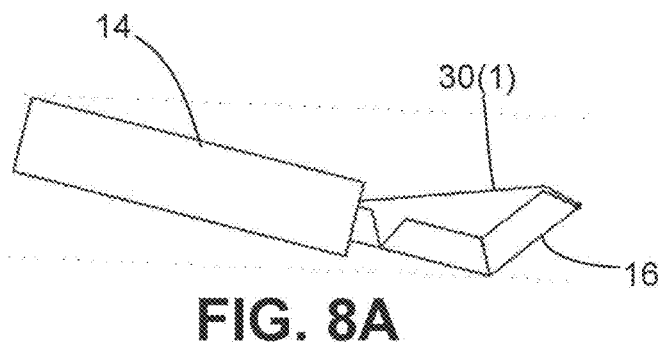
FIGS. 8A, 8B, 8C, 8D, 8E, and 8F each depict the deployment of the self-closing magnetic anastomosis device with a plurality of guide elements.
Figure 8B:
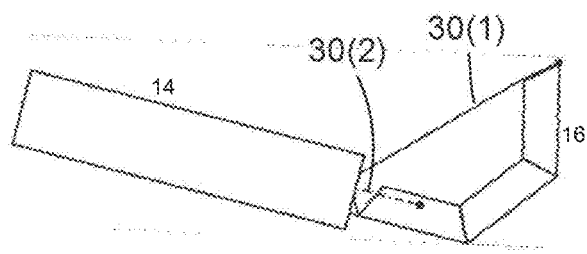
Figure 8C:
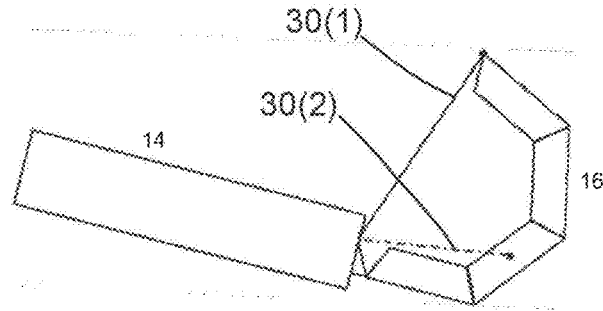
Figure 8D:
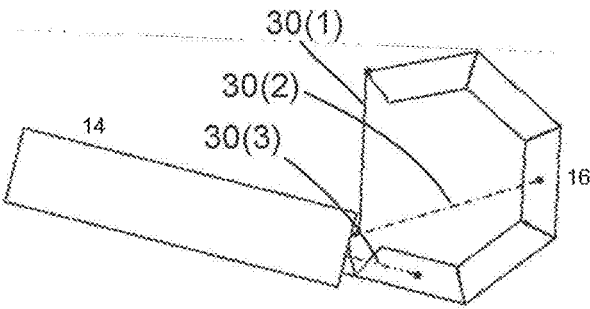
Figure 8E:
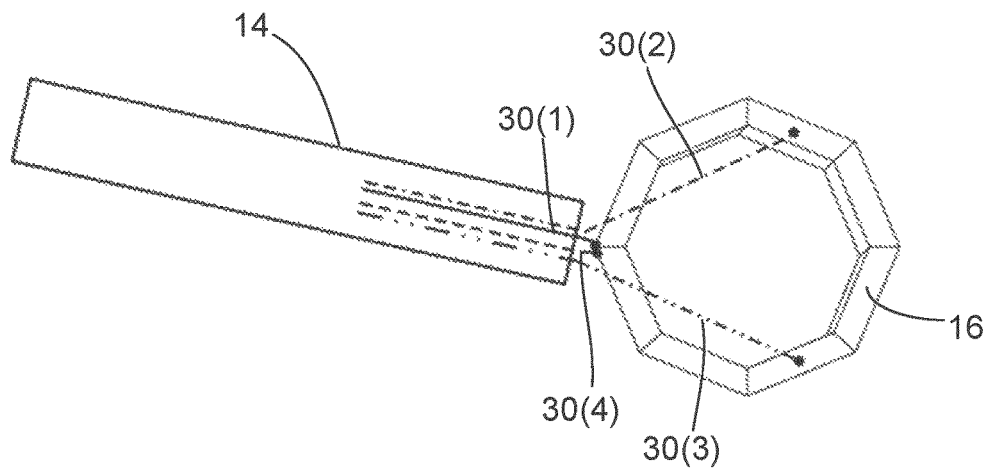
Figure 8F:
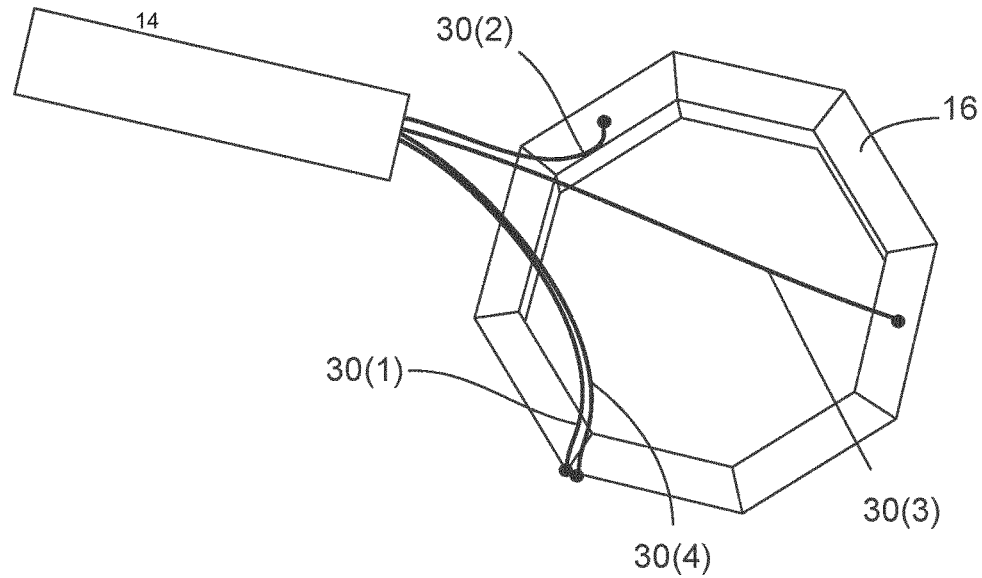

FIG. 7 illustrates a single guide element 30 for deploying and manipulating a magnetic anastomosis device 16. For example, once the self-assembling magnetic device 16 has been delivered to a tissue, it is beneficial to be able to manipulate the location of the device 16. While the device 16 can be manipulated with conventional tools such as forceps, it is often simpler to manipulate the location of the deployed device 16 with a guide element 30, such as a suture or wire. As shown in FIGS. 7 and 8A-8F, a variety of attachment points can be used to provide control over the location and deployment of a self-assembling magnetic anastomosis device 16. For example, as shown in FIG. 7, the guide element 30 may be coupled to a single distal segment such that, upon self-assembly, the single distal segment results in an attachment point that provides translational freedom of movement. It is also notable that the configuration shown in FIG. 7 also allows a closing force to be applied to the distal-most segment. That is, in the event that one or more segments should become entangled with tissue, or otherwise prevented from self-assembling, a proximal pulling force with the guide element 30 can help the device 16 to complete self-assembly. Once self-assembly is completed, the device 16 can be positioned with the guide element 30 to be mated with another device (not shown) to form an anastomosis, as described above. While it is not shown in FIG. 7, it is envisioned that additional structures, such as a solid pusher or a guide tube can be used to deploy the device 16 in the desired location.

The guide element 30 can be fabricated from a variety of materials to achieve the desired mechanical properties and bio-compatibility. The guide element 30 may be constructed from metal, e.g., wire, e.g., stainless steel wire, or nickel alloy wire. The guide element may be constructed from natural fibers, such as cotton or an animal product. The guide element may be constructed from polymers, such as biodegradable polymers, such as polymers including repeating lactic acid, lactone, or glycolic acid units, such as polylactic acid (PLA). The guide element may also be constructed from high-tensile strength polymers, such as Tyvek™ (high density polyethylene fibers) or Kevlar™ (para-aramid fibers). In an embodiment, guide element 30 is constructed from biodegradable suture, such as VICRYL™ (polyglactin 910) suture available from Ethicon Corp., Somerville, N.J.

In some embodiments, a magnetic anastomosis device 16 may include multiple guide elements 30. For example, as shown in FIGS. 8A, 8B, 8C, 8D, 8E, and 8F, a variety of attachment points can be used to provide control over the location and deployment of a self-assembling magnetic anastomosis device 16. As shown, four guide elements 30(1)-30(4) may be coupled to four separate segments of the device 16, respectively. Each guide element may include a distal end coupled to a respective portion of the anastomosis device, and a proximal end that can be manipulated (i.e., increased or decreased tension) to thereby manipulate the positioning and orientation of the anastomosis device once it has self-assembled into the predetermined shape (i.e., a polygon). For example, as shown, guide element 30(1) is coupled to the most distal end segment, guide elements 30(2) and 30(3) are coupled to middle segments (segments between the most distal end segment and most proximal end segment), and guide element 30(4) is coupled to the most proximal end segment.

Figure 9:
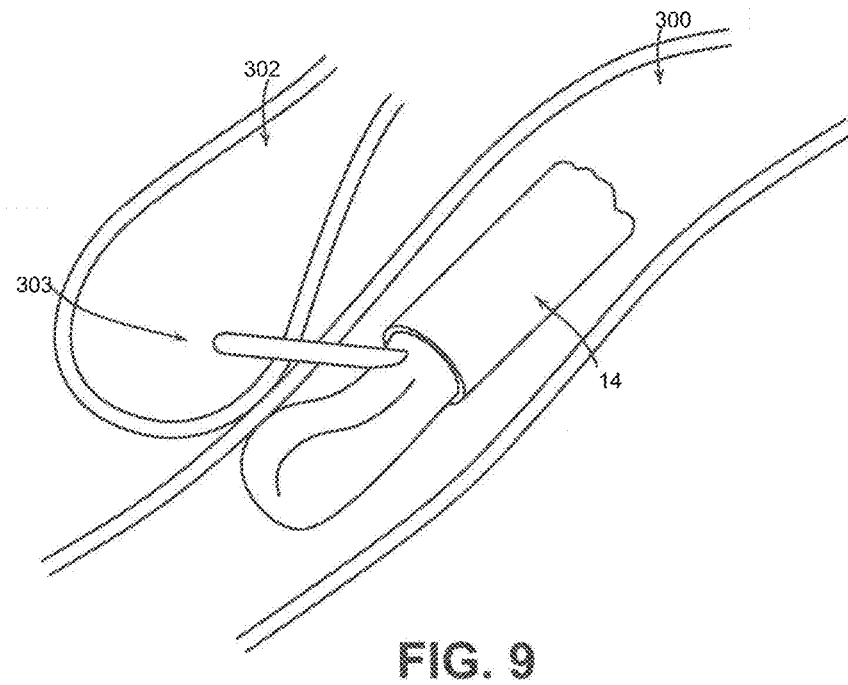
FIGS. 9, 10, 11, and 12 illustrate various methods of accessing the target site, specifically accessing a gallbladder via an endoscopic ultrasound guided procedure.

FIGS. 9-12 illustrates various methods of accessing the target site, specifically accessing a gallbladder 302 via an endoscopic ultrasound guided procedure. FIG. 9 illustrates the use of monopolar energy for piercing and accessing the gallbladder 302. An EUS scope 14 is advanced into the stomach 300 and against the stomach wall. A hot probe 303 utilizing monopolar energy pierces through the stomach wall into the gallbladder 302 in order to deliver a magnetic anastomosis device 16a.

Figure 10:
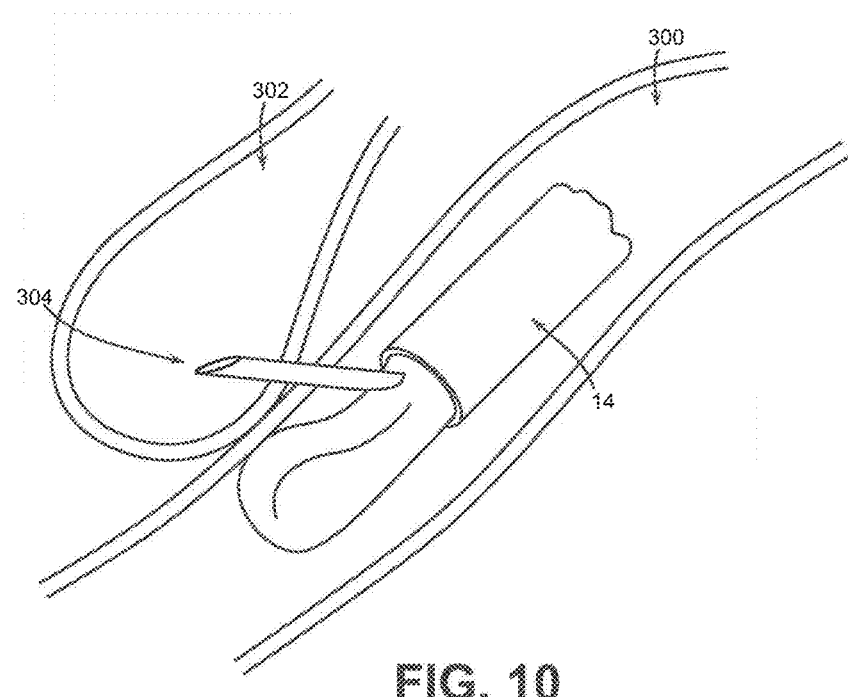

FIG. 10 illustrates the use of a fine aspiration needle 304 (FNA) for piercing and accessing the gallbladder 302. An EUS scope 14 is advanced into the stomach 300 and against the stomach wall. An FNA needle or hypotube with a cutting edge 304 pierces the stomach wall into the gallbladder 302 for delivery of a magnetic anastomosis device 16a.

Figure 11:
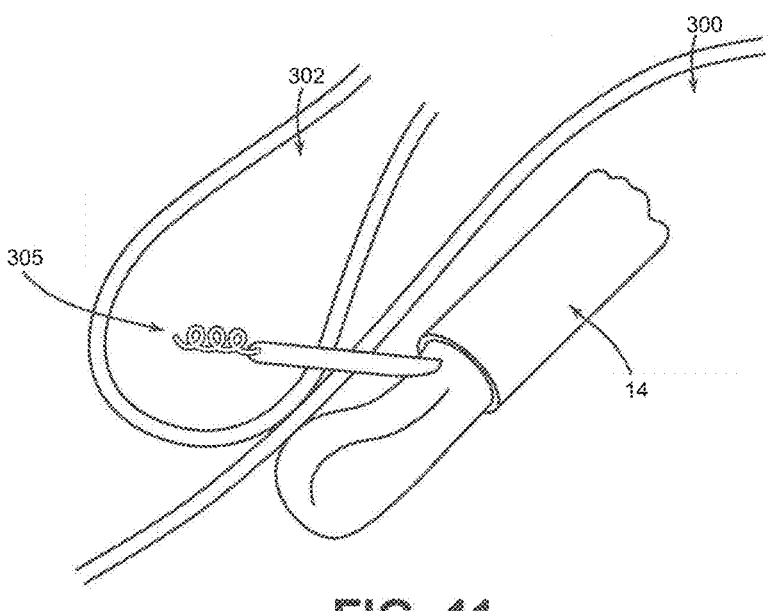

FIG. 11 illustrates the use of a corkscrew-type needle 305 for piercing and accessing the gallbladder 302. An EUS scope 14 is advanced into the stomach 300 and against the stomach wall. A corkscrew needle 305 pierces the stomach wall into the gallbladder 302 to deliver a magnetic anastomosis device 16a.

Figure 12:
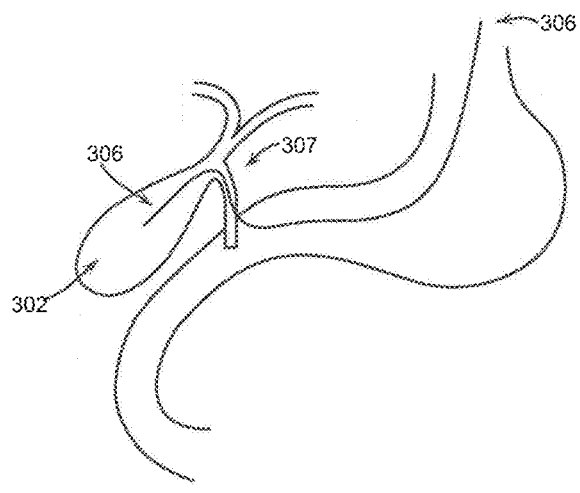

FIG. 12 illustrates the use of a guidewire 306 passed through the bile duct 307. A guidewire 306 is advance through the stomach 300, into the bile duct 307, and into the gallbladder 302 in order to deliver a magnetic anastomosis device 16a.

Figure 13:
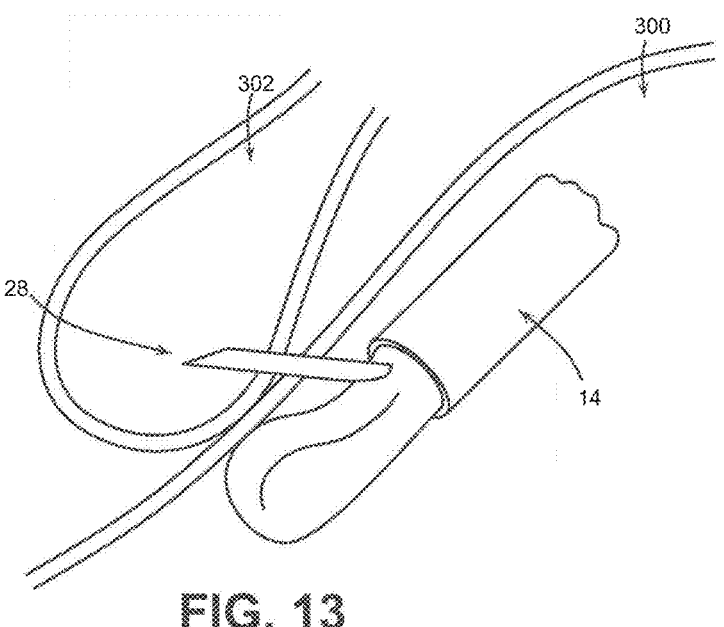
FIG. 13 shows endoscopic ultrasound guided needle piercing of the gallbladder to access the interior of the gallbladder for subsequent delivery of a magnet assembly therein.

FIG. 13 shows endoscopic ultrasound guided needle 14 piercing of the gallbladder 302 utilizing an access needle 28 to access the interior of the gallbladder 302 for subsequent delivery of a magnet assembly 16a therein.

Figure 14:
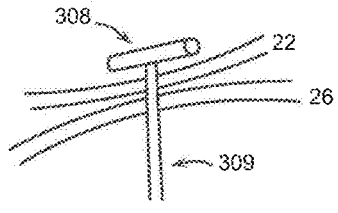
FIGS. 14, 15, 16 and 17 illustrate various devices for anchoring the access device and/or delivery device to the target site at the gallbladder.
Figure 15:
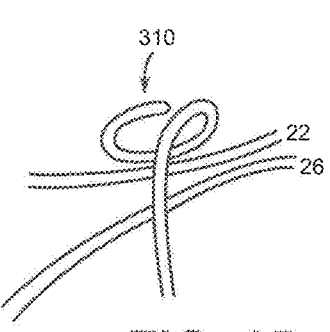
Figure 16:
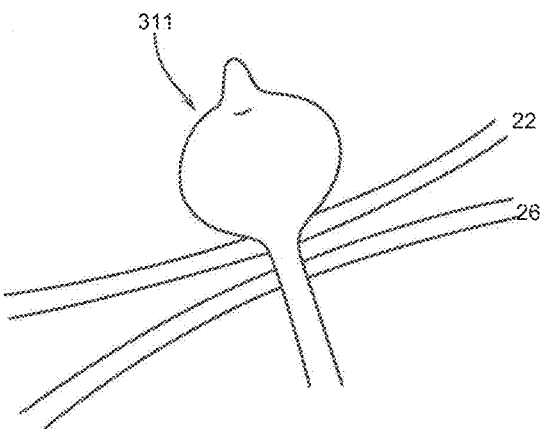
Figure 17:
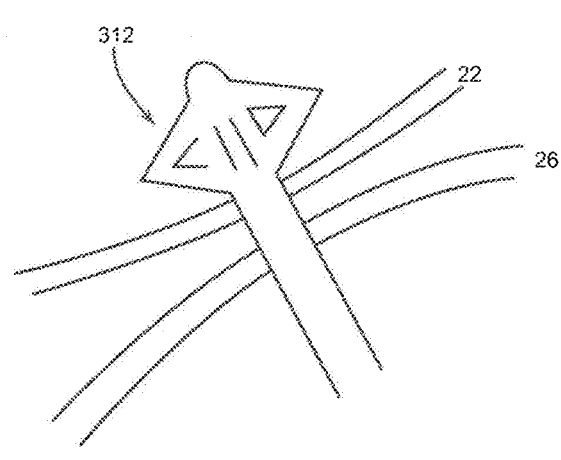

FIGS. 14, 15, 16 and 17 illustrate various devices for anchoring the access device and/or delivery device to the target site at the gallbladder. FIG. 14 illustrates a T-bar member 308 secured by a tether 309. FIG. 15 illustrates a preformed nitinol coil 310 (e.g., "pig tail"). FIG. 16 illustrates a balloon member of a catheter 311. FIG. 17 illustrates a malecot catheter 312.

FIGS. 18A-18F illustrate a method of accessing the gallbladder, via endoscopic ultrasound guided access 14 and utilizing an access device emitting monopolar energy 303, anchoring a delivery device via the use of a balloon catheter 311, and subsequently delivering a pair of magnetic anastomosis devices 16a, 16b within the balloon 311 while the balloon 311 is anchored within the formed enterotomy between the gallbladder tissue 22 and adjacent tissue 26 (i.e., stomach or duodenum tissue), thereby deploying the devices 16a, 16b on either side of the respective tissues 22, 26 (i.e., first device within the gallbladder 302 and second device within stomach 300 or duodenum 301) for the formation of an anastomosis there between.

Figure 18A:
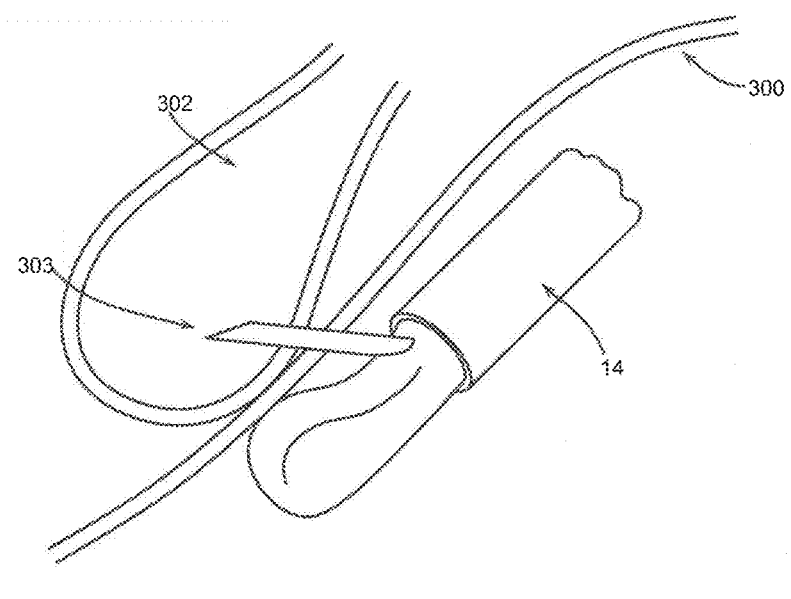
FIGS. 18A, 18B, 18C, 18D, 18E, and 18F illustrate a technique of accessing the gallbladder and delivering a pair of magnetic anastomosis devices for the formation of an anastomosis the gallbladder tissue and adjacent tissue.

FIG. 18A illustrates a EUS scope 14 being advanced through the stomach 300 against the stomach wall. A "hot probe" emitting monopolar energy 303 pierces through the stomach wall and into the gallbladder 302.

Figure 18B:
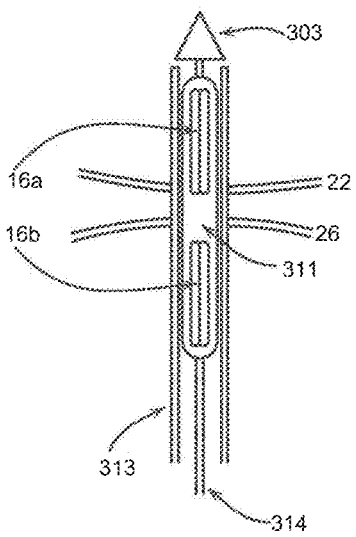
Figure 18C:
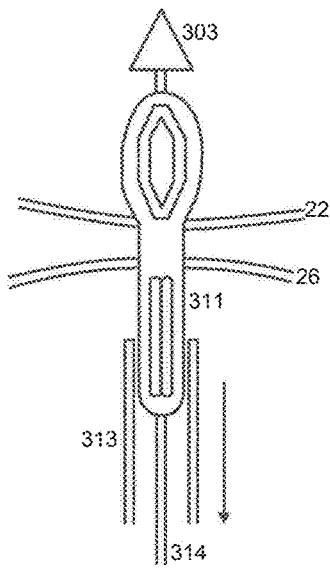
Figure 18D:
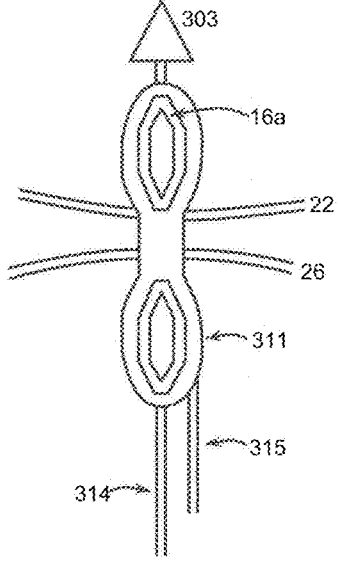

FIG. 18B illustrates the "hot tip" 303 piercing through the stomach wall 26, through the gallbladder tissue 22, and advanced into the gallbladder 302 utilizing a conductor 314. Within a deployment sheath 313, a balloon catheter 311 holds the collapsed magnetic assemblies 16a, 16b. The sheath 313 is removed by pulling back on the delivery device 14, as shown in FIG. 18C. This allows the first magnetic anastomosis device 16a to expand into the deployed configuration. Once the sheath 313 is fully removed, as shown in FIG. 18D, the balloon 311 is inflated using an inflation line 315. The inflation of the balloon 311 allows the magnets 16a, 16b to open fully.

Figure 18E:
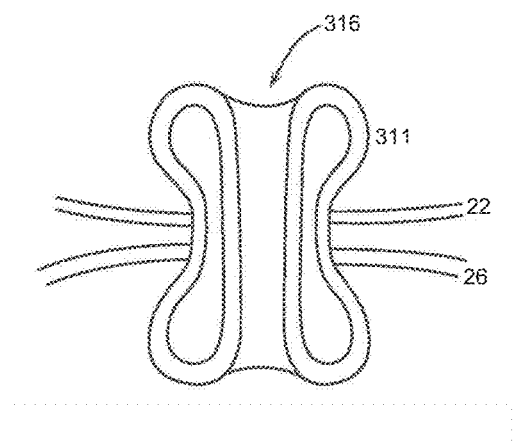

FIG. 18E illustrates a cross section of the balloon catheter 311. The balloon 311 has a "donut" shaped inner channel 316 to allow the passage of fluid and other material through the formed enterotomy.

Figure 18F:
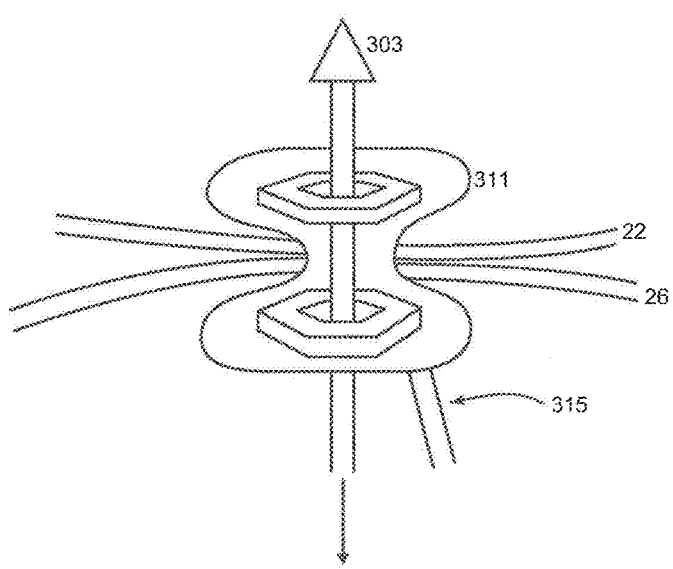

FIG. 18F illustrates a fully inflated balloon 311 with fully deployed magnetic anastomosis devices 16a, 16b. The hot tip 303 is removed, leaving behind the balloon 311 and magnets 16a, 16b.

Figure 19:
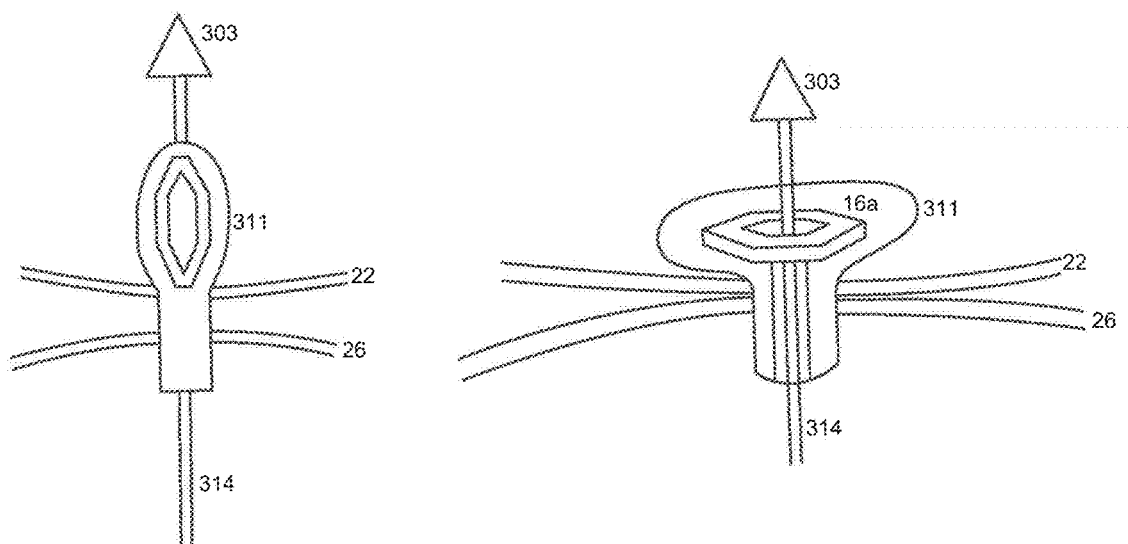
FIG. 19 illustrates a variation of design of FIGS. 18A-18F, specifically utilizing a balloon to deliver a single magnetic anastomosis device within the gallbladder, rather than delivering the pair.

FIG. 19 illustrates a variation of design of FIGS. 18A-18F, specifically utilizing a balloon 311 to deliver a single magnetic anastomosis device 16a within the gallbladder 302, rather than delivering the pair.

Figure 20A:
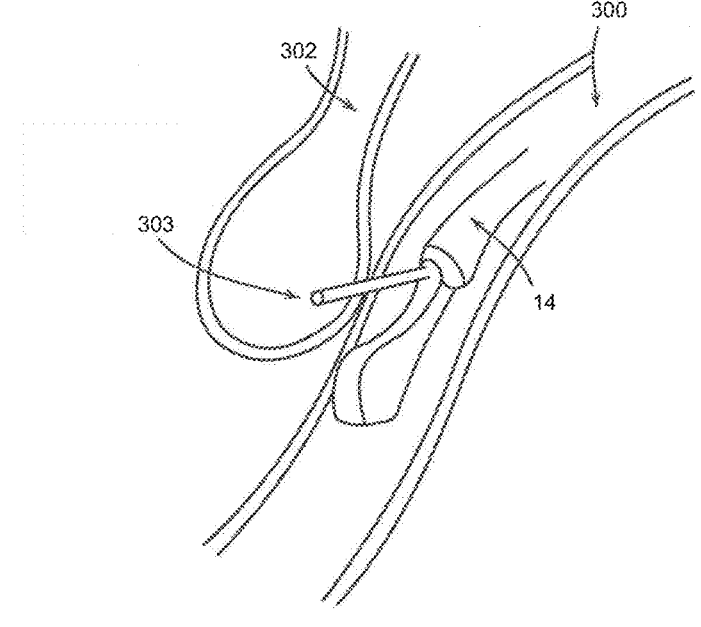
FIGS. 20A, 20B, and 20C illustrate a method of accessing the gallbladder, via endoscopic ultrasound guided access and utilizing a hot insertion tube emitting monopolar energy, and subsequently delivering a magnetic anastomosis device within the gallbladder via the hot tube.
Figure 20B:
Figure 20C:
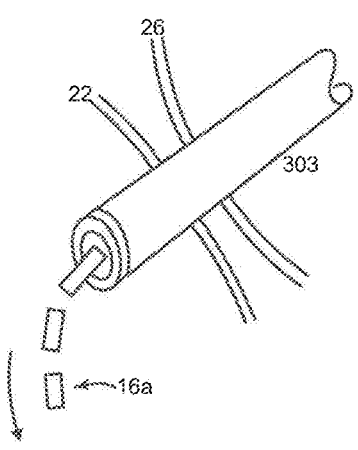

FIGS. 20A-20C illustrate a method of accessing the gallbladder 302, via endoscopic ultrasound guided access 14 and utilizing a hot insertion tube emitting monopolar energy 303, and subsequently delivering a magnetic anastomosis device 16a within the gallbladder 302 via the hot tube 303. As shown in FIG. 20A, an EUS scope 14 is advanced into the stomach 300 and against the stomach wall. A hot insertion tube emitting monopolar energy 303 pierces through the stomach wall into the gallbladder 302. As shown in FIG. 20B, a user need only activate monopolar energy to advance the insertion tube 303 through the tissues 22, 26 into the gallbladder 302. The magnetic anastomosis device 16a is deployed from the hot insertion tube 303 into the gallbladder 302, as shown in FIG. 20C.

Figure 21A:
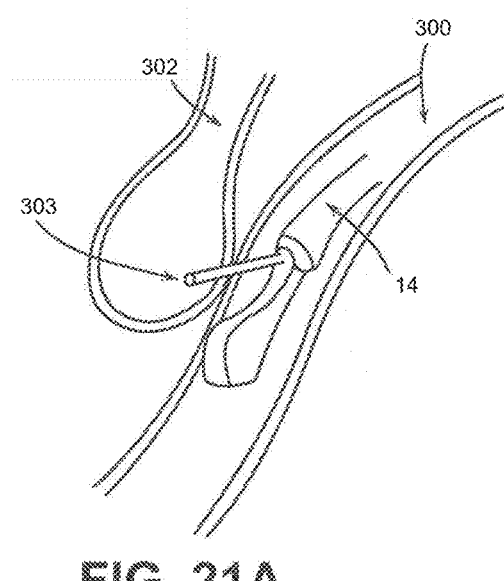
FIGS. 21A, 21B, 21C, 21D, and 21E illustrate a technique of accessing the gallbladder and delivering a pair of magnetic anastomosis devices for the formation of an anastomosis the gallbladder tissue and adjacent tissue.
Figures 21B, 21C, 21D:
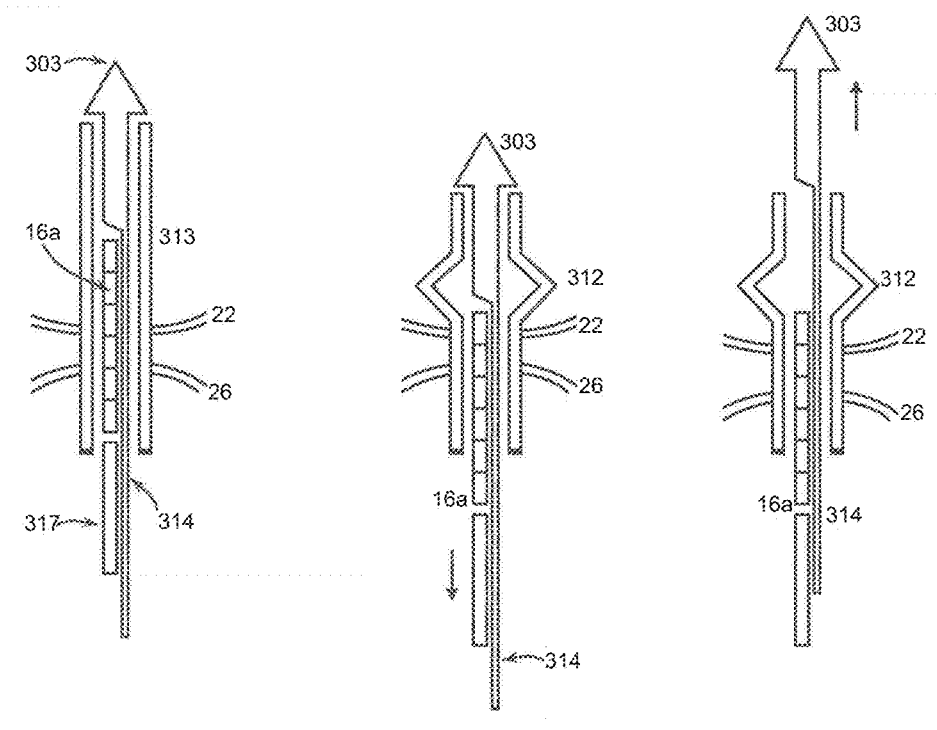
Figure 21E:
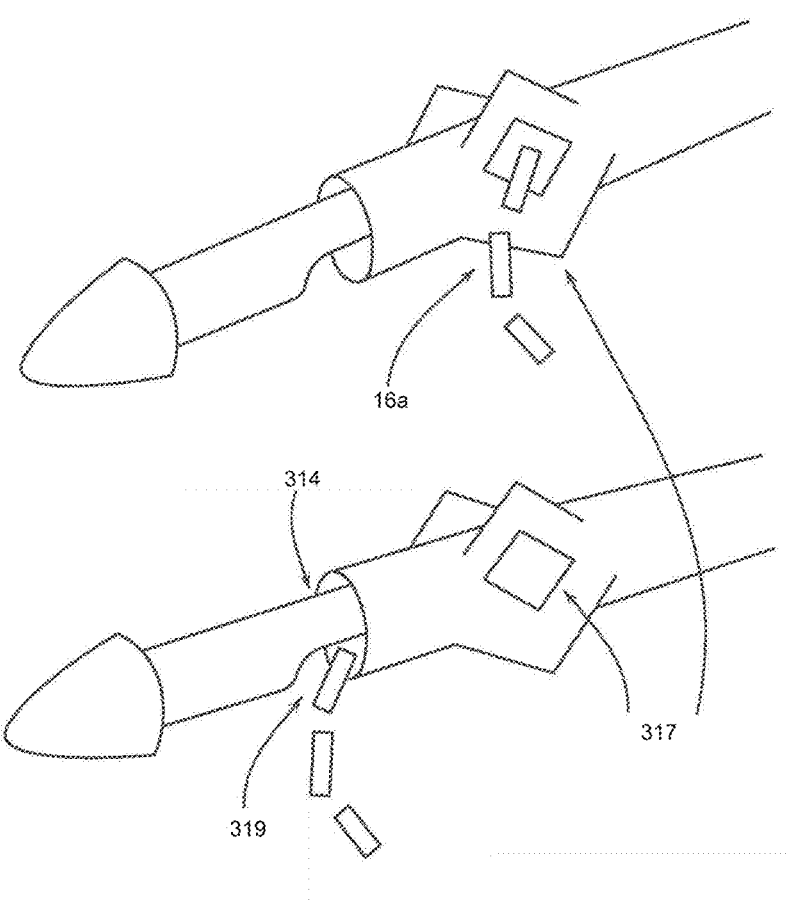

FIGS. 21A-21E illustrate a method of accessing the gallbladder 302, via endoscopic ultrasound guided access 14 and utilizing an access device having a conductor including a "hot" tip emitting monopolar energy 303, anchoring the delivery device via the use of a malecot catheter 312, and subsequently utilizing the malecot catheter 312 as a conduit for delivering a magnetic anastomosis device 16a there-through and into the gallbladder 302 while the malecot catheter 312 is anchored within the formed enterotomy between the gallbladder tissue 22 and adjacent tissue 26 (i.e., stomach or duodenum tissue). As shown in FIG. 21A, an EUS scope 14 is advanced into the stomach 300 to the stomach wall. A hot tip 303 pierces through the stomach wall into the gallbladder 302. As shown in FIG. 21B, the hot tip 303 is advanced into the gallbladder 302, advanced by a conductor 314. A push rod 317 capable of advancing the magnetic anastomosis device 16a is stored within the sheath 313 proximal to the magnet 16a. FIG. 21C illustrates how by pulling back on the conductor 314, the magnet 16a may be deployed into the lumen. The hot tip 303 is anchored against the gallbladder wall 22 by a malecot catheter 312. By pushing forward on the conductor 314, the user may advance only the tip into the gallbladder, as shown in FIG. 21D. FIG. 21E illustrates that by advancing the conductor 314, the magnets 16 may be deployed through the catheter's window 318, or through the end of the malecot catheter 319. The windows of the catheter 318 may be radio opaque to assist with direction and orientation.

Figures 22A, 22B, 22C:
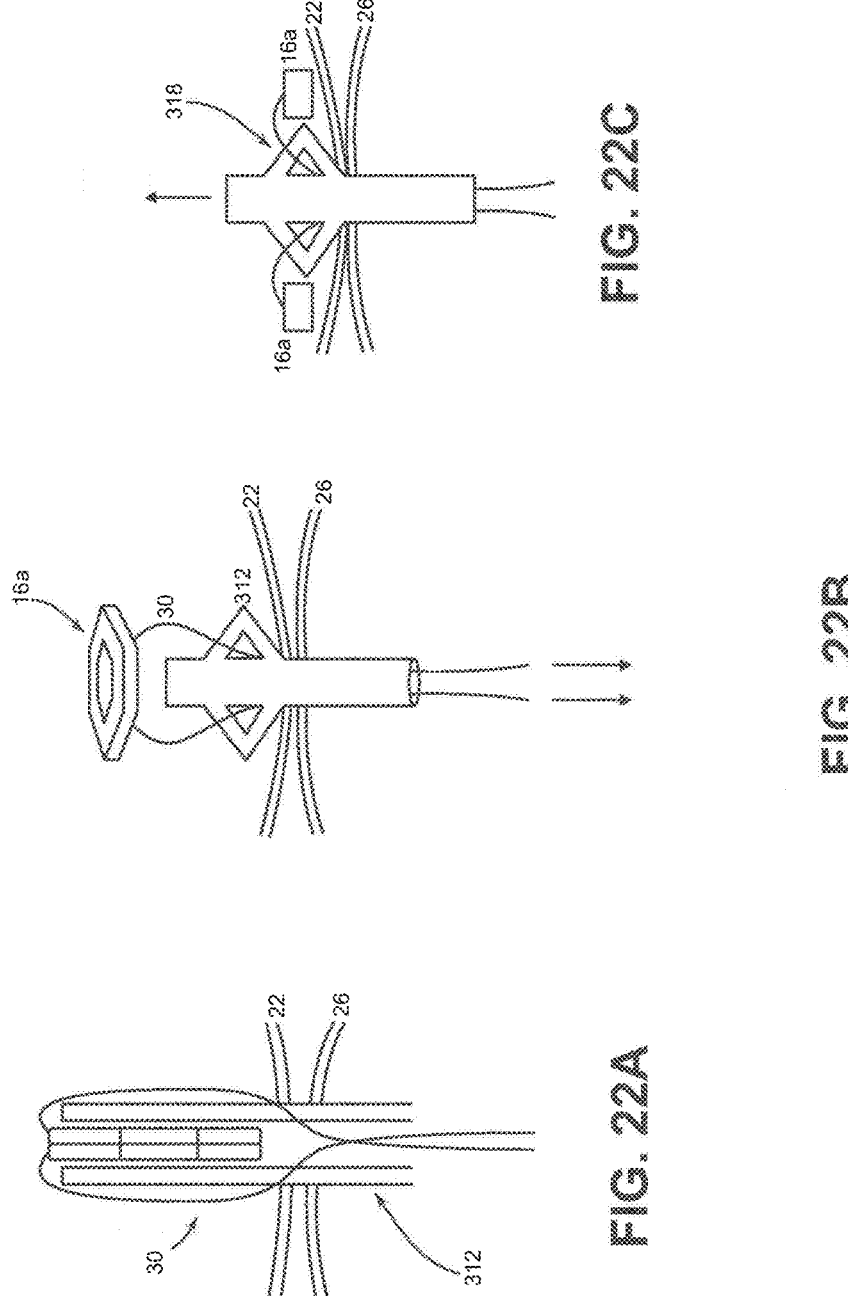
FIGS. 22A, 22B, and 22C illustrate a variation of the procedure and devices illustrated in FIGS. 21A-21E in that the magnetic anastomosis device is preloaded into a distal end of the malecot catheter of the delivery device resulting in delivery and deployment of the device upon transitioning of the malecot end into an anchored position.

FIGS. 22A-22C illustrate a variation of the procedure and devices illustrated in FIGS. 21A-21E in that the magnetic anastomosis device 16a is preloaded into a distal end of the malecot catheter 312 of the delivery device 14 resulting in delivery and deployment of the device 16a upon transition-ing of the malecot end into an anchored position. FIG. 22A illustrates the magnetic anastomosis device 16a preloaded into a distal end of a malecot catheter 312 with guide elements 30 securing the magnet 16a within the delivery device 14. As shown in FIG. 22B, by pulling back on the guide elements 30, the user may deploy the magnet 16a and transition the malecot catheter 312 into the anchored posi-tion against the gallbladder tissue wall 22. By pushing forward on the catheter 312, the windows 318 cut the guide elements 30, releasing the magnetic anastomosis device.

Figure 23:
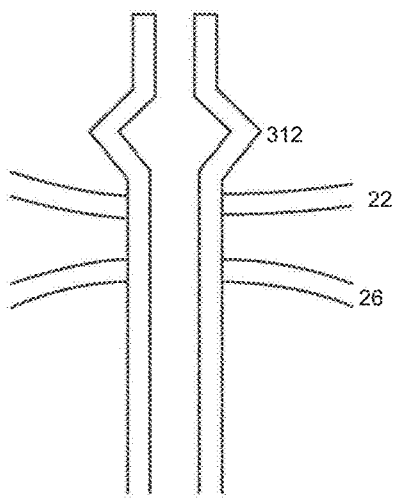
FIG. 23 illustrates a malecot catheter having a distal end that expands into the anchored position on one side of the gallbladder tissue wall.

FIG. 23 illustrates a malecot catheter 312 having a distal end that expands into the anchored position on one side of the gallbladder tissue wall 22.

Figure 24:
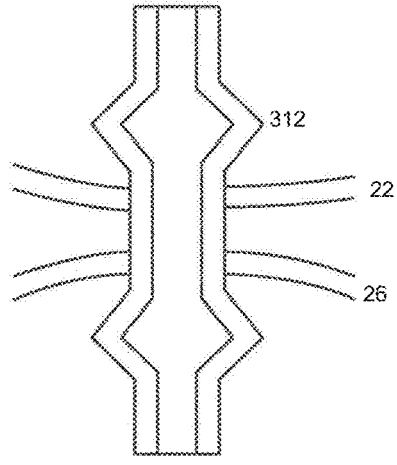
FIG. 24 illustrates a malecot catheter having a distal end that expands into the anchored position on both sides of the gallbladder tissue wall.

FIG. 24 illustrates a malecot catheter 312 having a distal end that expands into the anchored position on both sides of the gallbladder tissue wall 22, 26. In both instances, a temporary malecot may be placed inside of the gallbladder 302 to create a temporary conduit, which allows for drainage to occur immediately and could further allow for insufflation of the gallbladder 302 as well. It should be noted that, any of the embodiments that provide access from the GI tract into the gallbladder 302 (malecot 312, hot tube 303, nitinol coil 310, balloon 311, etc.), specifically any of the devices that creates a channel through which the magnetic anasto-mosis device 16 will pass, can also serve as a drainage channel. More specifically, after the access channel has been created, any fluid or material within the gallbladder 302 could be evacuated (either on its own or if suction is applied) before delivery of the magnetic anastomosis device 16 begins. The channel could also be used to push fluid into the gallbladder 302 prior to draining out the gallbladder 302 (potentially doing the fill/drain cycle a number of times) in order to 'clean' out the gallbladder 302 in the event that the gallbladder 302 has excess fluid and contents within (i.e., bile or other contents).

Figure 25E:
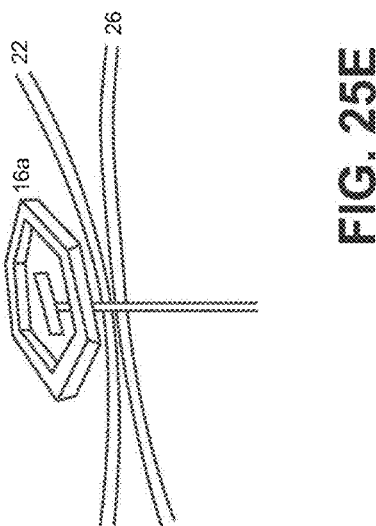
Figure 25D:
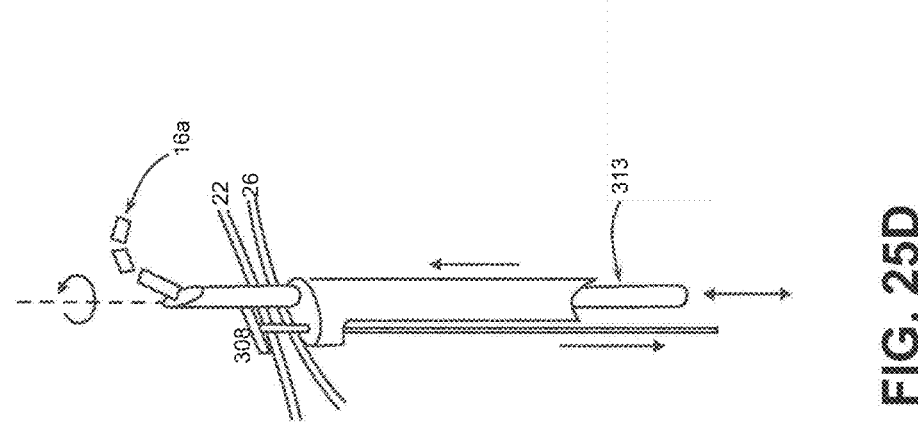

FIGS. 25A-25E illustrate a method of accessing the gallbladder 302, via endoscopic ultrasound guided access needle access 14, anchoring the delivery device via the use of a T-bar assembly 308 and stabilizer member 320, and subsequently delivering a magnetic anastomosis device 16a therethrough, via a deployment sheath 313, and into the gallbladder 302 while the T-bar 308 is anchored within the formed enterotomy between the gallbladder tissue 22 and adjacent tissue 26 (i.e., stomach or duodenum tissue). As shown in FIG. 25A, the T-bar 308 is tethered 309 to the gallbladder wall 22, as shown in FIG. 25B. The stabilizer member 320 is then advanced to the wall 26 of the duode-num 301 or stomach 300 for traction, as shown in FIG. 25C. The deployment sheath 313 is then advanced into the gallbladder 302, at which point the magnetic anastomosis device 16a can be delivered, as illustrated in FIG. 25D. The deployment sheath 313 may rotate in order to help deploy the magnet 16a. FIG. 25E illustrates that the magnetic anastomosis device 16a, when fully formed, may encase or surround the T-bar 308. The T-bar 308 could be metallic and able to stick to the magnet.

FIGS. 26A-26C illustrate a variation of the procedure and devices illustrated in FIGS. 25A-25E in that the deployment sheath 313 includes a notch 321 on a distal end thereof configured to engage the T-bar 308 upon advancement through the enterotomy, thereby pushing the T-bar 308 to the side to allow for subsequent delivery and deployment of the magnetic anastomosis device 16. FIG. 26A illustrates the deployment sheath 313 including a notch 321 on the distal end thereof configured to engage the T-bar 308 upon advancement through the enterotomy. FIG. 26B illustrates the notch 321 pushing the T-bar 308 to the side of the deployment sheath 313 to allow space for delivery of the magnetic anastomosis device 16. FIG. 26C illustrates the magnetic anastomosis device 16 being deployed with the T-bar 308 pushed to the side in the notch 321 of the deployment sheath 313.

Figure 27C:
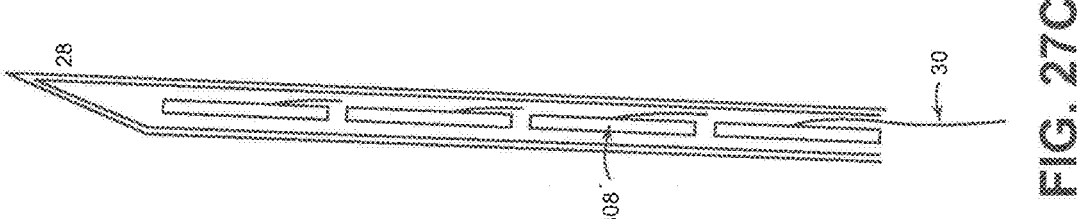
FIGS. 27A, 27B, and 27C illustrate another variation of the procedure and devices illustrated in FIGS. 25A-25E in that, rather than including a deployment sheath for delivering a self-assembling magnetic anastomosis device, as previously described herein, the assembly of FIGS. 27A-27C relies on the depositing of T-bars through an access needle, such that a grouping of T-bars are configured to self-assembly into an array and serve as the distal anastomosis device to correspondingly mate with a proximal magnetic anastomosis device positioned on the other side to subsequently compress tissue there between to form an anastomosis.
Figure 27B:
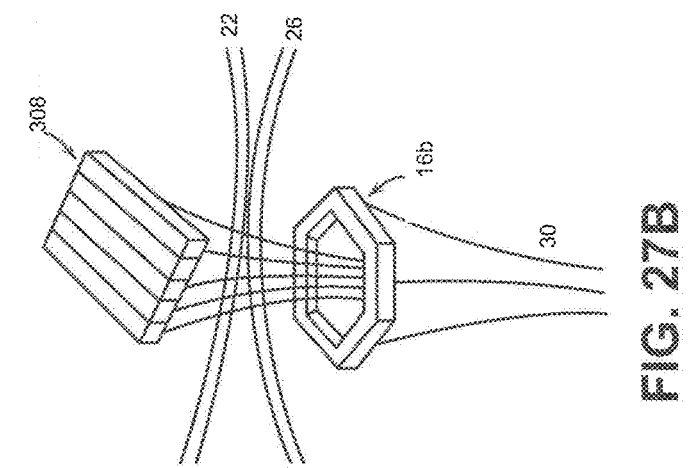
Figure 27A:
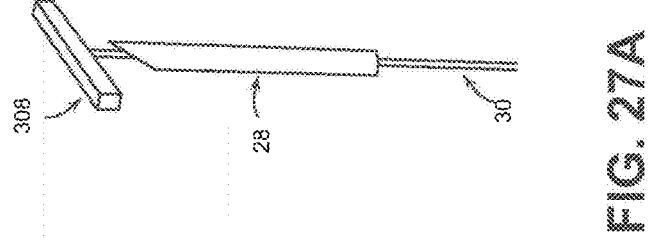

FIGS. 27A-27C illustrate another variation of the proce-dure and devices illustrated in FIGS. 25A-25E in that, rather than including a deployment sheath 313 for delivering a self-assembling magnetic anastomosis device 16, as previously described herein, the assembly of FIGS. 27A-27C relies on the depositing of T-bars 308 through an access needle 28, such that a grouping of T-bars 308 are configured to self-assemble into an array and serve as the distal anastomosis device 16a to correspondingly mate with a proximal magnetic anastomosis device 16b positioned on the other side to subsequently compress tissues 22, 26 there between to form an anastomosis. FIG. 27A illustrates a T-bar assembly 308 being delivered through an access needle 28. By pulling back on the delivery device 14, the user is able to deploy the T-bar 308 into the distal lumen. The T-bar 308 is secured in place by guide elements 30 or sutures. FIG. 27B illustrates a fully deployed array of T-bars 308. In some embodiments, the T-bars 308 are magnetic and able to attract the proximal anastomosis device 16b. By pulling on the guide elements 30, the user is able to bring the T-bar 308 array toward the proximal anastomosis device 16b in order to create an anastomosis therebetween. FIG. 27C illustrates the T-bar 308 array and guide elements 30 or sutures loaded linearly in the access needle 28. Loading the T-bars 308 linearly allows for a minimally invasive creation of an anastomosis. Because the magnetic assemblies are loaded linearly and then self-assemble, the aspect ratio of the resulting anastomosis can be greater than 1:1 as the magnetic assemblies assemble to a size greater than the diameter of the access needle. This allows for the creation of larger anastomoses while still maintaining a minimally invasive procedure FIGS. 28A-28C illustrate a method of accessing the gallbladder, via endoscopic ultrasound guided access needle access, utilizing a side port deployment sheath for delivery and deployment of a pair of magnetic anastomosis devices.

Figure 28A:
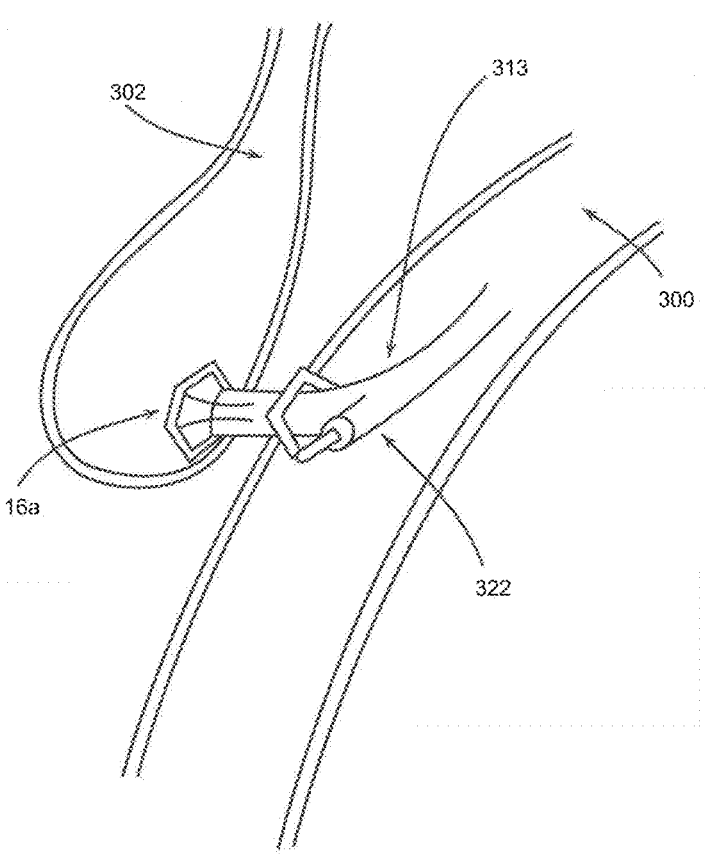
FIGS. 28A, 28B, and 28C illustrate a method of accessing the gallbladder, via endoscopic ultrasound guided access needle access, utilizing a side port deployment sheath for delivery and deployment of a pair of magnetic anastomosis devices.

FIG. 28A illustrates a method of accessing the gallbladder 302 in order to deploy a distal magnetic anastomosis device 16a. The delivery device 14 accesses the stomach 300/duodenum 301 and pierces through the stomach tissue wall 26 into the gallbladder 302. The delivery device 14 in this embodiment has a side port 322 for deployment of the proximal magnetic anastomosis device 16b.

Figure 28B:
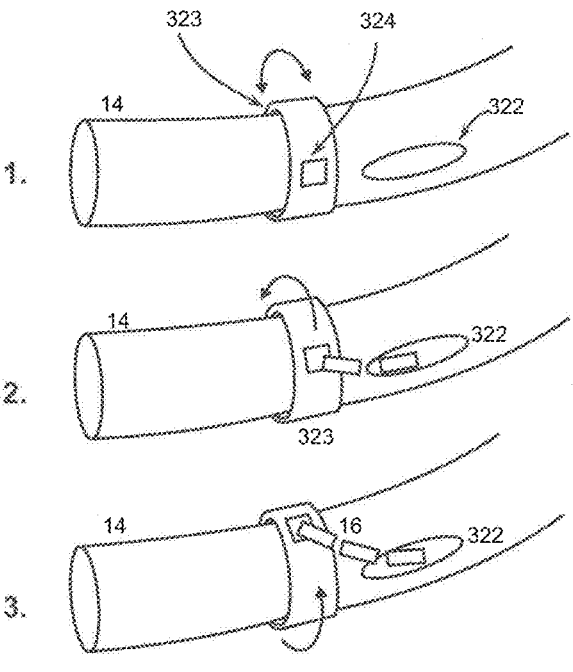

FIG. 28B illustrates a rotating ring 323 with a metal insert 324 consistent with some embodiments of the invention. The rotating ring 323 is capable of rotating around the shaft of the delivery device 14. As the magnetic devices 16 are deployed from the side port 322 of the delivery device 14, the metal insert 324 on the rotating ring 323 catches the magnetic devices 16 and guides the magnets 16 out of the delivery device 14 and around the shaft of the delivery device 14 in order to aid self-assembly of the magnetic anastomosis devices 16. The rotating ring 324 in some embodiments may be free spinning, or may rotate when the magnet 16 is pushed out of the delivery device 14. In some embodiments the rotating ring 324 may be actively rotated to pull the magnetic device 16 out of the delivery device 14.

Figure 28C:
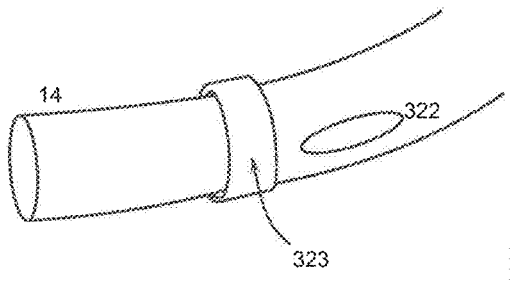

FIG. 28C is a close-up view of the rotating ring 323 on the shaft of the delivery device 15. The rotating ring 323 may be made of metal in some embodiments.

Figure 29A:
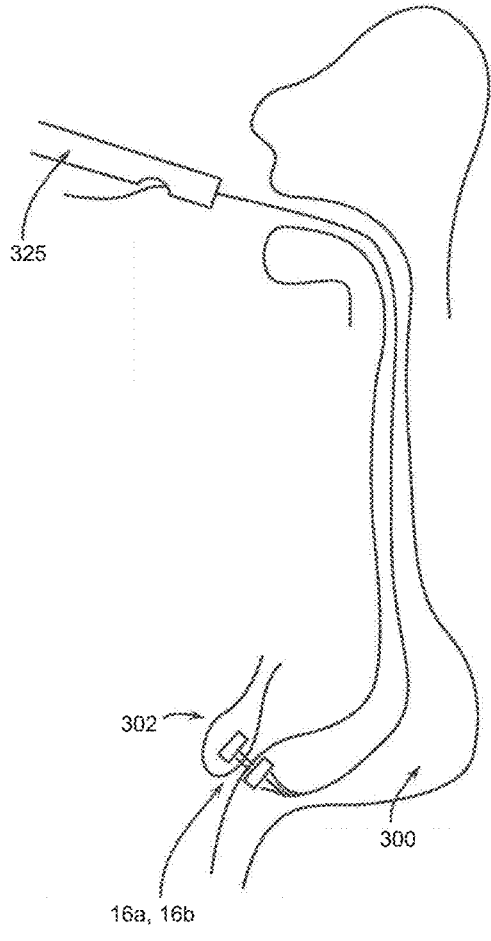
FIGS. 29A, 29B, and 29C illustrate a knotting member configured to secure already deployed and positioned magnetic anastomosis devices to the target site tissues and subsequently cut guide elements or sutures coupled thereto.
Figure 29B:
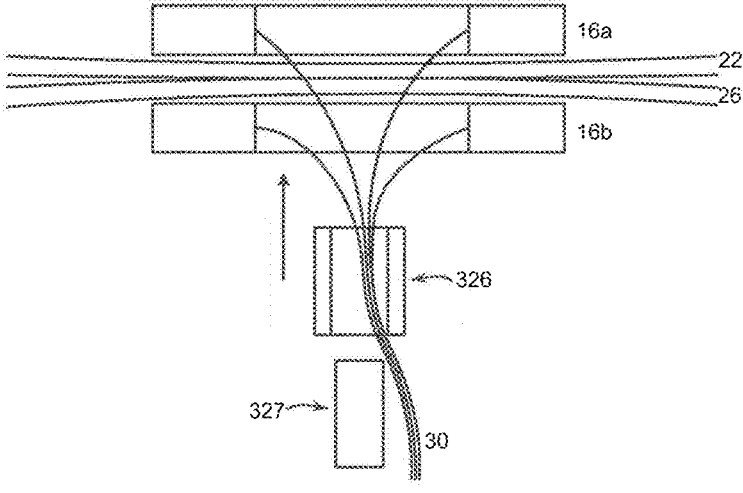
Figure 29C:
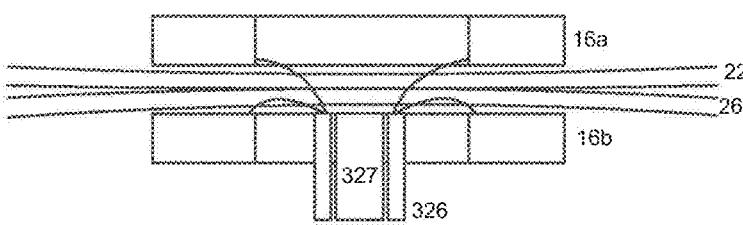

FIGS. 29A-29C illustrate a knotting member 325 configured to secure already deployed and positioned magnetic anastomosis devices 16a, 16b to the target site tissues 22, 26 and subsequently cut guide elements 30 or sutures coupled thereto. As shown in FIG. 29A, the knotting member 325 is advanced over guide elements 30 within a working channel of a scope 14. The guide elements 30 are positioned through the patient 12 to the stomach 300 and connected to previously placed compression anastomosis devices 16a, 16b in the gallbladder 302 and stomach 300.

As shown in FIG. 29B, the knotting member 325 advances towards the magnetic anastomosis devices 16a, 16b, wherein the knotting member 325 generally consists of an outer tube member 326 and an inner rod member 327, such that, upon reaching the devices 16a, 16b, the inner rod member 327 can be pressed towards a distal end of the outer tube member 326, thereby securing a portion of the guide elements 30 there between and further cutting the guide elements 30 in the process. FIG. 29C illustrates the knotting member 325 being fully advanced to the magnetic anastomosis devices 16a, 16b, thereby securing the guide elements 30 and further cutting the guide elements 30.

Figures 30A, 30B:
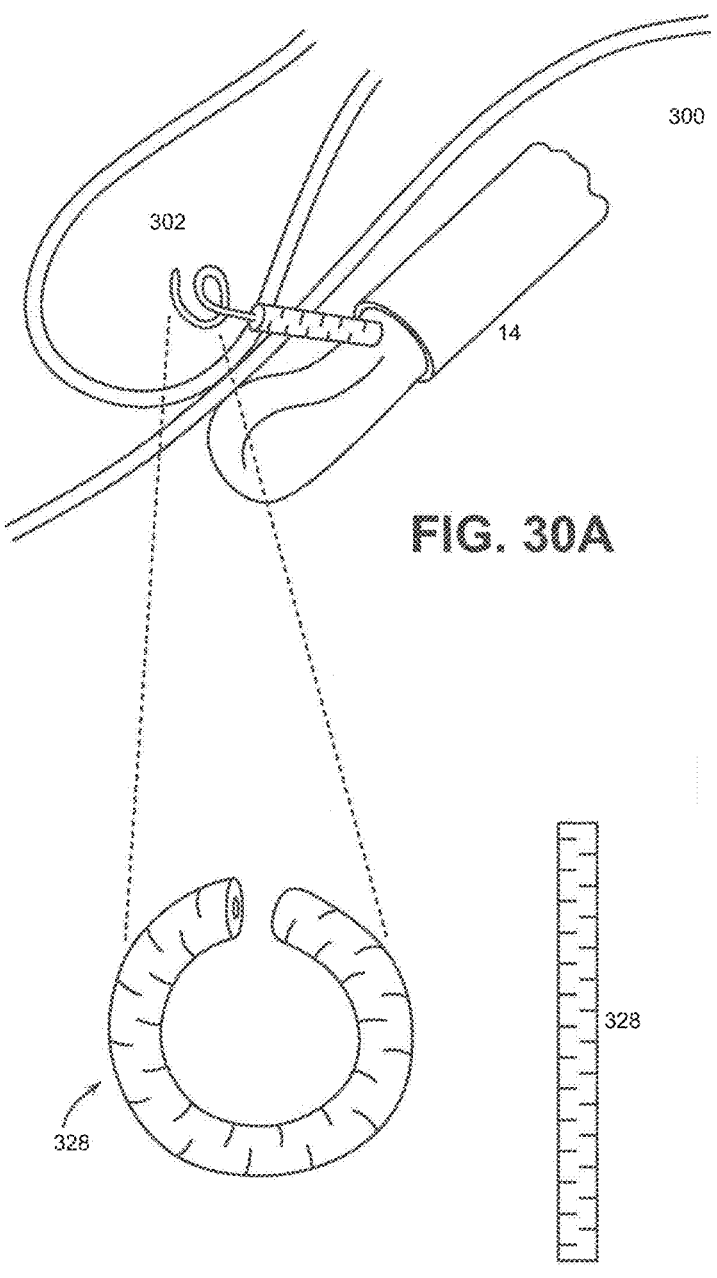
FIGS. 30A, 30B, 30C, and 30D illustrate a technique of accessing the gallbladder and delivering a pair of magnetic anastomosis devices for the formation of an anastomosis the gallbladder tissue and adjacent tissue.
Figure 30C:
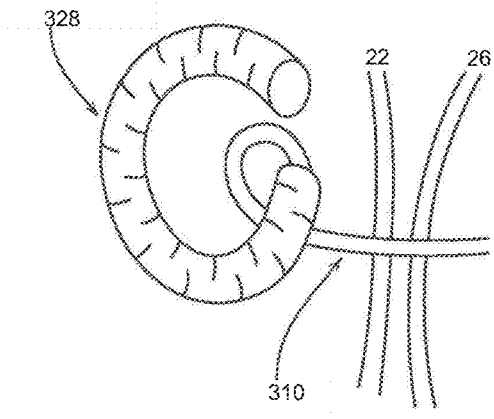
Figure 30D:
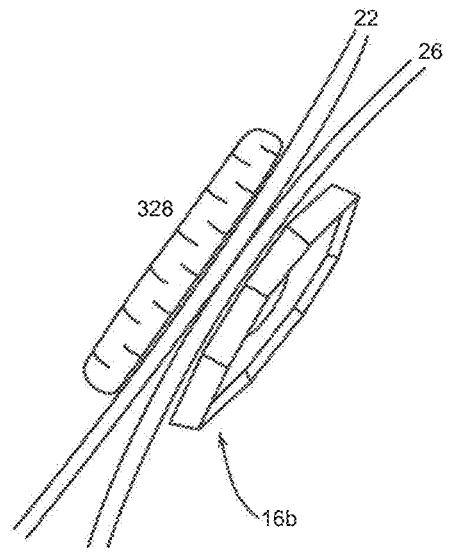

FIGS. 30A-30D illustrate a method of accessing the gallbladder 302, via endoscopic ultrasound guided access needle access 14, and delivering a magnetic coil or ring 328 configured to transition from a substantially linear shape to a substantially annular shape upon delivery into the gallbladder 302 and is configured to serve the distal anastomosis device 16a to correspondingly mate with a proximal magnetic anastomosis device 16b positioned on the other side to subsequently compress tissue there between to form an anastomosis. FIG. 30A illustrates a delivery device accessing the stomach 300 and deploying through the stomach tissue wall 26 into the gallbladder 302 a magnetic coil or ring 328 to serve as the distal anastomosis device 16b. FIG. 30B illustrates a close-up view of the magnetic coil or ring 328 in the annular and straight positions. The magnetic device 328 is loaded into the delivery device 14 in the straight position. Once deployed, the magnetic device 328 self-assembles into a coil or ring shape in order to serve as the distal magnetic anastomosis device. In some embodiments, the coil is a laser cut hypotube, allowing the magnetic device 328 to flex. FIG. 30C illustrates a hypotube magnetic device 328 being deployed into the gallbladder 302 by a nitinol or pig tail wire 310. The nitinol wire 310 pierces through the stomach tissue wall 26 into the gallbladder 302 to deliver the distal anastomosis device, in this embodiment a magnetic hypotube 328. FIG. 30D illustrates the proximal magnet 16b mating with the magnetic hypotube anastomosis device 328. Once deployed, the hypotube 328 self-assembles into an annular shape. Due to corresponding polarities in the proximal 16b and distal 328 magnets, the magnets mate and compress the tissue 22, 26 therebetween, thus forming an anastomosis.

Figure 31A:
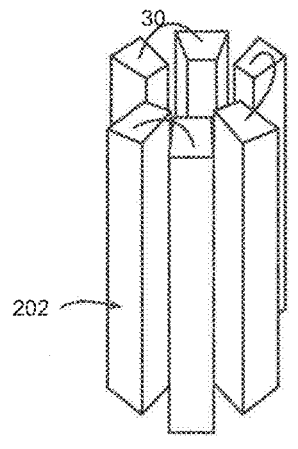
FIGS. 31A and 31B illustrate a set of magnetic segments prepackaged in an unstable polarity including a plurality of guide elements, tethers, or sutures coupling adjacent segments to one another to assist in self-assembly of the magnetic segments into a polygon deployed shape.
Figure 31B:
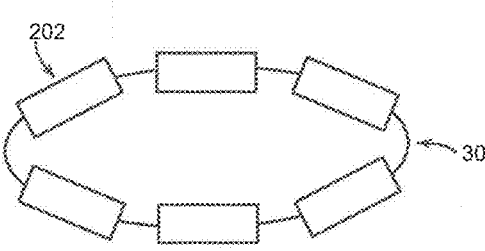

FIGS. 31A and 31B illustrate a set of magnetic segments 202 prepackaged in an unstable polarity including a plurality of guide elements 30, tethers, or sutures coupling adjacent segments to one another to assist in self-assembly of the magnetic segments 202 into a polygon deployed shape. FIG. 31B illustrates a self-assembled magnetic anastomosis device. Upon deployment from the delivery device 14, the magnetic anastomosis device 16 self-assembles into a polygon shape. The magnetic segments 200 are held in a polygon deployed shape by the guide elements 30, tethers, or sutures.

Figure 32A:
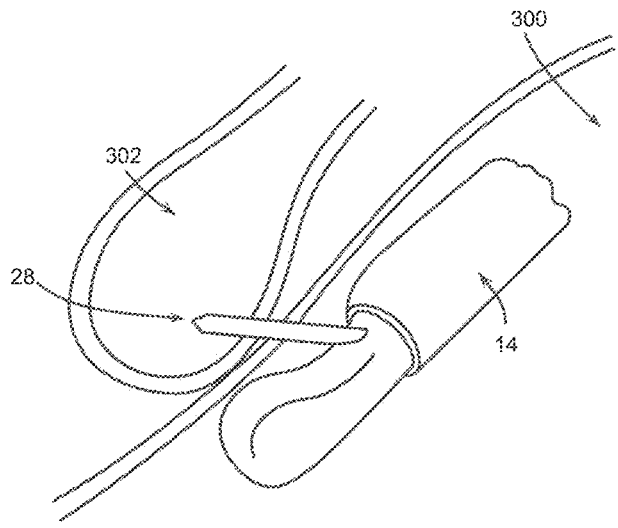
FIGS. 32A and 32B illustrate a method of accessing the gallbladder, via endoscopic ultrasound guided access and utilizing an access device having a conductor including a "hot" tip emitting monopolar energy, and subsequently delivering the prepackaged magnetic segments of FIGS. 31A and 31B into the gallbladder by way of a sheath.
Figure 32B:
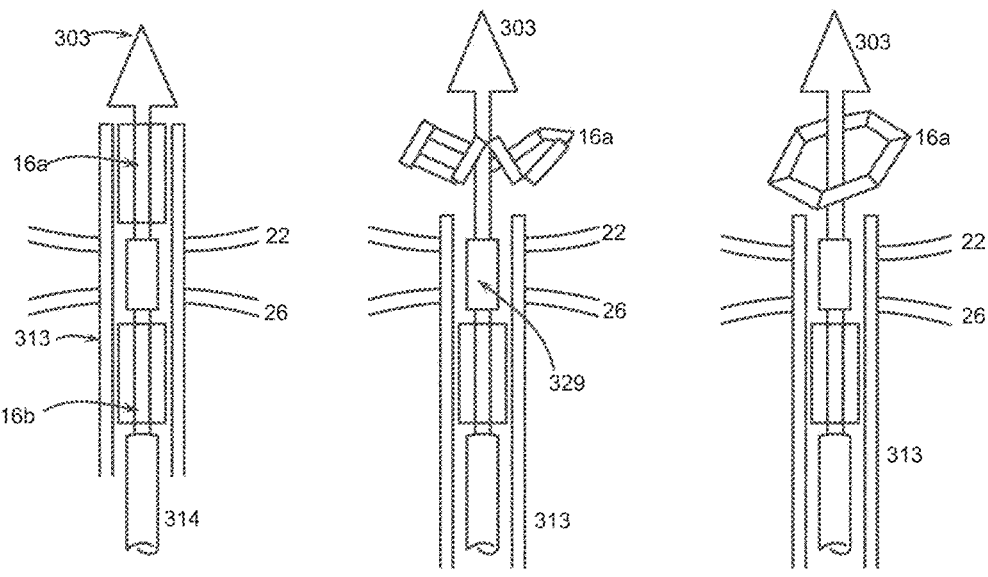

FIGS. 32A and 32B illustrate a method of accessing the gallbladder 302, via endoscopic ultrasound guided access 14 and utilizing an access device 28 having a conductor including a "hot" tip emitting monopolar energy 303, and subsequently delivering the prepackaged magnetic segments 202 of FIGS. 31A-31B into the gallbladder 302 by way of a sheath 313. FIG. 32A illustrates an EUS scope 14 guided into the stomach 300. The scope deploys a "hot" tip 303 that utilizes monopolar energy to pierce through the tissue 26 of the stomach and into the gallbladder 302 and therein delivery a magnetic anastomosis device 16a. FIG. 32B illustrates a close-up of the "hot" tip deployment mechanism 303. The "hot" tip utilizing monopolar energy 303 pierces the stomach tissue 26 into the gallbladder 302. The distal magnet 16a, a spacer 329 between the magnets, and a proximal magnet 16b are loaded into the sheath 313. By the user pulling back on the delivery device 14, the distal magnet 16a is deployed and self-assembles inside the gallbladder 302.

FIGS. 33A-33C illustrate a method of accessing the gallbladder 302, via endoscopic ultrasound guided access 14 and utilizing a needle 28 for access into the gallbladder 302, and subsequent delivery of a coiled stack of magnetic segments 202 configured to serve the distal anastomosis device 16a to correspondingly mate with a proximal magnetic anastomosis device 16b positioned on the other side to subsequently compress tissue there between to form an anastomosis. As shown in FIG. 33A, the nitinol coil is advanced into the gallbladder 302. The magnetic segments 202 are then advanced around the extended nitinol coil 310, as shown in FIG. 33B. Upon pulling a suture or guide wire 30, as shown in FIG. 33C, the magnetic segments 202 collapse upon one another (due to magnetic attraction forces) and form a coiled stack of magnets upon removal of the nitinol coil 310.

Figure 34A:
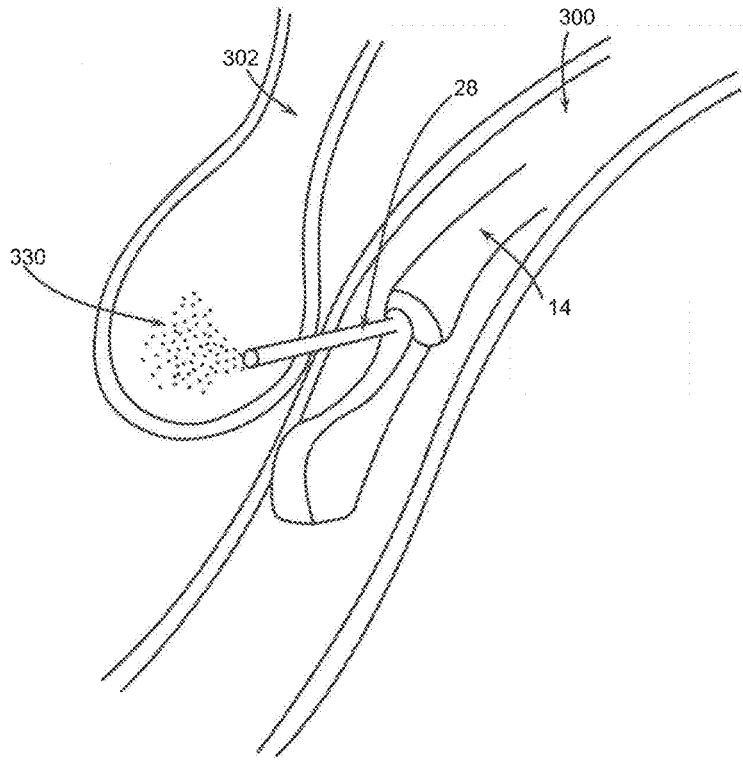
FIGS. 34A and 34B illustrate a technique of accessing the gallbladder and delivering a pair of magnetic anastomosis devices for the formation of an anastomosis the gallbladder tissue and adjacent tissue.
Figure 34B:
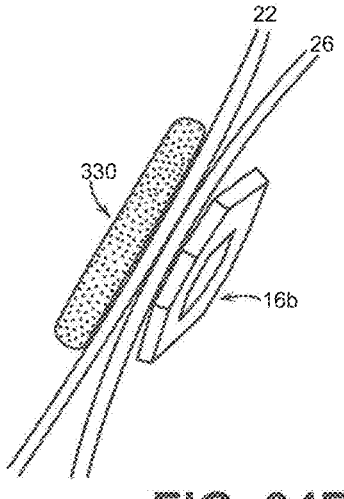

FIGS. 34A-34B illustrate a method of accessing the gallbladder 302, via endoscopic ultrasound guided access 14 and utilizing a needle 28 for access into the gallbladder 302, and subsequent delivery of a magnetic fluid 330 or suspension of magnetic particles into the gallbladder 302 configured to serve as the distal anastomosis device 16a to correspondingly mate with a proximal magnetic anastomosis device 16b positioned on the other side to subsequently compress tissue there between to form an anastomosis. FIG. 34A illustrates an EUS scope 14 accessing the stomach 300. An access needle 28 having piercing capabilities pierces the stomach tissue 26 into the gallbladder 302 to deliver magnetic fluid or particles 330 into the gallbladder 302. FIG. 34B illustrates that when in proximity to the proximal magnet 16b, the magnetic particles 330 will attract to the proximal magnet 16b, compressing the tissue 22, 26 between and therein forming an anastomosis.

Figure 35:
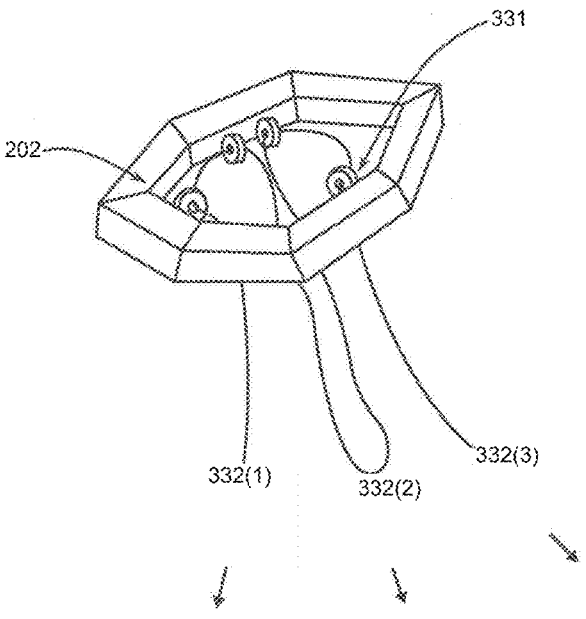
FIG. 35 illustrates a magnetic anastomosis device comprising a continuous guide element or suture that is coupled to a plurality of the magnetic segments of the device by way of eyelets positioned on each of the plurality of magnetic segments.

FIG. 35 illustrates a magnetic anastomosis device comprising a continuous guide element 30 or suture that is coupled to a plurality of the magnetic segments 202 of the device by way of eyelets 331 positioned on each of the plurality of magnetic segments 202. The magnets 16 have eyelets 331 on the inside circumference in order to prevent sutures from getting trapped or pinched between magnets. The guide elements 30 run through the eyelets 331 and have legs 332(1)-332(3) that can be pulled by the user either individually or simultaneously for manipulation of the magnet 16. Legs 332(1) or 332(3) may be pulled individually for removal of the guide elements 30.

Figure 36:
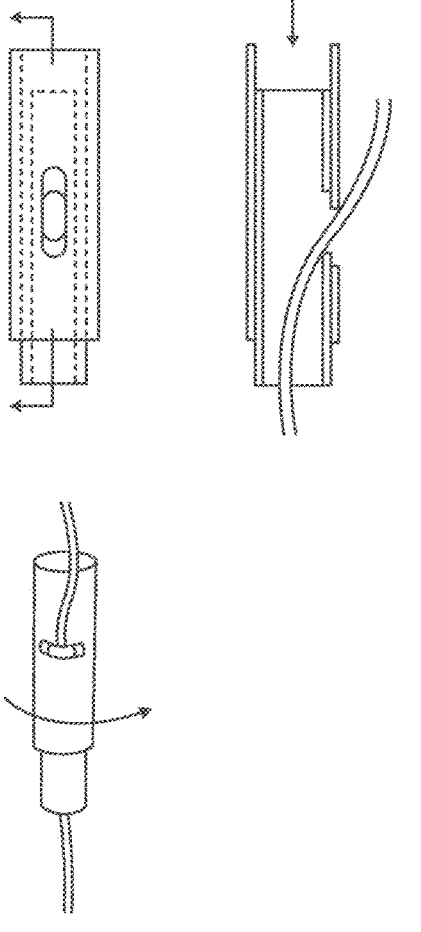
FIG. 36 illustrates one embodiment of a suture cutting arrangement within a deployment sheath of the delivery device, or a secondary device, for cutting the sutures coupled to the magnetic anastomosis devices.

FIG. 36 illustrates one embodiment of a suture cutting arrangement within a deployment sheath 313 of the delivery device 14, or a secondary device, for cutting the sutures 30 coupled to the magnetic anastomosis devices 16a, 16b. A push/pull guillotine utilizing an anvil/sharp or sharp/sharp configuration is used to cut the sutures 60. By pushing and pulling on the cutting arrangement, a knife edge is exposed. Pushing/pulling on the cutting arrangement also introduces tension to the sutures. The tensed sutures are pulled over the sharp edge of the cutting arrangement to be cut and subsequently removed from the cutting arrangement. In some embodiments, the cutting arrangement may be twisted to expose a knife edge to cut the sutures.

Figure 37A:
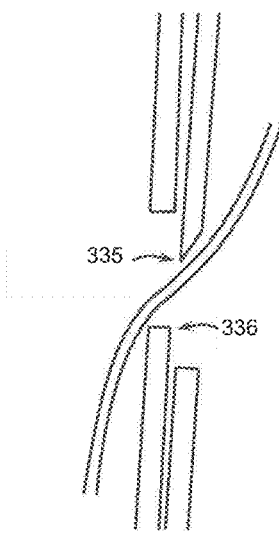
FIGS. 37A and 37B are enlarged side views illustrating an anvil/sharp arrangement and a sharp/sharp arrangement for cutting sutures.
Figure 37B:
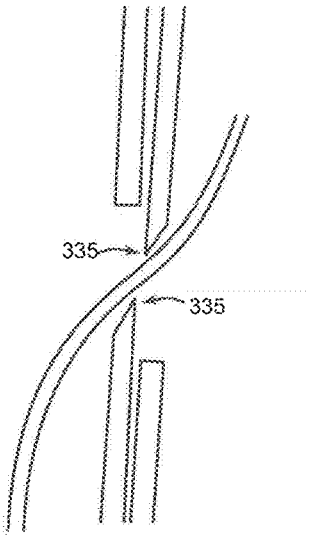

FIGS. 37A and 37B are enlarged side views illustrating an anvil/sharp arrangement and a sharp/sharp arrangement for cutting sutures. FIG. 37A illustrates a sharp 334/anvil 335 cutting arrangement. A tensed guide element 30 is brought over the exposed sharp edge 334 to be cut by pushing and pulling on the cutting arrangement. FIG. 37B illustrates a sharp/sharp cutting arrangement. By pushing and pulling on the cutting arrangement, two sharp edges 334 are exposed, cutting a tensed guide element 30.

Figure 38:
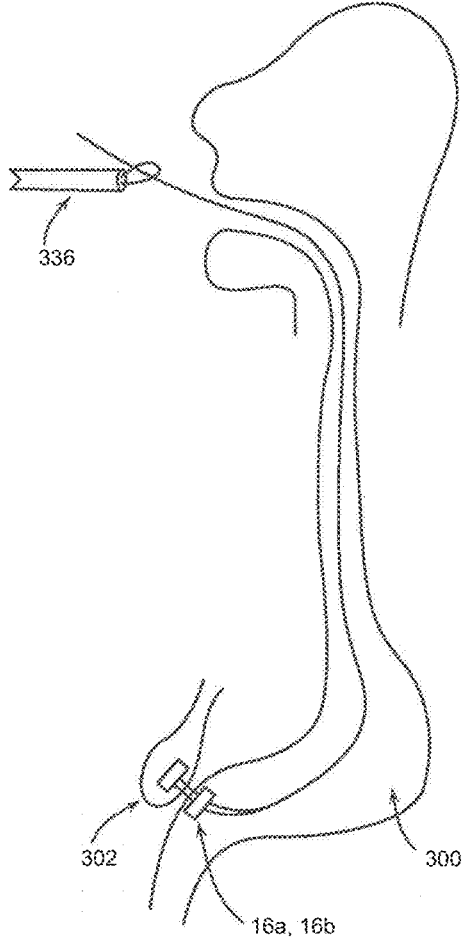
FIG. 38 illustrates a snare device (secondary device) configured to be inserted over the guide elements or sutures coupled to the magnetic anastomosis devices and configured to cut said sutures or guide elements once they have been deployed and positioned at a target site.

FIG. 38 illustrates a snare device 336 (secondary device) configured to be inserted over the guide elements 30 or sutures coupled to the magnetic anastomosis devices 16a, 16b and configured to cut said sutures or guide elements 30 once they have been deployed and positioned at a target site. A snare device 336 is advanced into the stomach 300 through an endoscope or similar delivery device 14. After the magnets 16a, 16b are positioned in the desired location to form an anastomosis, the snare device 336 is advanced over the guide elements 30 through a working channel of the scope 14. The snare device 336 cuts the guide elements 30, detaching them from the deployed magnetic anastomosis devices 16a, 16b.

Figure 39A:
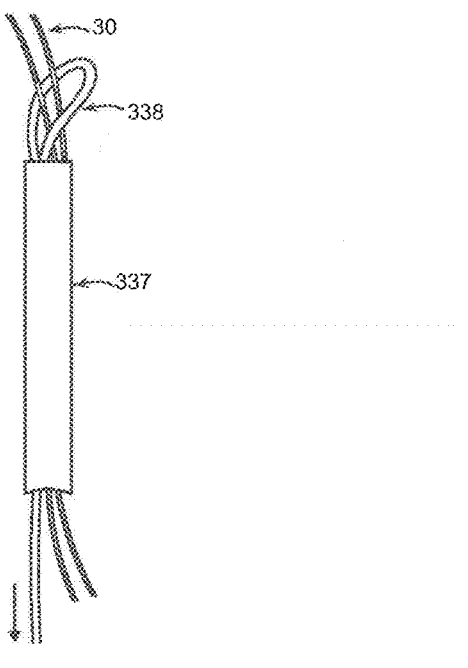
FIG. 39A illustrates a snare device comprising a resistive heating element for cutting guide elements.

FIG. 39A illustrates a snare device comprising a resistive heating element 338 for cutting guide elements 30. The snare member 336 comprises a support tube 337 that guides the snare device 336 into position to cut the guide elements 30. The resistive heating element 338 may be powered by low voltage from a battery or a generator. By pulling on the snare device 336, the resistive heating element 338 applies energy to and cuts the guide elements 30, releasing them from the magnetic anastomosis device 16 for subsequent removal.

Figure 39B:
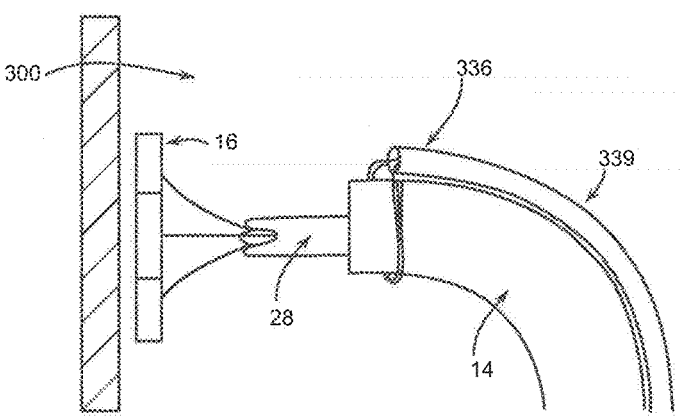
FIGS. 39B and 39C illustrate a snare device comprising a ring member having a cutting edge for cutting guide elements.
Figure 39C:
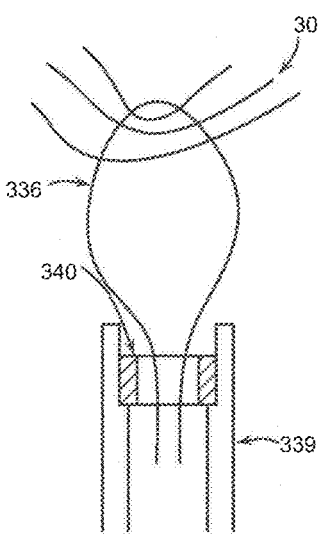
Figure 39D:
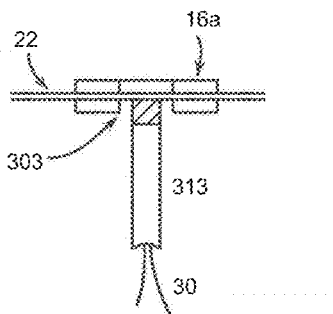
FIG. 39D illustrates a secondary device configured to provide suture or guide element cutting by way of monopolar/bipolar energy.

FIGS. 39B and 39C illustrate a snare device comprising a ring member having a cutting edge for cutting guide elements. FIG. 39D illustrates a secondary device configured to provide suture or guide element 30 cutting by way of monopolar/bipolar energy. FIG. 39B illustrates a close-up view of the snare device 336. The snare device 336 may be positioned on the outside of a scope 14 or incorporated into a cap on the scope 14. The snare device 336 is contained within a snare sleeve 339. A deployment means or delivery needle 28 deploys the magnet 16 into the stomach 300. The snare device 336 is advanced in the snare sleeve 339 as shown in FIG. 39C. FIG. 39C illustrates a snare device 336 comprising a ring member 340 having a cutting edge for cutting guide elements 30. The snare device 336 captures the guide elements 30 within the loop. By pulling back on the snare sleeve 339, the ring member 340 cuts the guide elements 30, detaching them from the magnets 16 for subsequent removal. FIG. 39D illustrates a secondary device configured to provide suture or guide element 30 cutting by way of monopolar/bipolar energy. Once the magnets 16a, 16b are in place on the tissues 22, 26, a monopolar/bipolar "hot" tip 303 is utilized to cut the guide elements 30. The monopolar or bipolar tip 303 is activated upon pulling back on the delivery device 14.

Figure 40:
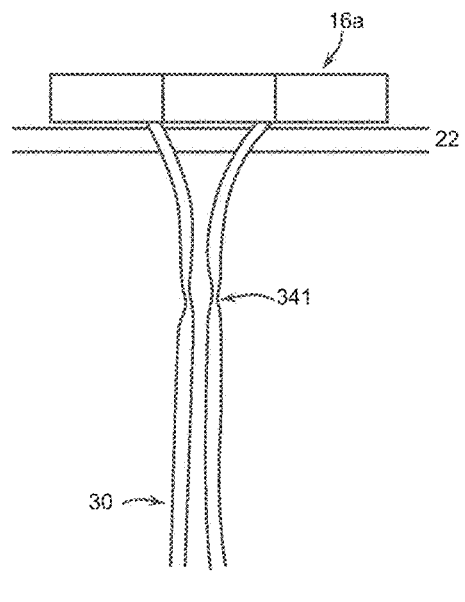
FIG. 40 illustrates breakaway guide elements or sutures.
Figures 41A, 41B:
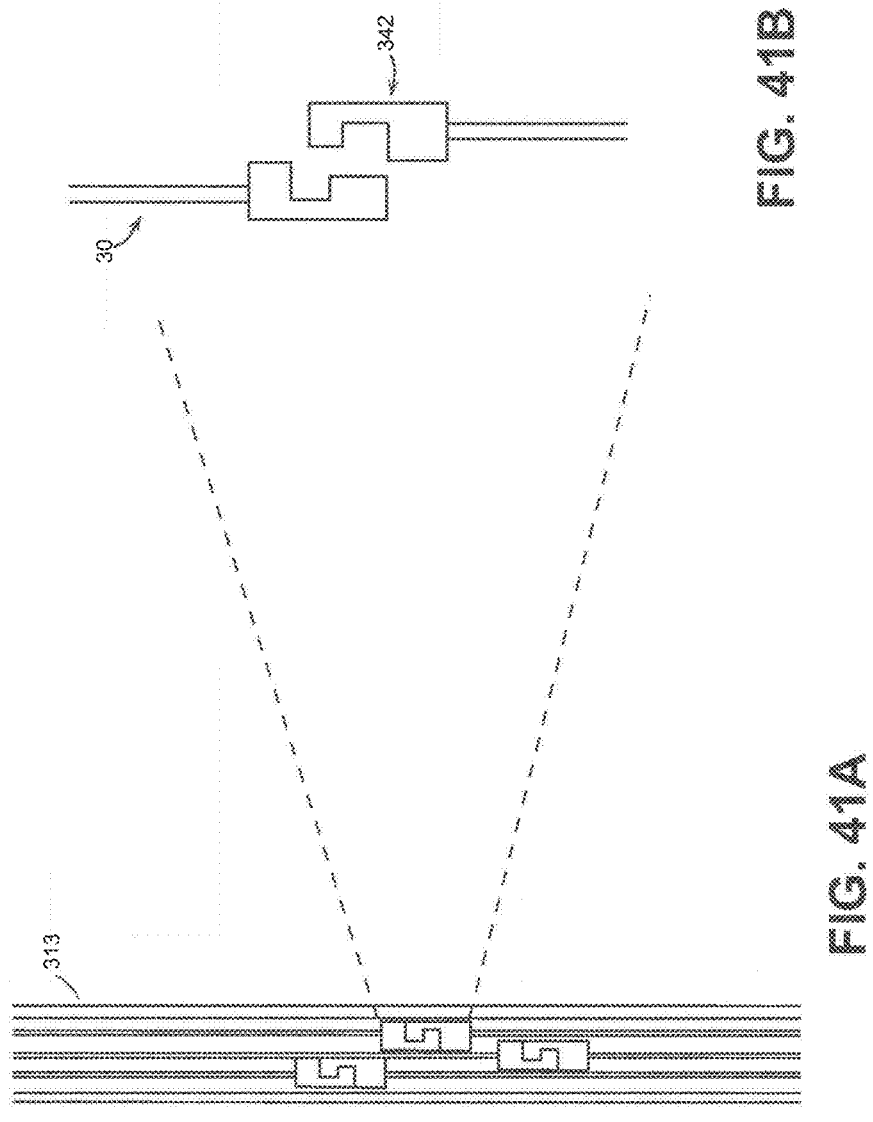
FIGS. 41A and 41B illustrate a detachable suture assembly.

FIG. 40 illustrates breakaway guide elements or sutures. FIGS. 41A and 41B illustrate a detachable suture assembly. The guide elements 30 comprise a necked down or weakened portion 341. Upon pulling back on the guide elements 30, the guide elements 30 break away at the weakened point 341, detaching from the magnetic assembly 16 for subsequent removal of the guide elements 30.

FIGS. 41A and 41B illustrate a detachable guide element 30 assembly. Within the sheath 313 of the delivery device 14, sutures comprising overmolded drivers 342 are stored in a staggered position as shown in FIG. 41A. In some embodiments, the guide elements 30 comprising overmolded drivers 342 may be stored in individual lumens. The overmolded drivers 342 are stored in a constrained position within the sheath 313. Upon deployment by removing the sheath 313, the overmolded drivers 342 are no longer constrained, and detach from one another, as shown in FIG. 41B. Upon the overmolded drivers 342 detaching, the guide elements 30 may be removed from the patient 12.

Accordingly, exemplary embodiments provide improved devices and techniques for minimally invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer. More specifically, exemplary embodiments provide various systems, devices, and methods for the delivery, deployment, and positioning of magnetic compression devices at a desired site so as to improve the accuracy of anastomoses creation between tissues, organs, or the like.

Figure 42:
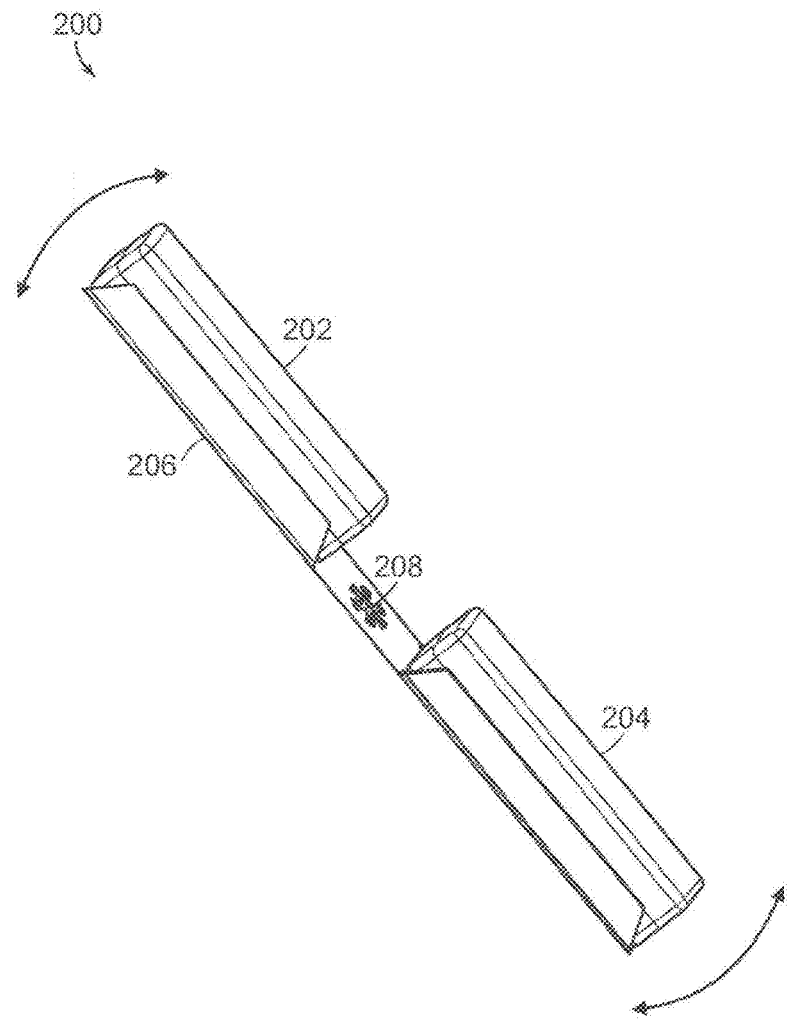
FIG. 42 illustrates a perspective view of another embodiment of a magnetic assembly consistent with the present disclosure.

FIG. 42 illustrates a perspective view of another embodiment of a magnetic assembly 200 consistent with the present disclosure. The magnetic assembly 200 comprises a pair of magnetic segments 202, 204 generally arranged in a linear alignment with one another (e.g., aligned in an end-to-end fashion) and coupled together via a flexible exoskeleton element 206. The segments 202, 204 are spaced apart via a central portion 108 of the exoskeleton 206. The central portion 208 may include a connection member for receiving a corresponding connection member of a placement device to assist in delivery of the magnetic assembly 200, as will be described in greater detail herein. The exoskeleton may be made from a resilient material that will retain its shape after deformation, such as a polymer or metal alloy. In some embodiments, the metal alloy will comprise nickel, such as nitinol. Exemplary exoskeleton embodiments are described in U.S. Pat. Nos. 8,870,898, 8,870,899, 9,763,664, the contents of each of which are incorporated by reference herein in their entirety.

The magnetic assembly 200 is configured to be delivered and deployed at a target site via a delivery device 100. As previously described, exemplary embodiments provide improved devices and techniques for minimally-invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer. More specifically, exemplary embodiments provide a system including a delivery device 100 for introducing and delivering, via a minimally-invasive technique, a pair of magnetic assemblies between adjacent organs to bridge walls of tissue of each organ together to thereby form a passage therebetween (i.e., an anastomosis). The delivery device 100 is particularly useful in delivering the pair of magnetic assemblies to a target site within the gastrointestinal tract to thereby form anastomosis between gastric and gallbladder walls to provide adequate drainage from the gallbladder when blockage is occurring (due to disease or other health-related issues).

FIGS. 43A-43I illustrate various steps in deploying a pair of magnetic assemblies 200a, 200b to a target site for subsequent formation of anastomosis. In the embodiments described herein, the system generally includes a single scope, such as an endoscope, laparoscope, catheter, trocar, or other access device, through which a delivery device is advanced to a target site for delivering and positioning a pair of magnetic assemblies 200a, 200b for subsequent formation of anastomosis at the target site. In particular, the delivery device 100 comprises an elongate hollow body 102, such as a catheter, shaped and/or sized to fit within the scope. The delivery device includes a working channel in which a pair of magnetic assemblies 200a, 200b is loaded. The delivery device further includes a distal end 104 configured to pierce, or otherwise penetrate, through tissue.

Figure 43A:
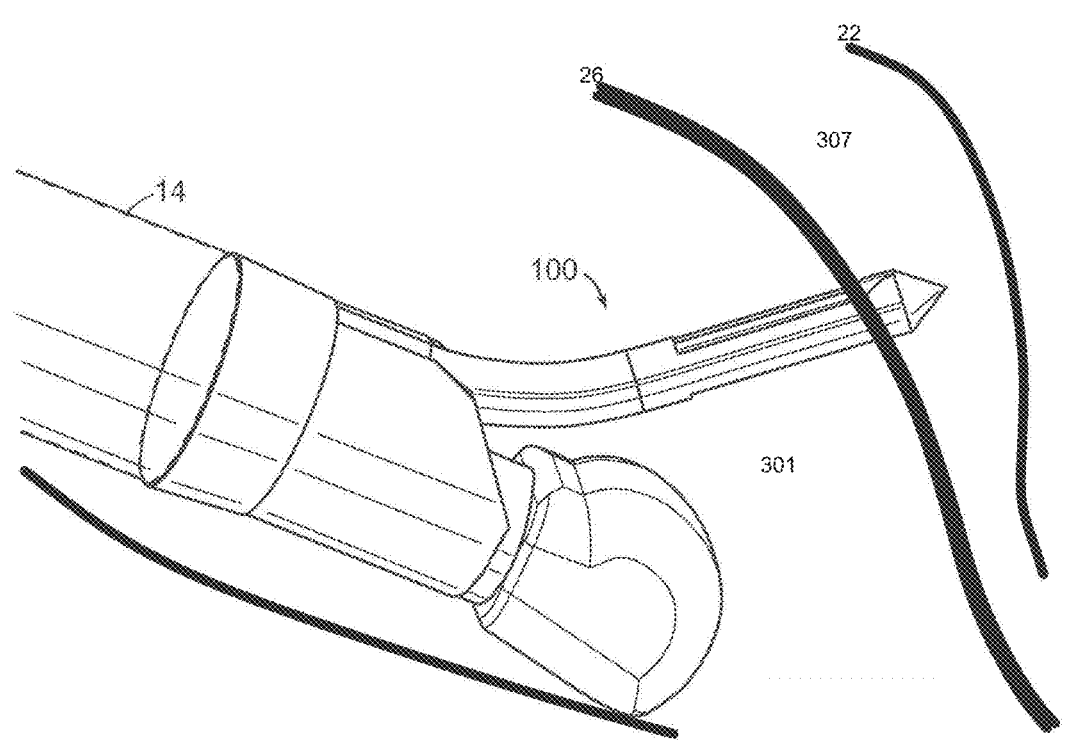
FIG. 43A illustrates advancement of a distal tip of a delivery device through respective tissue walls of adjacent organs at a target site for subsequent formation of an anastomosis therebetween.
Figure 43B:
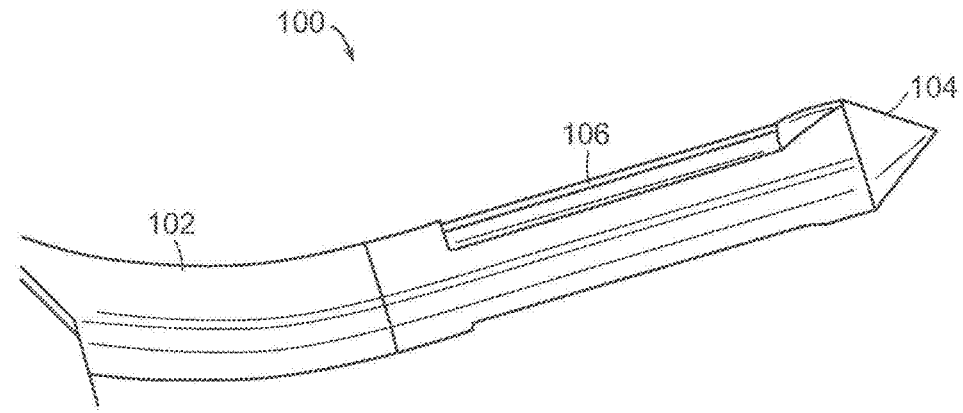
FIG. 43B is an enlarged view of a distal end of the delivery device illustrating the slot extending entirely through a side of the body of the delivery device.

For example, FIG. 43A illustrates advancement of a distal tip of a delivery device 100 through respective tissue walls 22, 26 of adjacent organs at a target site for subsequent formation of an anastomosis therebetween. For example, the distal end 104 may have a sharp tip for piercing tissue and/or may utilize energy to penetrate through tissue 26 (i.e., a hot tip). The body 102 of the delivery device 100 further includes a slot or opening 106 adjacent to the distal end 104, as shown in FIG. 43B. As shown, the slot extends entirely through a side of the body 102 of the delivery device 100. The slot 106 is shaped and/or sized to receive the magnetic assemblies 200a, 200b therethrough, such that the magnetic assemblies 200a, 200b pass through the working channel and exit the delivery device 100 via the slot 106. The delivery device 100 further includes a placement member 108, generally in the form of a wire or the like, that is releasably coupled to one or both of the magnetic assemblies 200a, 200b and provides a means of deploying the magnetic assemblies 200a, 200b from the distal end of the delivery device 100 via the slot 106.

Figure 43C:
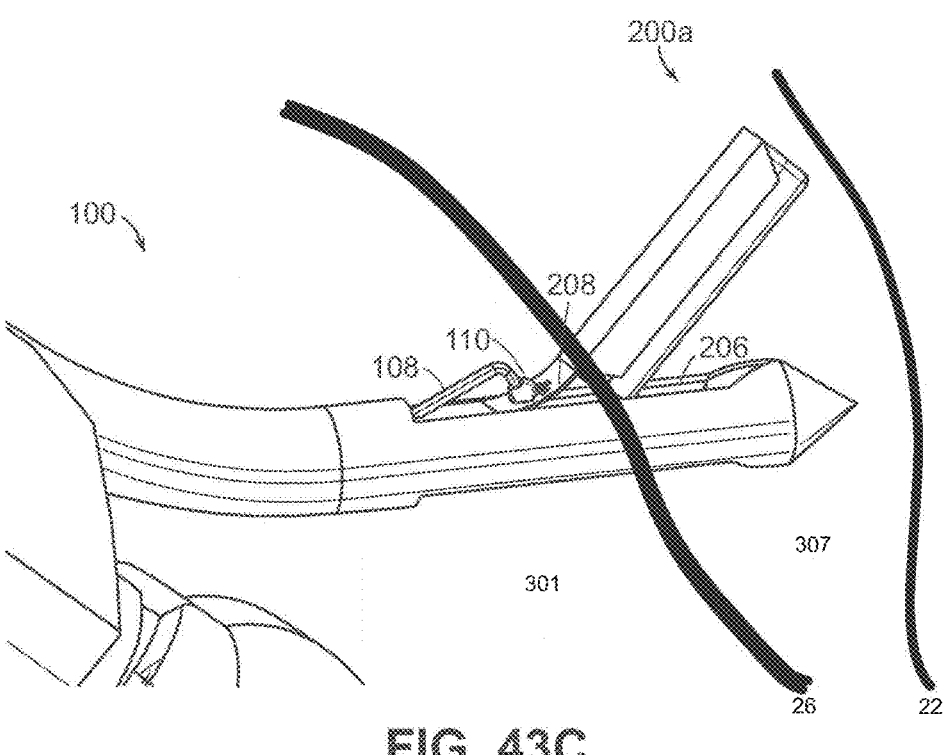
FIG. 43C illustrates delivery of a first magnetic assembly into a first organ.
Figure 43D:
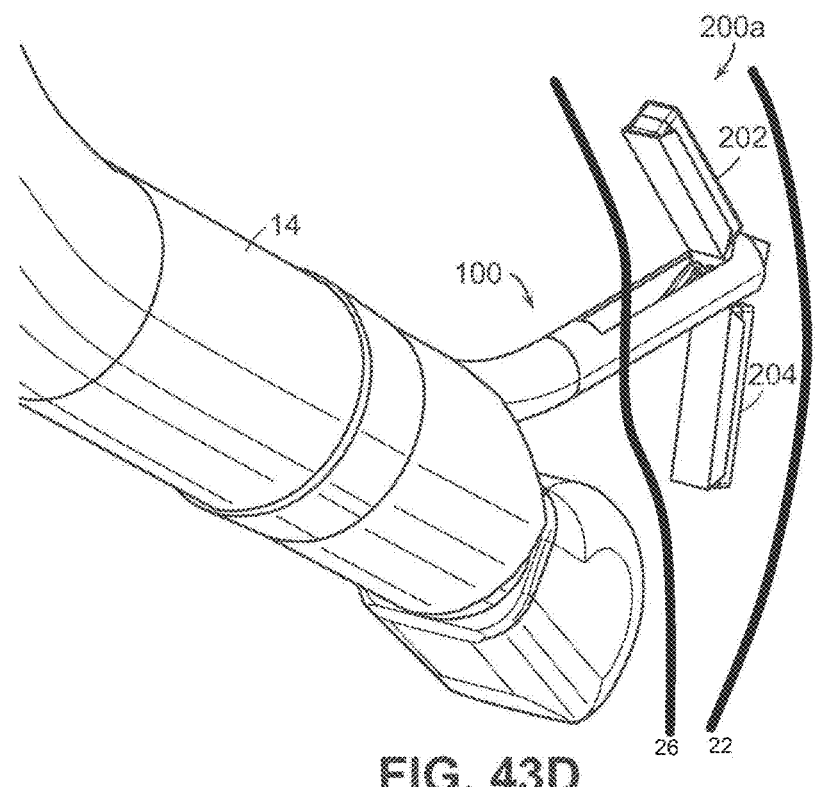
FIG. 43D illustrates deployment of the first magnetic assembly into the first organ while remaining retained within the slot of the delivery device.

During a procedure, a surgeon or other trained medical professional may advance a scope (e.g., endoscope) within a hollow body of the patient and position the scope at a desired anatomical location for formation of the anastomosis based on either a visual depiction of the location of the target site as provided by an imaging modality 18 providing a medical imaging procedure (e.g., ultrasound (US), wavelength detection, X-ray-based imaging, illumination, computed tomography (CT), radiography, and fluoroscopy, or a combination thereof). The surgeon may advance the distal tip 104 of the delivery device 100 through adjacent walls of a pair of organs (i.e., through a wall of the duodenum and a wall of the common bile duct), in any manner previously described herein. Upon advancing distal end 104, including the slot 106, into the first organ (i.e., common bile duct), the surgeon may utilize the placement member 108 to manually deliver and deploy a first magnetic assembly 200a into the first organ via the slot. For example, FIG. 43C illustrates delivery of a first magnetic assembly 200a into the common bile duct. As shown, the placement member 108 include a connection member 110 at a distal end of the placement member 108, which is configured to be releasably coupled to a corresponding connection member of the central portion 208 of the exoskeleton 206 (indicated by attachment point arrow). Upon advancing and extending the placement member 108 towards the distal end 104 of the delivery device 100, the first magnetic assembly passes from the working channel of the delivery device 100 and through the slot 106 to transition into a deployed state, as illustrated in FIG. 43D. As shown, deployment of the first magnetic assembly 200a results in the pair of magnetic segments 202, 204 to exit the slot 106 on opposite respective sides of the body 102 of the delivery device 100 while the central portion 208 of the exoskeleton 206 remains within the slot 106. In other words, the slot 106 extends entirely through the body 102 of the delivery device 100, from one side to the other. Accordingly, when in a deployed state, the first magnetic assembly 200a is positioned into the first organ while remaining retained within the slot 106 of the delivery device 100.

Figure 43E:
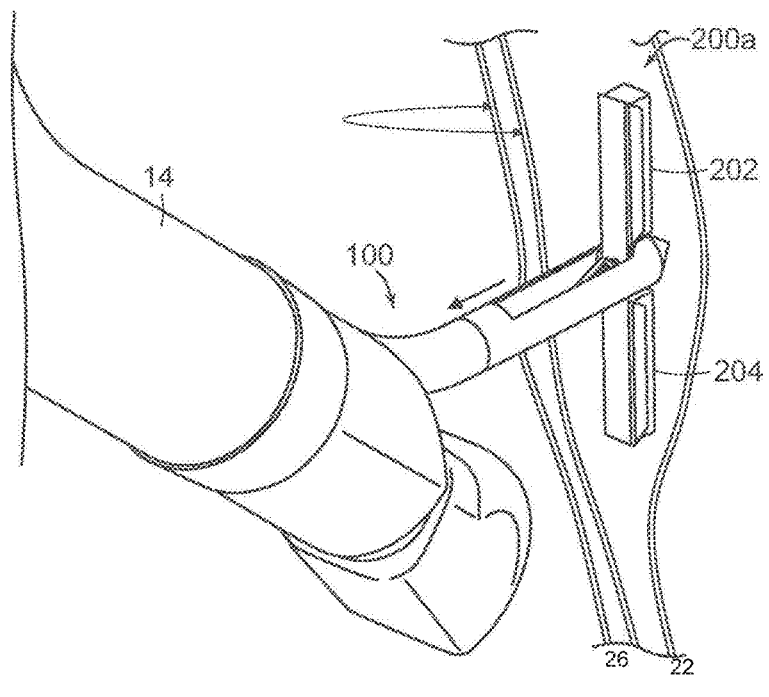
FIG. 43E illustrates a fully deployed first magnetic assembly within the first organ and pulling back of the delivery device to thereby draw the first magnetic assembly against a wall of the first organ in preparation for delivery and deployment of the second magnetic assembly in the second organ.

At this point, the surgeon need only pull back upon the delivery device 100 until the first magnetic assembly 200a engages the tissue of the first organ and the majority of the slot 106 is positioned within the second organ. The surgeon is able to then deliver and deploy the second magnetic assembly 200*b* into the second organ (i.e., the duodenum). FIG. 43E illustrates a fully deployed first magnetic assembly 200*a* within the first organ and pulling back of the delivery device 100 to thereby draw the first magnetic assembly 200*a* against a wall of the common bile duct in preparation for delivery and deployment of the second magnetic assembly 200*b* in the duodenum.

Figure 43F:
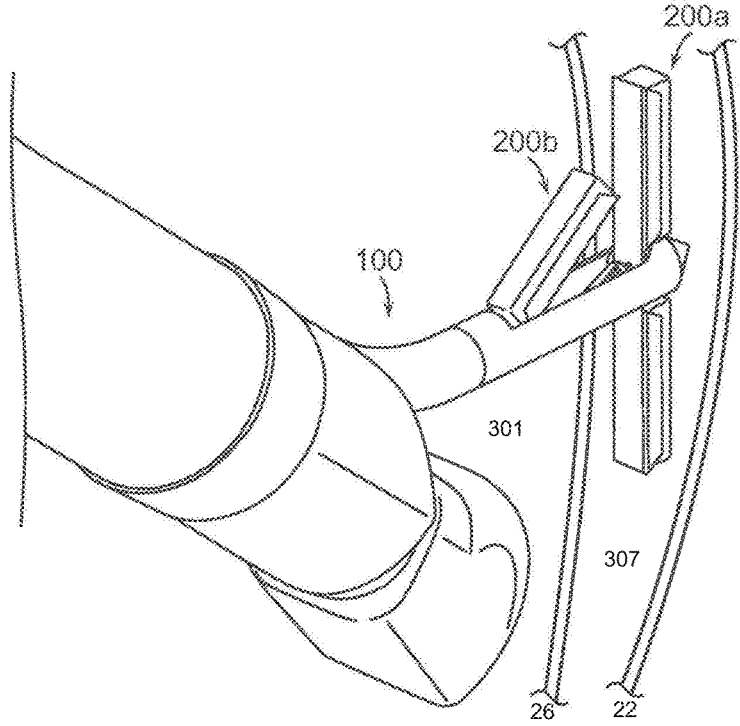
FIG. 43F illustrates delivery of the second magnetic assembly into the second organ.
Figure 43G:
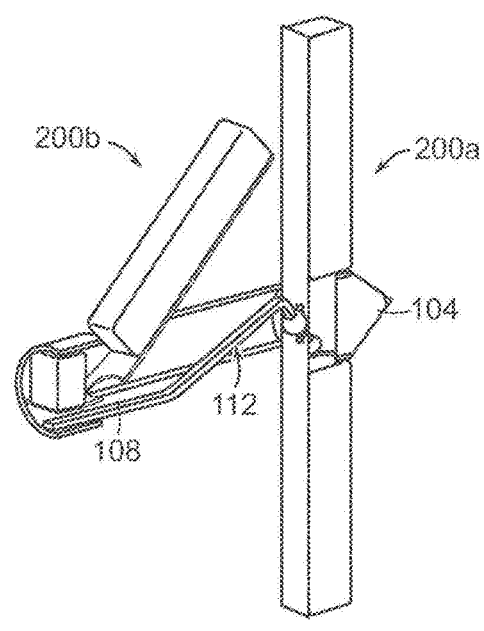
FIG. 43G is an enlarged view, partly in section, of the second magnetic assembly advancing to a deployed state.
Figure 43H:
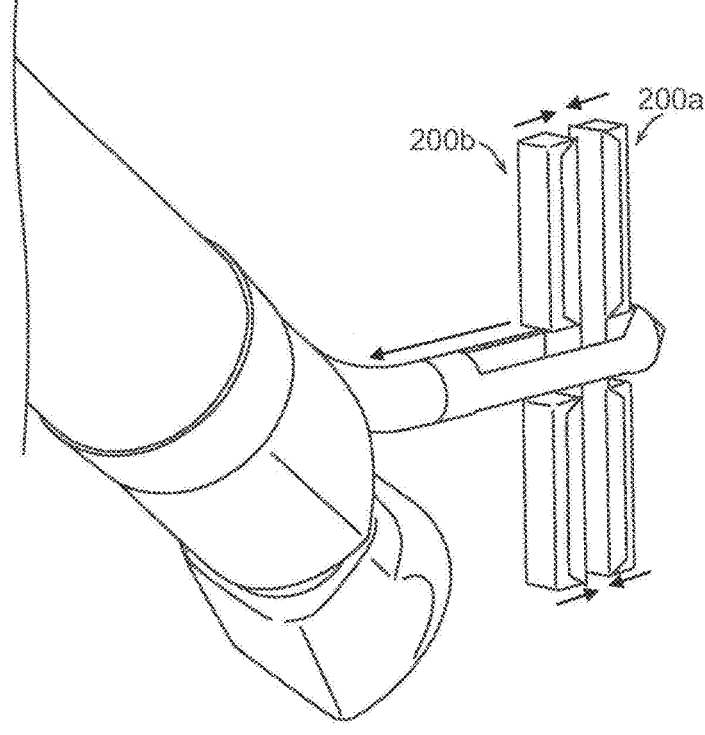
FIG. 43H illustrates the first and second magnetic assemblies in fully deployed states and coupled to one another as a result of attractive magnetic forces therebetween.

The second magnetic assembly 200*b* deploys in a similar fashion as the first magnetic assembly 200*a*, in that magnetic segments 202, 204 of the second magnetic assembly 200*b* exit the slot 106 on opposite respective sides of the body 102 of the delivery device 100 while a central portion 208 of an exoskeleton 206 remains retained within the slot 106. FIG. 43F illustrates delivery of the second magnetic assembly 200*b* into the duodenum. FIG. 43G is an enlarged view, partly in section, of the second magnetic assembly 200*b* advancing to a deployed state. As shown, as the second magnetic assembly 200*b* is advanced through the working channel and towards the slot 106, the assembly 200*b* is configured to engage a ramped section 112 of the placement member which assisted in directing at least one of the segments of the assembly 200*b* into place, as shown. FIG. 43H illustrates the first and second magnetic assemblies 200*a*, 200*b* in fully deployed states. The first and second magnetic assemblies 200*a*, 200*b* are substantially aligned with one another and, due to attractive magnetic forces, the first and second magnetic assemblies 200*a*, 200*b* will couple to one another.

Figure 43I:
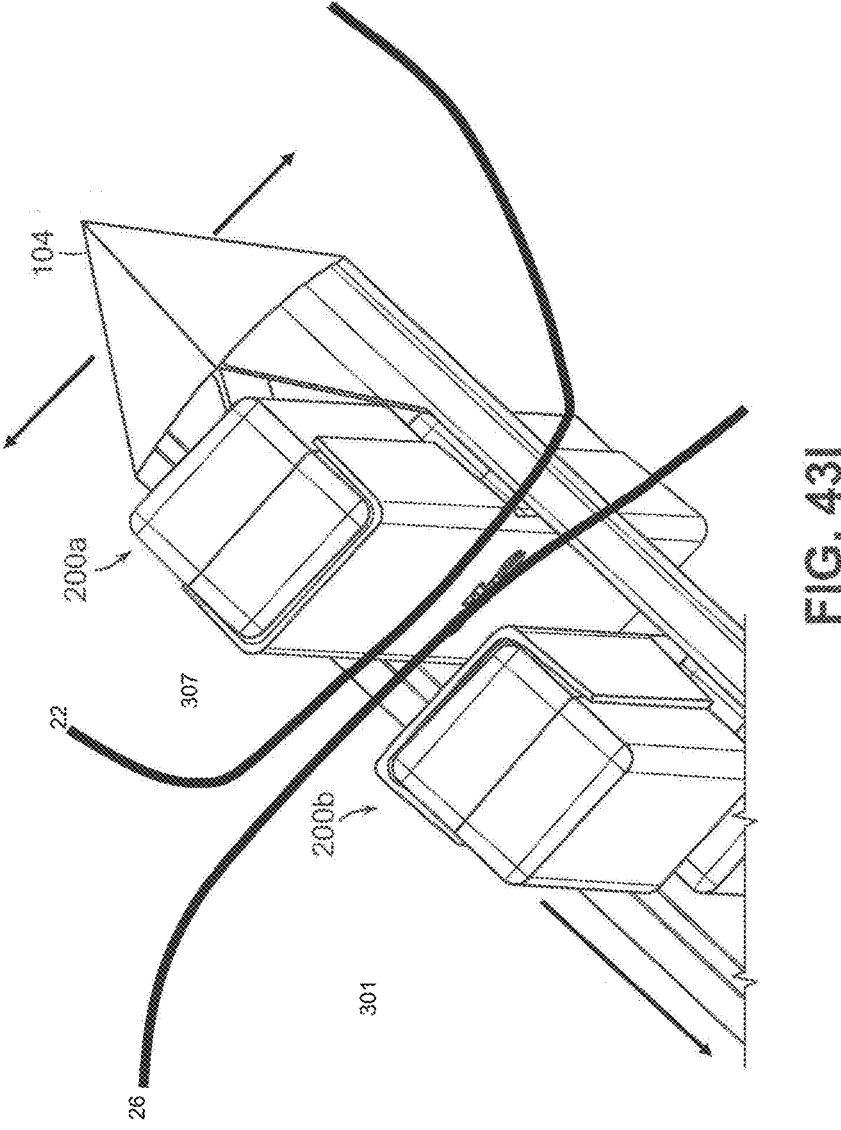
FIG. 43I illustrates the distal end of the delivery device constructed from two halves and configured to split apart to allow the delivery device to be removed from the target site while the pair of magnetic assemblies remain coupled to one another to form anastomosis at the target site.
Figure 44A:
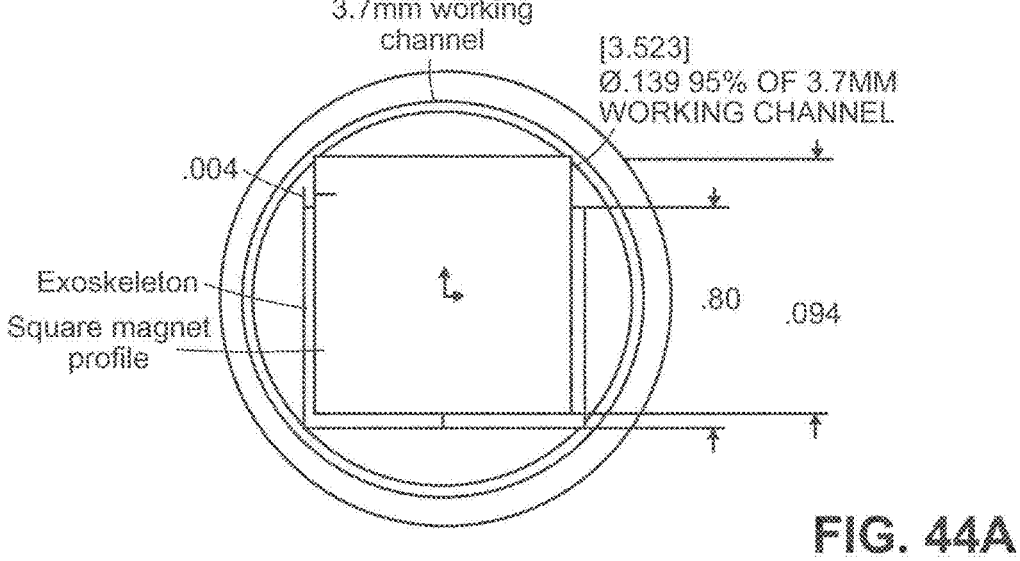
FIGS. 44A, 44B, 44C, and 44D are cross-sectional views of various profiles of magnet segments of magnetic assemblies within a working channel of a standard scope.
Figure 44B:
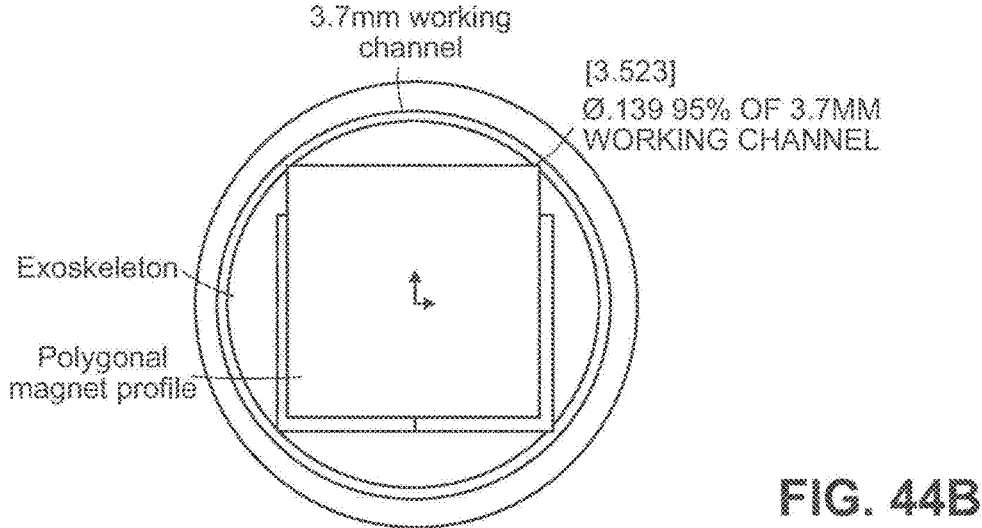
Figure 44C:
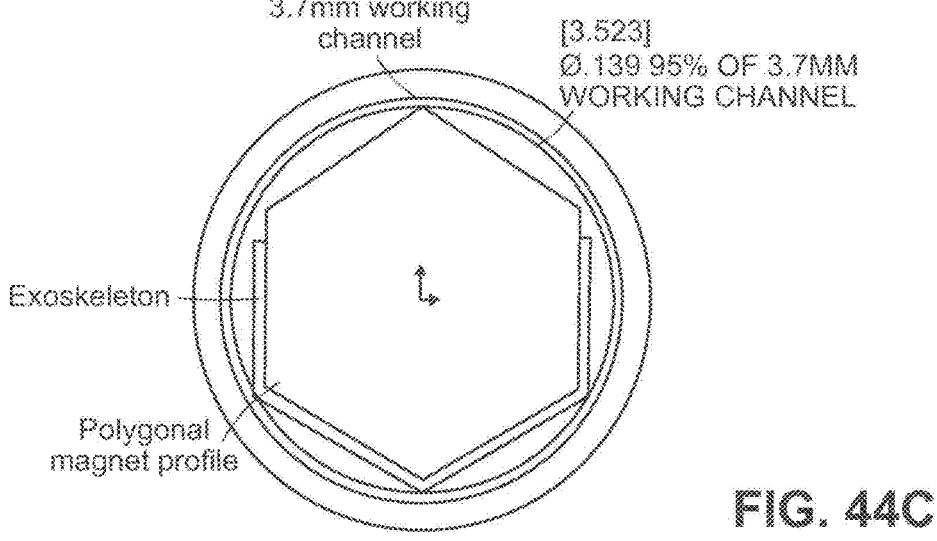
Figure 44D:
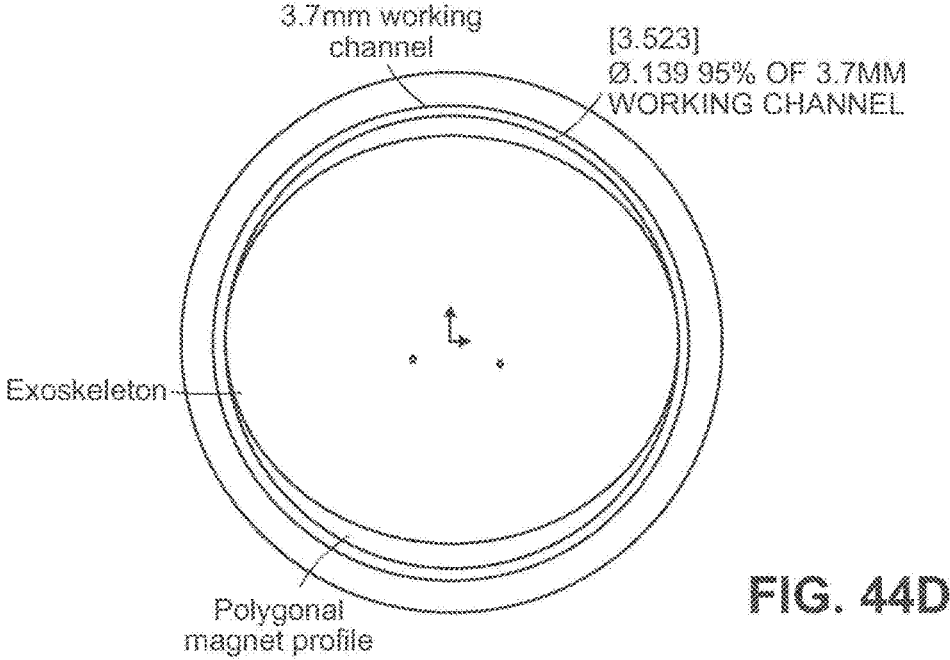

As shown in FIG. 43I, the distal end 104 of the delivery device 100 is comprised of two halves that, when in a default state, form a relatively uniform tip shape. However, the distal end comprises a deformable material (i.e., shape memory material), such that, upon application of sufficient force, the two halves will split apart. As such, once both the first and second magnetic assemblies 200*a*, 200*b* have been delivered and are effectively coupled to one another (but are still retained within the slot 106), the surgeon need only pull back on the delivery device 100 which then causes the magnetic assemblies 200*a*, 200*b* to make contact with the distal end 104 and force the two halves of the distal end 104 to split apart, allowing the distal end of the delivery device to be withdrawn from the target site while the pair of magnetic assemblies 200*a*, 200*b* remain in place. The pair of magnetic assemblies 200*a*, 200*b* compress the walls of each respective organ therebetween, subsequently forming an anastomosis between the organs (i.e., anastomosis between the duodenum and the common bile duct).

Upon deployment, each magnetic assembly has a width and a length generally corresponding to a width of a respective segment and a length that is approximately twice the length of each segment. As a result, the pair of magnetic assemblies, when coupled to one another, generally form a substantially linear package and the resulting anastomosis formed may generally be rectangular in shape, but may naturally form a round or oval shape. The resulting anastomosis may have a 1:1 aspect ratio relative to the dimensions of the magnetic assemblies. However, exemplary embodiments allow for larger aspect ratios (i.e., a larger anastomosis to form relative to the dimensions of the magnetic assemblies). In particular, prior art systems and methods that include the use of magnets for creating anastomosis are generally limited based on the dimensions of the working channel of the scope or catheter used for delivering such magnets, which, in turn, limits the resulting size of the anastomosis. The magnetic assembly design overcomes such limitations.

For example, the design of the magnetic assembly, notably the coupling of multiple magnetic segments to one another via an exoskeleton, allow for any number of segments to be included in a single assembly, and thus the resulting anastomosis has a greater size relative to the dimensions of the working channel of the scope. For example, in some embodiments, the resulting anastomosis may include an aspect ratio in the range of 2:1 to 10:1 or greater.

FIGS. 44A-44D are cross-sectional views of various profiles of magnet segments of magnetic assemblies within a working channel of a standard scope. The cross-sectional areas of magnets are illustrated, showing polygons as well as ellipses and circles taking between 10 and 95 percent of the annular space of the working channel. With the guidelines for the magnetic profile being in place, the next constraint for the device is the axial ratio of a minimum of 6:1 and a maximum of 50:1. This segmented length once assembled in the body can have either a regular or irregular shape.

FIG. 45 provides a listing of some exemplary working channel sizes considered usable/feasible to deploy a magnetic array with a cage to produce an anastomosis. These sizes do not limit future capabilities as scope channel sizes increase/decrease with market and device changes. The summary of sizing can be summarized into: 1.0 mm-6.0 mm (including a bleed scope called the "clot buster") with one particular sized device designed around the 3.7 mm.

Accordingly, the delivery device of the present disclosure produces a low-profile linear anastomosis that would allow certain complications, particularly those associated with blockage of the common bile duct, to be mitigated. In particular, patients experiencing a blockage of the common bile duct often undergo some sort of procedure to either remove the blockage or allow drainage to provide relief of jaundice/infection and hepatic portal complications. A common procedure is a sphincterotomy, or some sort of draining stent placement procedure. There are procedures which present decompression of the bile duct in a traditional way, but are not possible in a minimally noninvasive manner. Such procedures include, for example, a sphincterotomy, which is not possible due to inability to cannulate the common bile duct, inability to account for anatomical alterations, particularly when during heavily diseased states. Utilizing the magnetic closure force profile as described herein would allow minimal bleeding and create a semi-permanent slit profile. This slit profile would help to resist "sump syndrome" and help to create a drainage point which would remain effectively infection free.

In the GI tract, there are a multitude of tissue thicknesses that surgeons may encounter; up to 5 mm in the stomach, 3 mm in the jejunum and ileum, 4 mm in the duodenum, and 8 mm in the colon. These varying tissue thicknesses affect how surgeons create anastomoses throughout the GI tract. For example, thick tissue can limit the surgical procedure. In terms of magnetic compression anastomosis, thicker tissue can restrict two magnetic polygon assemblies from sensing (attracting) each other at these larger distances.

Therefore, certain exemplary embodiments utilize field controlled magnetic arrays 343 (FCMA) formed from smaller magnetic segments 344 (SMS). Such FCMAs 343 can enhance and/or redirect the magnetic field in a particular direction that allows the magnets 16*a*, 16*b* to sense one another at a greater distance. In some instances, a Halbach array can be used to enhance the surface field strength in one direction and essentially cancel it in the opposite direction. Among other things, this ultimately can give the surgeon more options for choosing the optimal landing/coupling location for the anastomosis to occur.

In some embodiments, each FCMA 343 comprising multiple SMSs 344 can be secured to a larger magnetic structure 345 such as a magnetic compression anastomosis device 16 or an individual magnetic segment 202 for a magnetic compression anastomosis device 16. For example, the larger magnetic structure 345 can include a pocket 346 or other receptacle to receive and secure the FCMA 343 or the individual SMSs 344 associated with the FCMA 343. As discussed above, multiple magnetic segments 202 can be assembled (e.g., self-assembled) to form a polygon or other shaped assembly that is used to enhance magnetic compression anastomosis. These FCMAs 343 can allow the magnetic compression anastomosis device 16 to sense another polygon assembly at a greater distance.

Figure 46A:
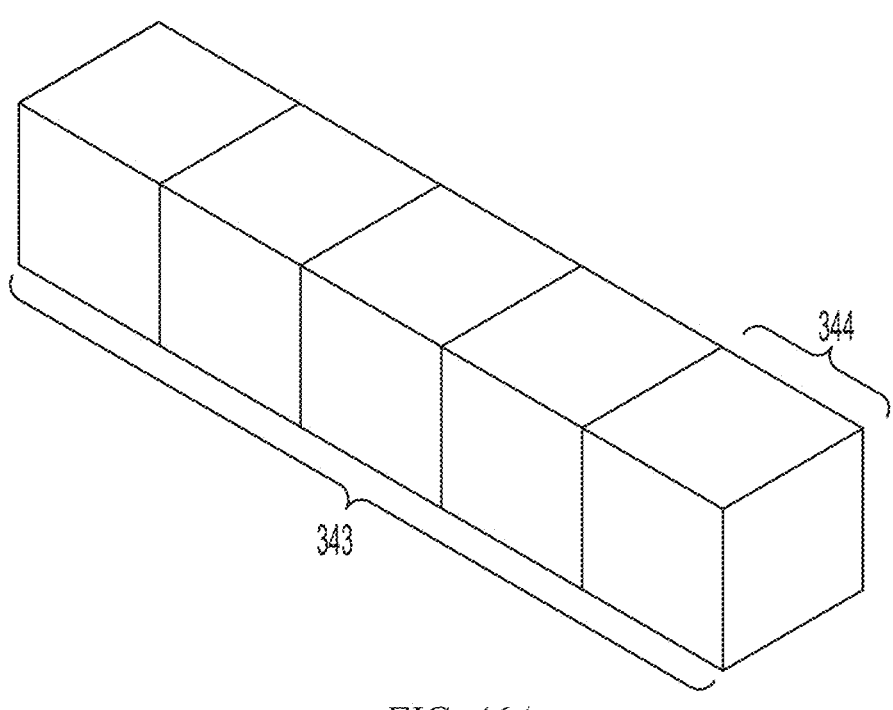
FIG. 46A is a schematic diagram showing a plurality of smaller magnetic segments (SMS) forming a field controlled magnetic array (FCMA), in accordance with certain exemplary embodiments.

FIG. 46A is a schematic diagram showing a plurality of smaller magnetic segments 344 (SMS) forming a field controlled magnetic array 343 (FCMA), in accordance with certain exemplary embodiments. It should be noted that the configuration shown in FIG. 46A is an example of a simple linear ("SL") configuration of SMSs 344 in which the SMSs 344 are linearly aligned, although it should be noted embodiments are not limited to linear configurations and alternative embodiments can accommodate other configurations, e.g., curved configurations such as might be formed from trapezoidally-shaped SMSs 344. Also, it should be noted that SMSs 344 can have square, rectangular, trapezoidal, circular, or other cross-sectional shapes.

Figure 46B:
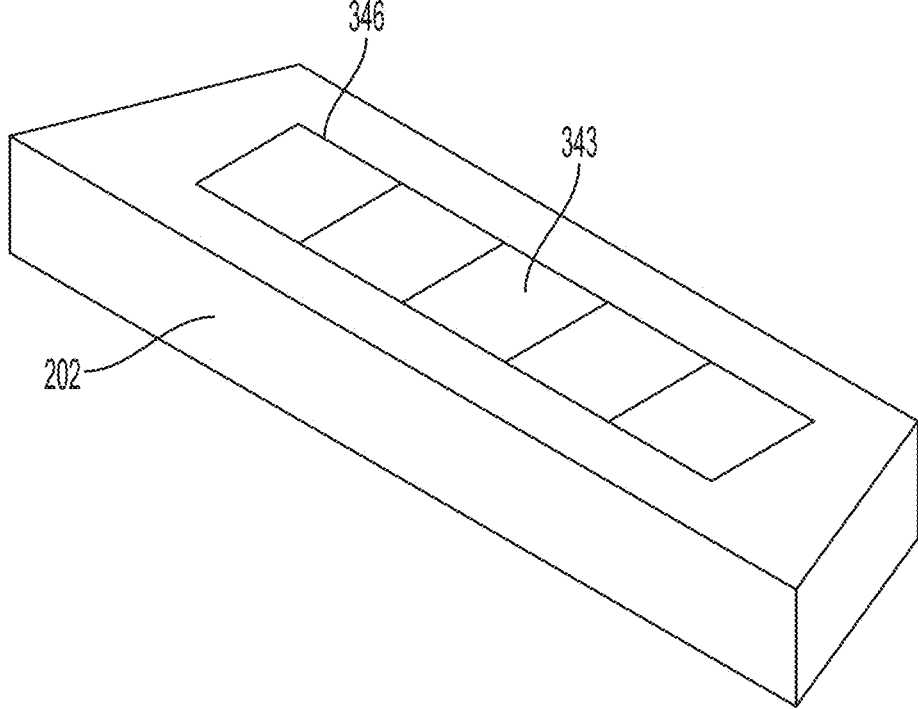
FIG. 46B is a schematic diagram showing a field controlled magnetic array (FCMA) situated in a pocket of an individual magnetic segment for a larger magnetic structure such as a magnetic compression anastomosis device, in accordance with certain exemplary embodiments.

FIG. 46B is a schematic diagram showing a field controlled magnetic array 343 (FCMA) situated in a pocket 346 of an individual magnetic segment 202 for a larger magnetic structure such as a magnetic compression anastomosis device 16, in accordance with certain exemplary embodiments.

Figure 46C:
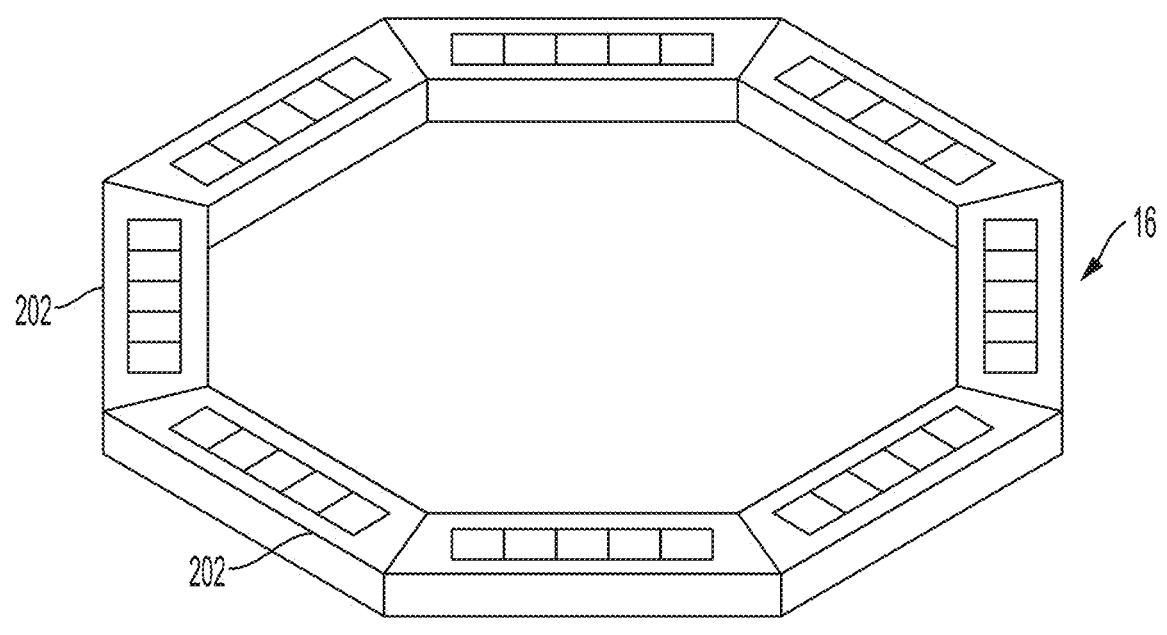
FIG. 46C is a schematic diagram showing a number of individual magnetic segments 200 with FCMAs assembled into a larger magnetic structure such as a magnetic compression anastomosis device shaped as a polygon (e.g., an octagon in this example), in accordance with certain exemplary embodiments.

FIG. 46C is a schematic diagram showing a number of individual magnetic segments 202 with FCMAs 343 assembled into a larger magnetic structure 16 such as a magnetic compression anastomosis device shaped as a polygon (e.g., an octagon in this example), in accordance with certain exemplary embodiments.

Figure 46D:
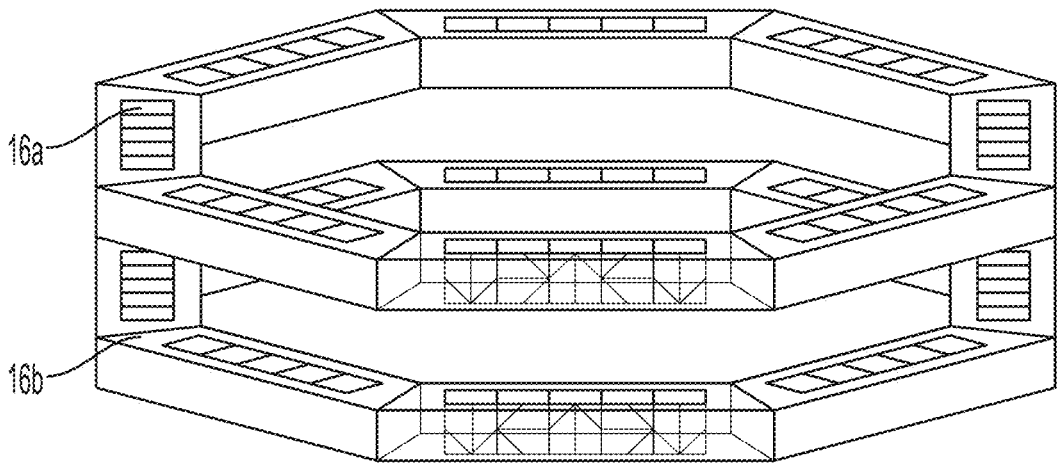
FIG. 46D is a schematic diagram showing the concept of two mating polygon assemblies and with instances of opposite polar configurations, in accordance with certain exemplary embodiments.

FIG. 46D is a schematic diagram showing the concept of two mating polygon assemblies 16a, 16b with instances of opposite polar configurations, in accordance with certain exemplary embodiments. Here, corresponding segments 202 of the two mating polygon assemblies 300 and 300' are shown in a see-through view to show the locations and magnetic orientations of the component SMSs 344 (e.g., with the arrows pointing to the north poles of the SMSs 344).

The small magnetic segments 344 may be oriented in various polar configurations, e.g., in order to reorient and strengthen the surface field of the field controlled magnetic array in one particular direction while optionally reducing or eliminating the surface field on its opposing side. These small magnetic segments 344 that form these arrays may be comprised of magnets that vary in size, shape, and/or strength to assist in redirecting the overall surface field strength.

In some embodiments, the mating magnetic polygon assembly to which the above-described assembly couples also can include small magnetic segments 344 forming field controlled magnetic arrays 343, for example, with the two mating assemblies having FCMAs 343 oriented in opposite polar configurations in order to improve mating of the two assemblies 16a, 16b. In other embodiments, a ferrous steel assembly can be used as the mating assembly in order to allow the two assemblies to couple and create an anastomosis.

Figure 47:
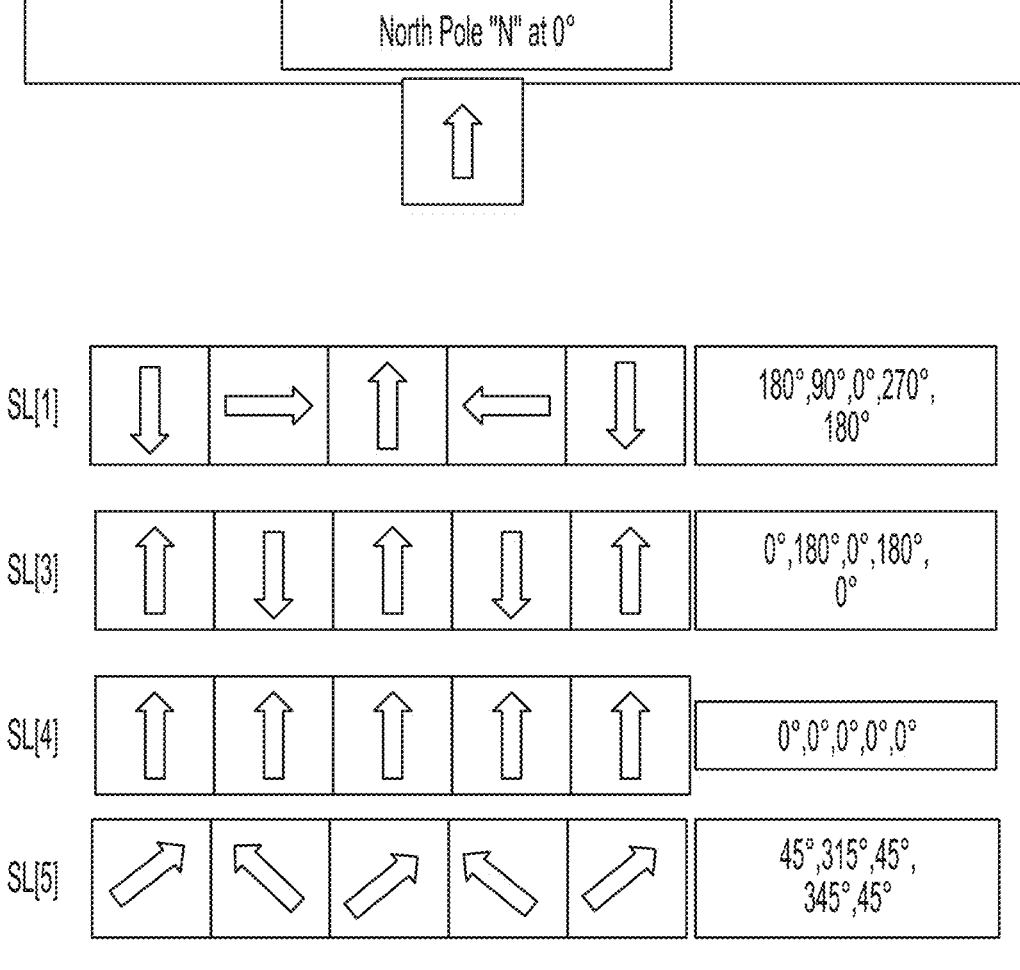
FIG. 47 is a schematic diagram showing some possible FCMA configurations having different SMS magnetic orientations, in accordance with some exemplary embodiments.

In certain exemplary embodiments, the SMSs 344 of each FCMA 343 can have different arrangements of magnetic orientations. FIG. 47 is a schematic diagram showing some possible FCMA 343 configurations having different SMS 344 magnetic orientations, in accordance with some exemplary embodiments. Among other things, FCMAs 343 may be configured or oriented in a way that opposes or attracts its neighboring segment. As a frame of reference, the direction of the N pole of each SMS 344 may be oriented in increments of 45° relative to a nominal 0° orientation, i.e., including orientations of the N pole at 0°, 45°, 90°, 135°, 180°, 225°, 270°, 315°, and 360°, although it should be noted that embodiments are not limited to such 45° increments and instead can accommodate any magnetic orientations. FIG. 47 shows four example configurations, the first (labeled SL[1]) having orientations of 180°, 90°, 0°, 270°, 180°, the second (labeled SL[3]) having orientations of 0°, 180°, 0°, 180°, 0°, the third (labeled SL[4]) having orientations of 0°, 0°, 0°, 0°, 0°, and the fourth (labeled SL[5]) having orientations of 45°, 315°, 45°, 315°, 45°.

In some exemplary configurations, for example, as shown in FIG. 47, the starting and ending SMSs 344 have the same magnetic orientation, although it should be noted that embodiments are not limited to such configurations and in alternative embodiments the starting and ending SMSs 344 can have different magnetic orientations.

Figure 48:
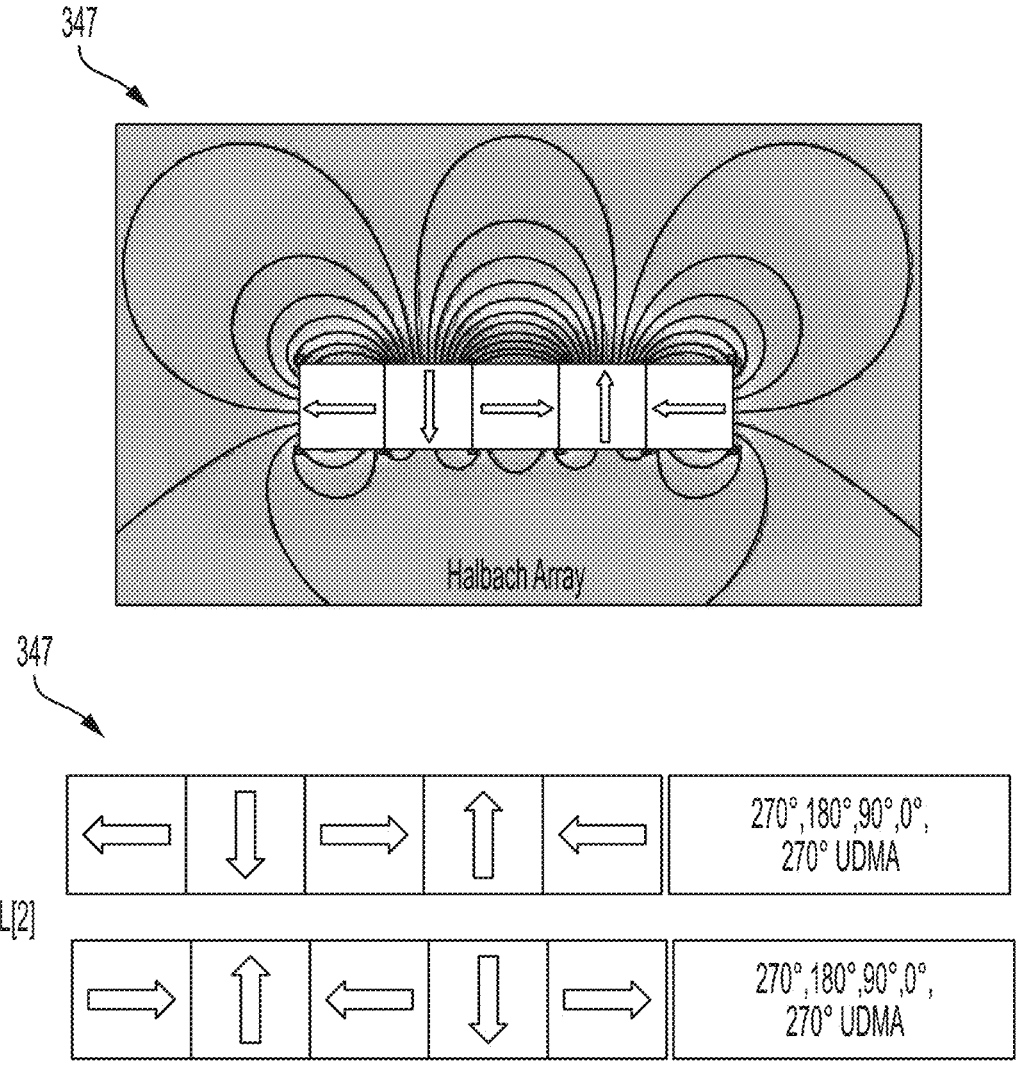
FIG. 48 is a schematic diagram showing the concept of a unidirectional magnetic array (UDMA), in accordance with certain exemplary embodiments.

In certain exemplary embodiments, the SMSs 344 of the FCMA 343 can be configured to form a unidirectional magnetic array (UDMA) 347 in which the magnetic field is redirected in one direction while the magnetic field in the opposite direction is eliminated or reduced. FIG. 48 is a schematic diagram showing the concept of a unidirectional magnetic array (UDMA) 347, in accordance with certain exemplary embodiments. The Halbach array diagram shows an example of how the polar configuration of the magnets can direct the magnetic field in one direction and reduce or eliminate the magnetic field in the other direction. FIG. 48 also shows two example UDMA configurations (labeled SL[2]), one having orientations of 270°, 180°, 90°, 0°, 270° and the other having orientations of 90°, 0°, 270°, 180°, 90°.

Figure 49A:
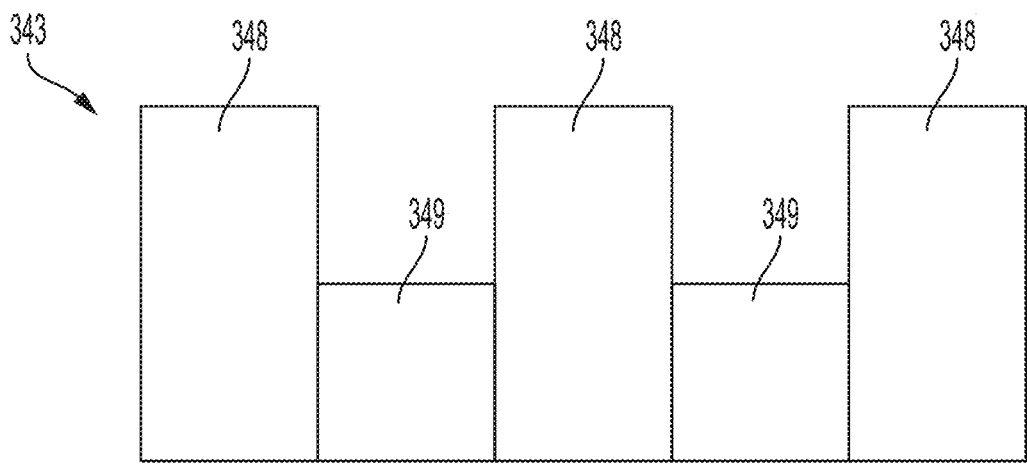
FIG. 49A is a schematic diagram showing an example arrangement starting with a tall SMS and then alternating between short and tall SMSs and ending with a tall SMS.
Figure 49B:
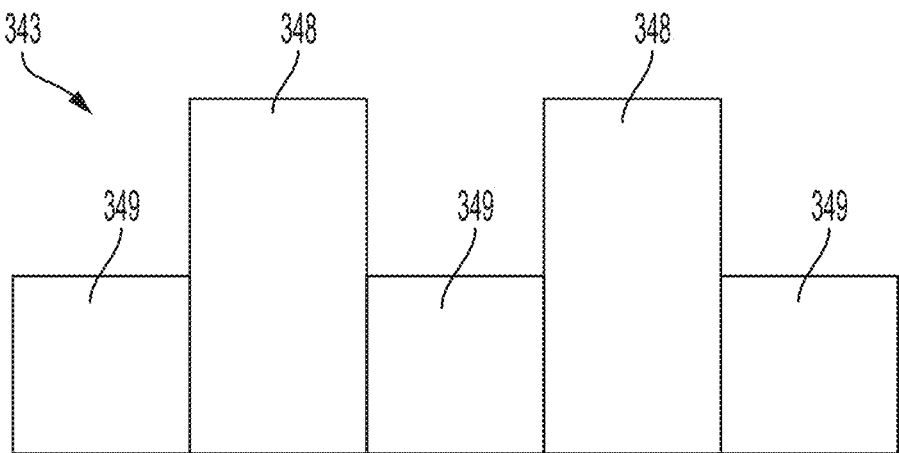
FIG. 49B is a schematic diagram showing an example arrangement starting with a short SMS and then alternating between tall and short SMSs and ending with a short SMS.
Figure 49C:
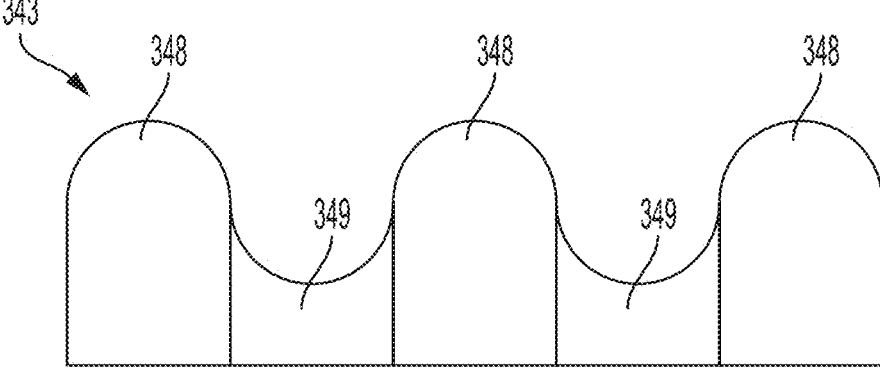
FIG. 49C is a schematic diagram showing the arrangement of FIG. 49A but with SMSs having rounded tops.
Figure 49D:
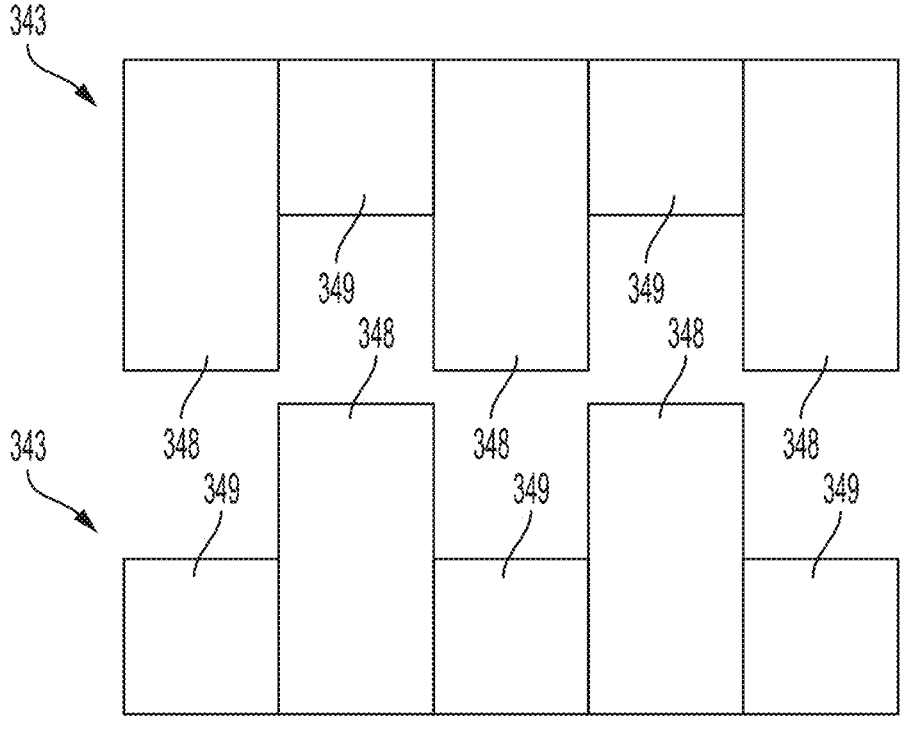
FIG. 49D shows how the arrangement of FIG. 49A and the arrangement of FIG. 49B might be placed on opposite mating assemblies.

In certain exemplary embodiments, the SMSs 344 of the FCMA 343 additionally or alternatively can be of different heights, e.g., using arrangements of tall 348 and short 349 magnets, or SMSs 344 having a common height can be placed at different relative heights, e.g., using a jig or form under the SMSs 344 to place the SMSs 344 at different heights. FIG. 49A is a schematic diagram showing an example arrangement starting with a tall SMS 348 and then alternating between short 349 and tall 348 SMSs and ending with a tall SMS 348. FIG. 49B is a schematic diagram showing an example arrangement starting with a short SMS 349 and then alternating between tall 348 and short 349 SMSs and ending with a short 349 SMS. FIG. 49C is a schematic diagram showing the arrangement of FIG. 49A but with SMSs 344 having rounded tops. It should be noted that FCMAs can be formed from SMSs 344 having more than just two different heights. It also should be noted that the FCMA 343 can include any combination and polar configuration of different height SMSs 344, e.g., tall/tall/short/tall/tall, short/short/tall/short/short, etc. It also should be noted that complementary arrangements of different height SMSs 344 and magnetic orientations can be used on opposite mating assemblies 16a, 16b in order to facilitate coupling and/or anastomosis creation. For example, FIG.

49D shows how the arrangement of FIG. 49A and the arrangement of FIG. 49B might be placed on opposite mating assemblies. SMSs 344 with rounded tops, e.g., as shown in FIG. 49C, could facilitate coupling of such opposite mating assemblies having different height SMSs 344. It should be noted that using FCMAs 343 with different magnet heights can not only create a better compression anastomosis but also lock/bite into the tissue to create a more secure connection.

Figures 50A, 50B:
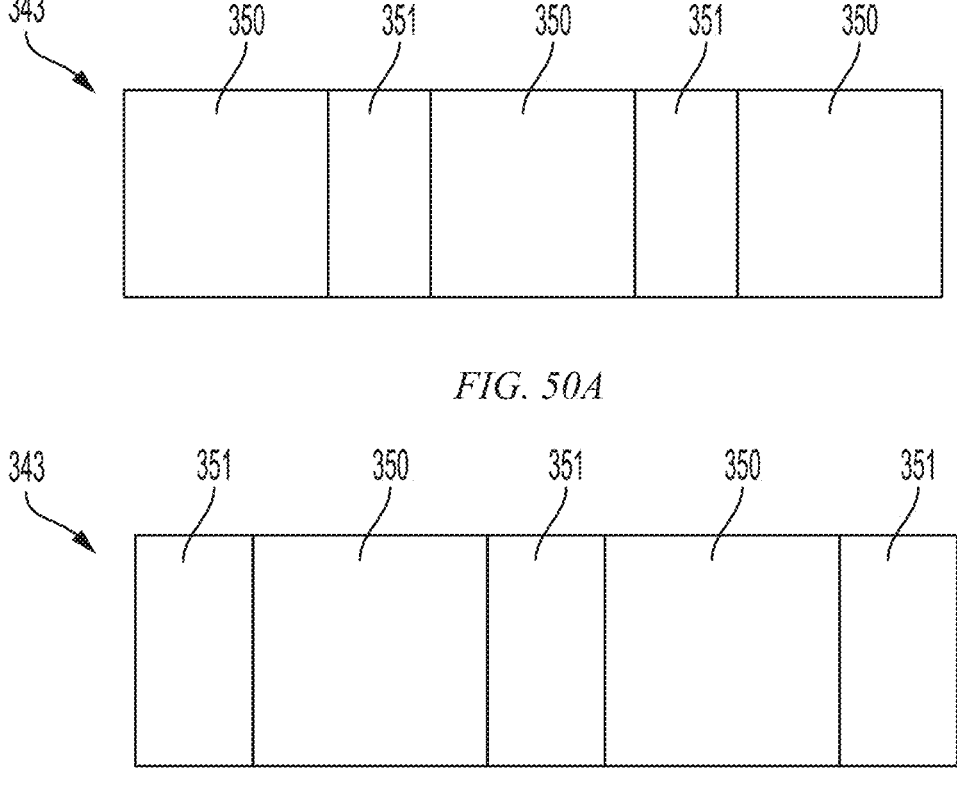
FIG. 50A is a schematic diagram showing an example arrangement starting with a thick SMS and then alternating between thin and thick SMSs and ending with a thick SMS.
FIG. 50B is a schematic diagram showing an example arrangement starting with a thin SMS and then alternating between thick and thin SMSs and ending with a thin SMS.

In certain exemplary embodiments, the SMSs 344 of the FCMA 343 additionally or alternatively can be of different widths, e.g., using arrangements of thick 350 and thin 351 magnets. FIG. 50A is a schematic diagram showing an example arrangement starting with a thick SMS 350 and then alternating between thin 351 and thick 350 SMSs and ending with a thick SMS 350. FIG. 50B is a schematic diagram showing an example arrangement starting with a thin SMS 351 and then alternating between thick 350 and thin 351 SMSs and ending with a thin SMS 351. It should be noted that FCMAs 343 can be formed from SMSs 344 having more than just two different widths. It also should be noted that the FCMA 343 can include any combination and polar configuration of different width SMSs 344, e.g., thick/ thick/thin/thick/thick, thin/thin/thick/thin/thin, etc. It also should be noted that in some cases using FCMAs 343 with different magnet thicknesses can reduce the surface area of the SMSs 344 used in the configuration while maintaining the same magnetic field strength.

Of course, embodiments can use any combination of SMSs 344 having different magnetic orientations, different magnet heights, and/or different magnet widths.

As discussed above, the SMSs 344 of an FCMA 343 can be secured to a larger magnetic structure such as a magnetic compression anastomosis device 16 or an individual magnetic segment 202 for a magnetic compression anastomosis device. For example, the larger magnetic structure can include a pocket 346 or other receptacle to receive and secure the FCMA 343 or the individual SMSs 344 associated with the FCMA 343. As discussed above, multiple magnetic segments 202 can be assembled (e.g., self-assembled) to form a polygon or other shaped assembly that is used to enhance magnetic compression anastomosis. These FCMAs 343 can allow the magnetic compression anastomosis device 16 to sense another polygon assembly at a greater distance.

Figure 51A:
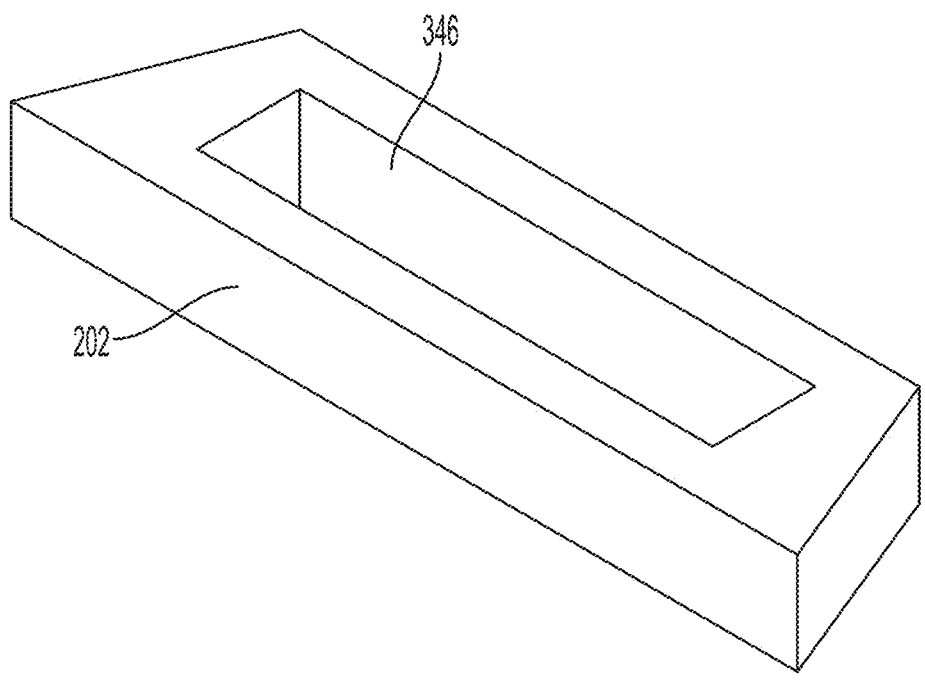
FIG. 51A is a schematic diagram showing one example of an individual magnetic segment for a magnetic compression anastomosis device, in accordance with certain exemplary embodiments.
Figure 51B:
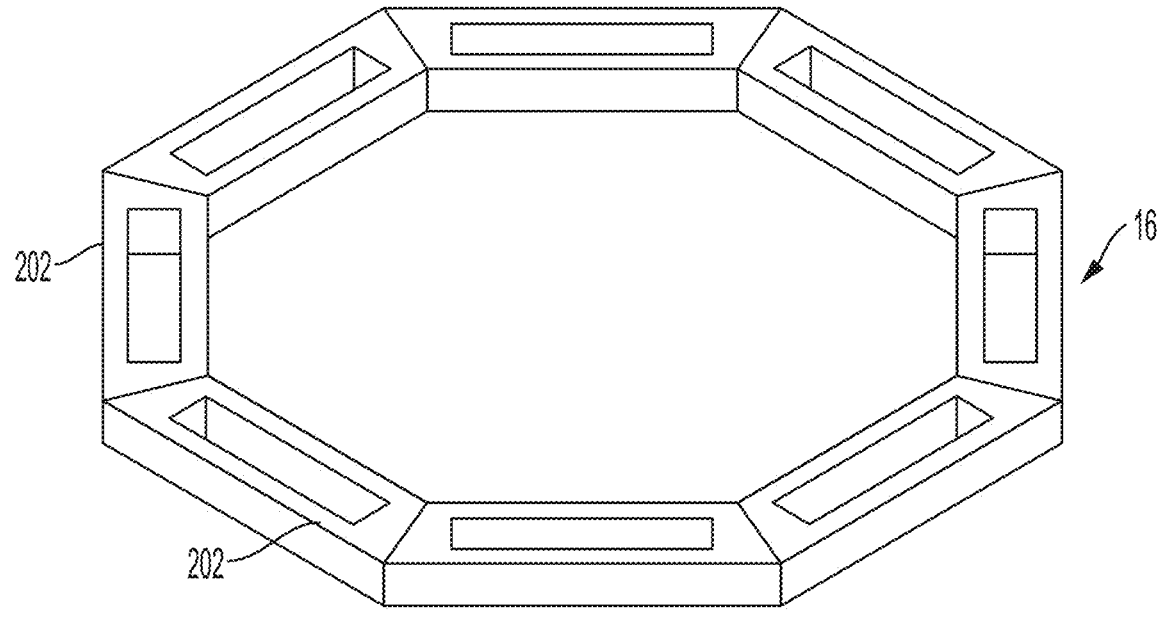
FIG. 51B is a schematic diagram showing a number of magnetic segments of the type shown in FIG. 51A assembled into a polygon (an octagon in this example).

FIG. 51A is a schematic diagram showing one example of an individual magnetic segment 202 for a magnetic compression anastomosis device 16, in accordance with certain exemplary embodiments. This magnetic segment 202 is trapezoidal shaped although embodiments are not limited to any particular shape. The magnetic segment 202 includes a pocket 346 for receiving the SMSs 344 of an FCMA 343. For convenience, the pocket 346 may be referred to herein as a "solid pocket," as it is generally rigid and may include indentations or other elements to secure the SMSs 344. The indentations or other securing elements may be configured to eliminate the potential of repelling SMSs 344 from 'jumping' out of the pocket 346. The SMSs 344 can be secured into the pocket 346, e.g., via epoxy-like substances or using screws/bolts or other fasteners. The size and/or shape of the pocket 346 may vary pending the height, thickness, and/or number of SMSs 344. FIG. 51B is a schematic diagram showing a number of magnetic segments 202 of the type shown in FIG. 51A assembled into a polygon (an octagon in this example).

In order to model and test various configurations, a variety of N52 neodymium rare earth magnets were placed in different field controlled magnetic arrays in order to compare the surface field strength of these different configurations. The size of the magnets used in testing was not a direct correlation to the size of the magnets used to create the anastomosis. These magnetic arrays and configurations were used to understand the strength of the surface field and how they compare to one another for consideration using different orientations for different tissue thicknesses (clinical scenarios). The actual surface field strength was measured by securing the designated field control magnetic array in a fixture and using a magnetometer 5 mm above the surface of the magnetic array. The fixture secured each magnet in place using a set screw in order to form the array. Certain magnetic configurations had poles that opposed each other, and the set screw restricted the magnets jumping out of the fixture. A grid was placed on top of the fixture so the surface field strength could be measured at different coordinates in the X-Y plane. The grid was in 3 mm increments, starting from the center of the array and moving in the X or Y direction. The top of the array was exposed to allow for each measurement of its surface field strength.

FIGS. 52A-52K are 3-dimensional graphical depictions of the surface field strengths of varying field controlled magnetic arrays as described above in which the Z axis is the measured surface field strength. The orientations and sizes of the small magnetic segments are detailed in the title of each graph. As mentioned above, the surface field strength was measure in Gauss and was measured 5 mm above the surface.

Figure 52A:
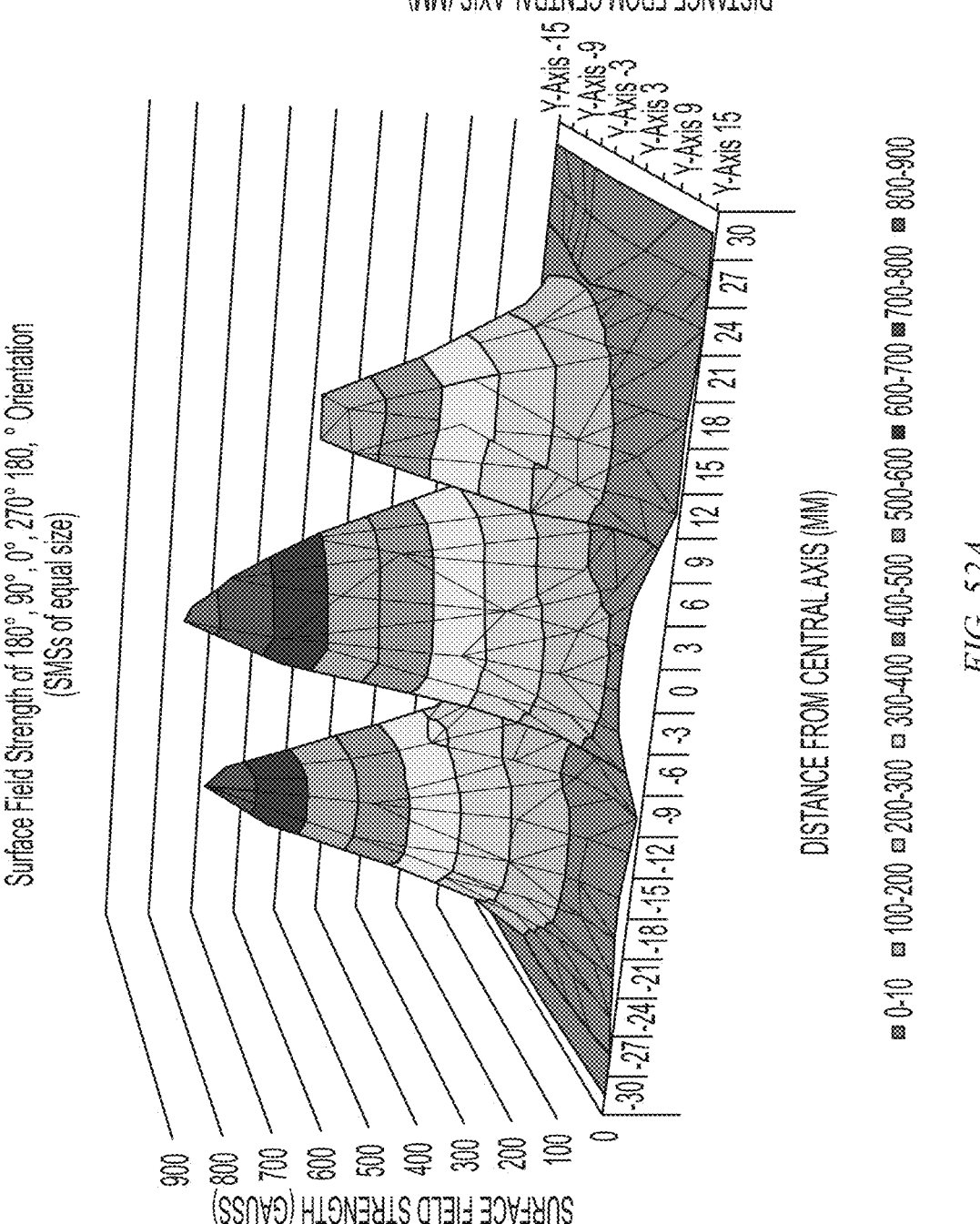
FIG. 52A shows surface field strength of a configuration having orientations of 180°, 90°, 0°, 270°, 180° with equal size SMSs.

FIG. 52A shows surface field strength of a configuration having orientations of 180°, 90°, 0°, 270°, 180° with equal size SMSs.

FIG. 52B shows surface field strength of a configuration having orientations of 270°, 180°, 90°, 0°, 270° with equal size SMSs.

FIG. 52C shows surface field strength of a configuration having orientations of 0°, 180°, 0°, 180°, 0° with equal size SMSs.

FIG. 52D shows surface field strength of a configuration having orientations of 0°, 0°, 0°, 0°, 0° with equal size SMSs.

Figure 52E:
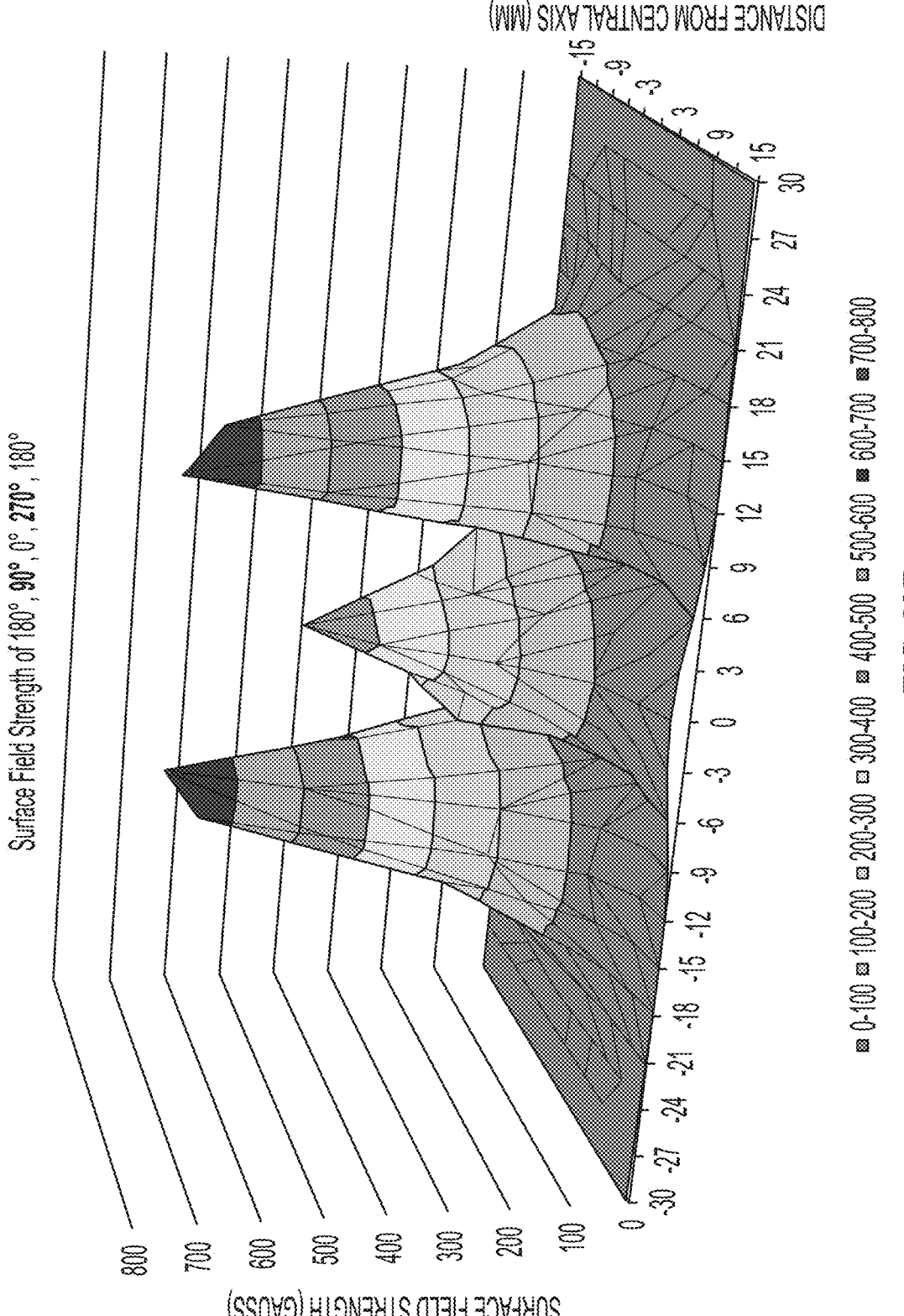
FIG. 52E shows surface field strength of a configuration having orientations of 180°, 90°, 0°, 270°, 180° with the thickness of the 90° and 270° SMSs reduced by 50% relative to the other SMSs.

FIG. 52E shows surface field strength of a configuration having orientations of 180°, 90°, 0°, 270°, 180° with the thickness of the 90° and 270° SMSs reduced by 50% relative to the other SMSs.

Figure 52F:
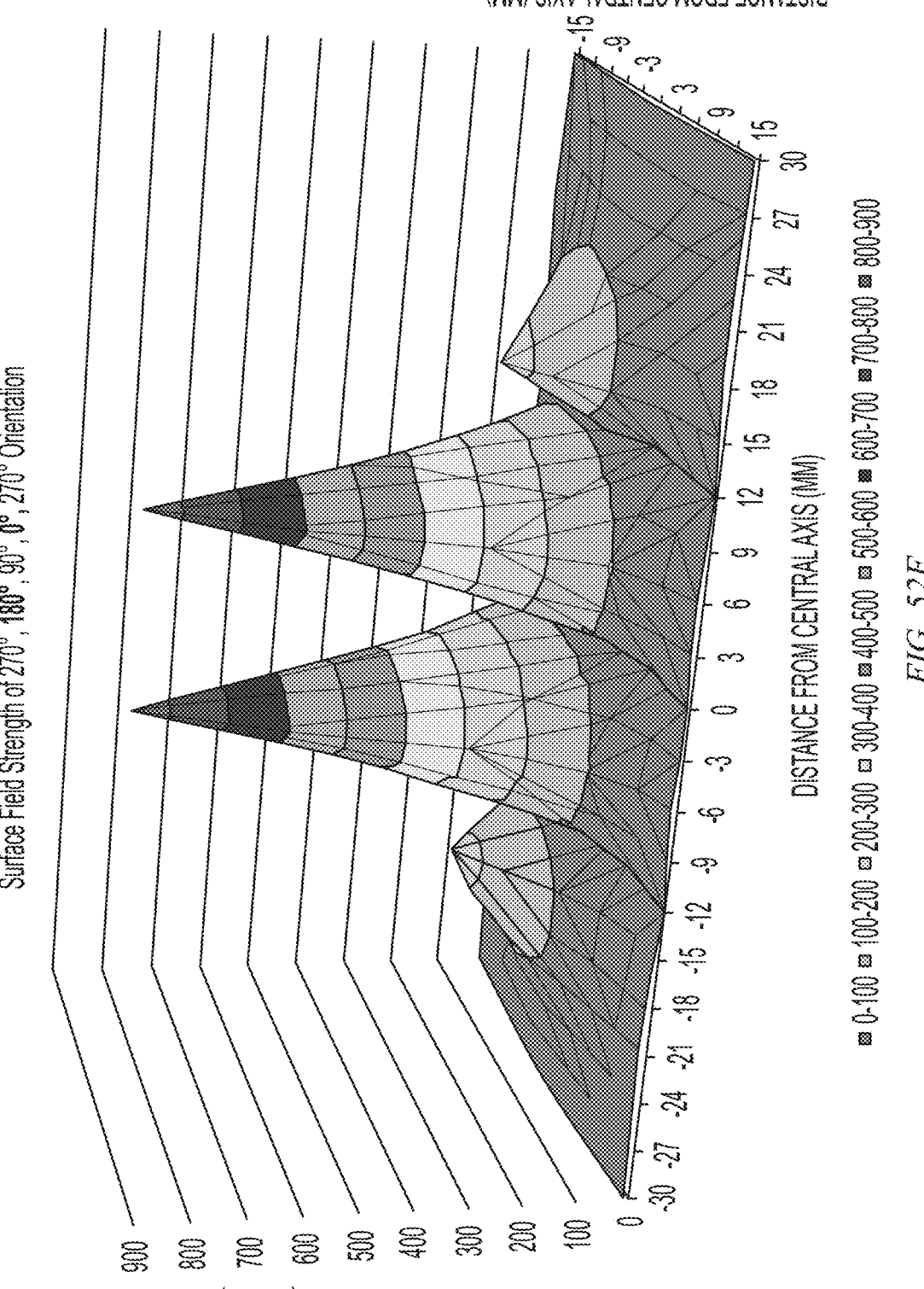
FIG. 52F shows surface field strength of a configuration having orientations of 270°, 180°, 90°, 0°, 270° with the thickness of the 180° and 0° SMSs reduced by 50% relative to the other SMSs.

FIG. 52F shows surface field strength of a configuration having orientations of 270°, 180°, 90°, 0°, 270° with the thickness of the 180° and 0° SMSs reduced by 50% relative to the other SMSs.

Figure 52G:
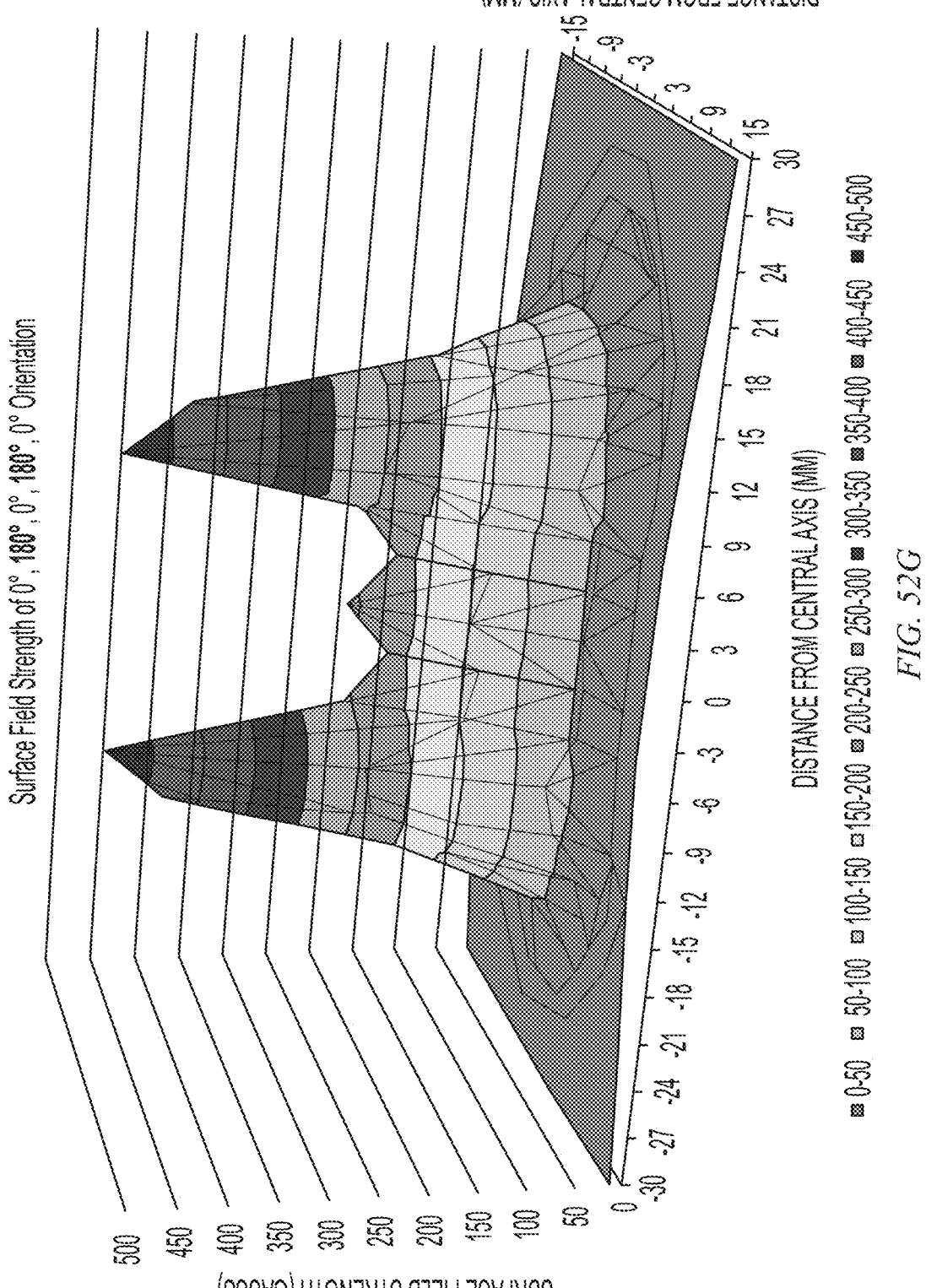
FIG. 52G shows surface field strength of a configuration having orientations of 0°, 180°, 0°, 180°, 0° with the thickness of the 180° SMSs reduced by 50% relative to the other SMSs.

FIG. 52G shows surface field strength of a configuration having orientations of 0°, 180°, 0°, 180°, 0° with the thickness of the 180° SMSs reduced by 50% relative to the other SMSs.

Figure 52H:
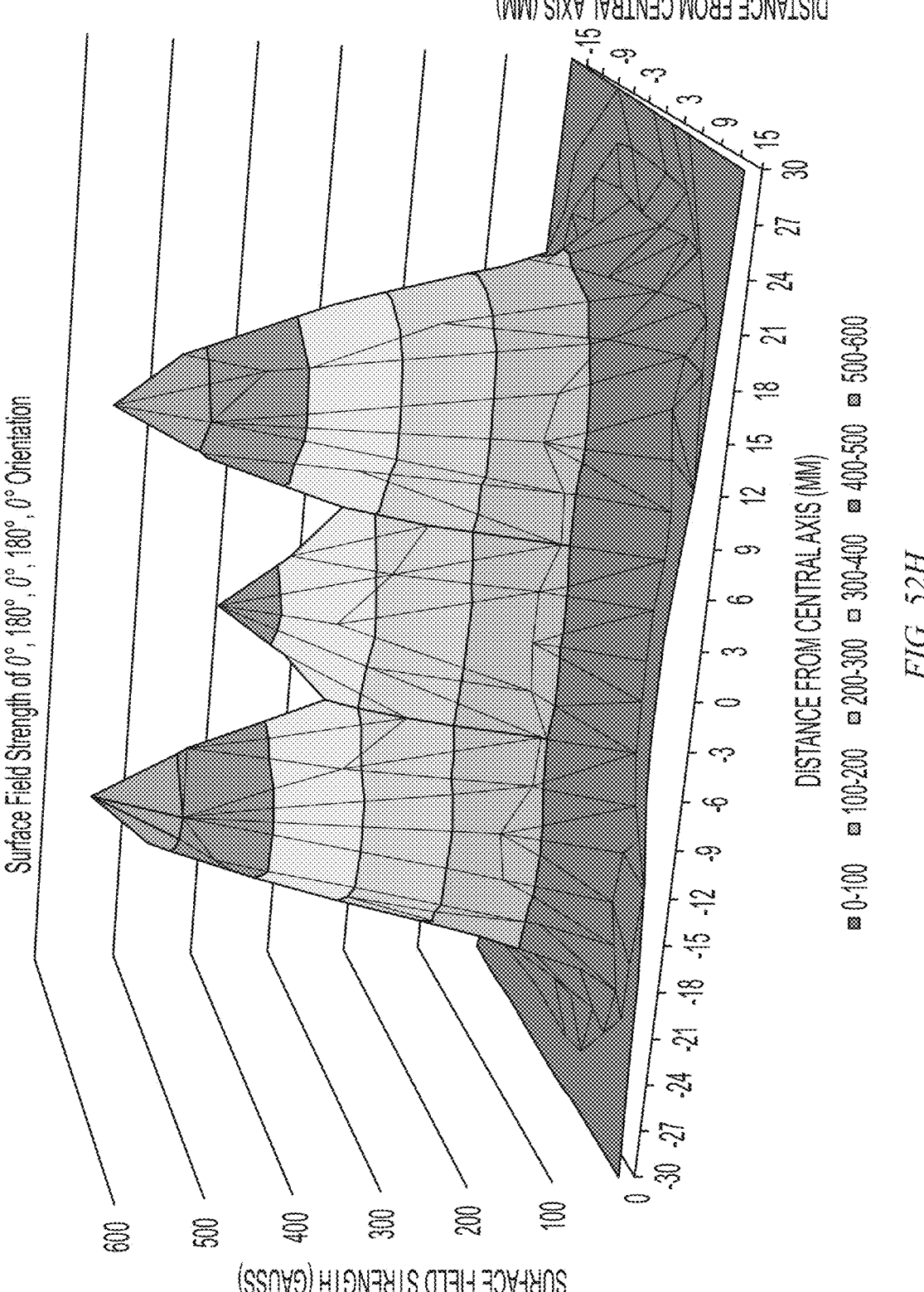
FIG. 52H shows surface field strength of a configuration having orientations of 0°, 180°, 0°, 180°, 0° with the height of the 0° SMSs increased by 100% relative to the other SMSs.

FIG. 52H shows surface field strength of a configuration having orientations of 0°, 180°, 0°, 180°, 0° with the height of the 0° SMSs increased by 100% relative to the other SMSs.

Figure 52I:
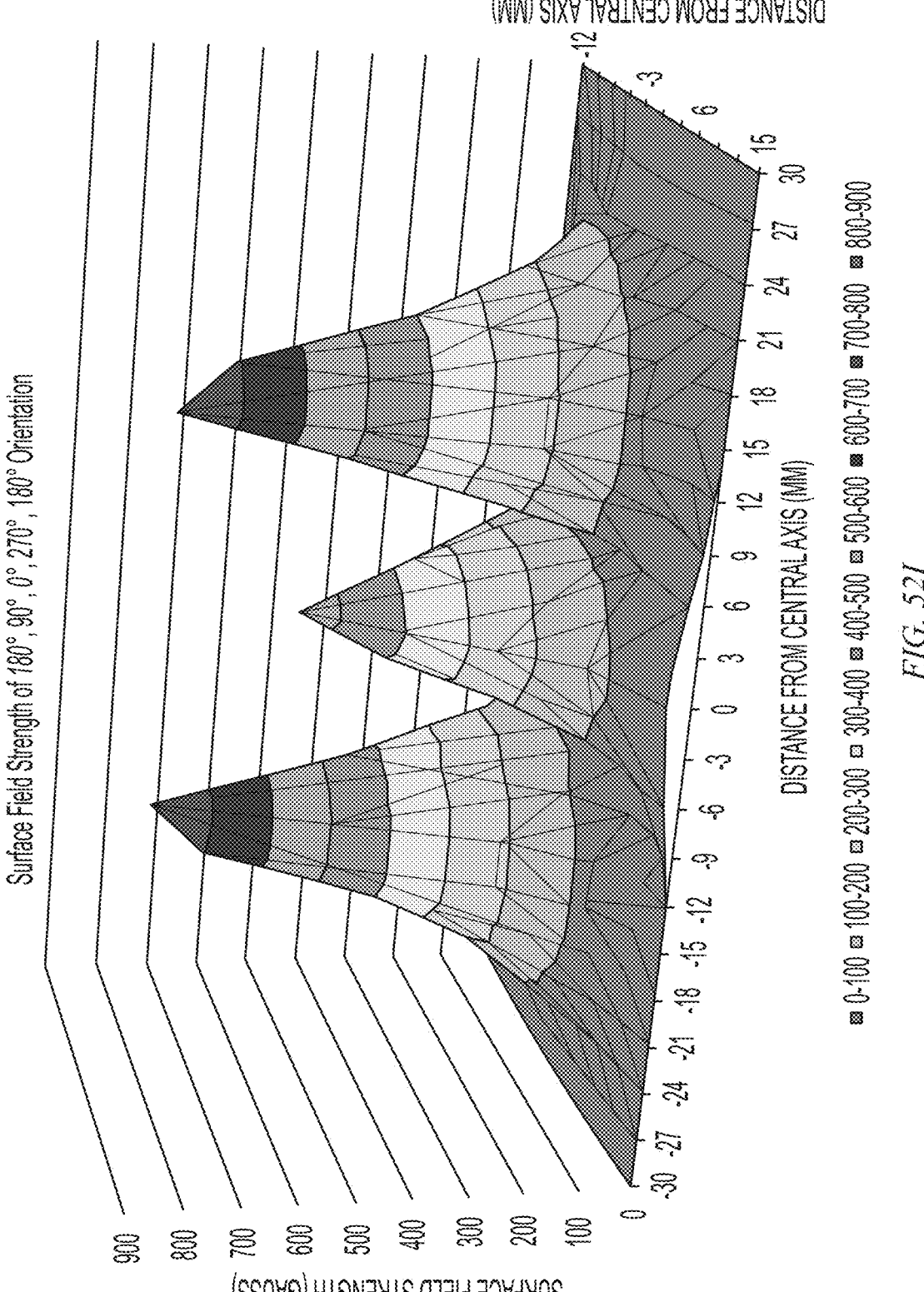
FIG. 52I shows surface field strength of a configuration having orientations of 180°, 90°, 0°, 270°, 0° with the height of the 180° and 0° SMSs increased by 100% relative to the other SMSs.

FIG. 52I shows surface field strength of a configuration having orientations of 180°, 90°, 0°, 270°, 0° with the height of the 180° and 0° SMSs increased by 100% relative to the other SMSs.

Figure 52J:
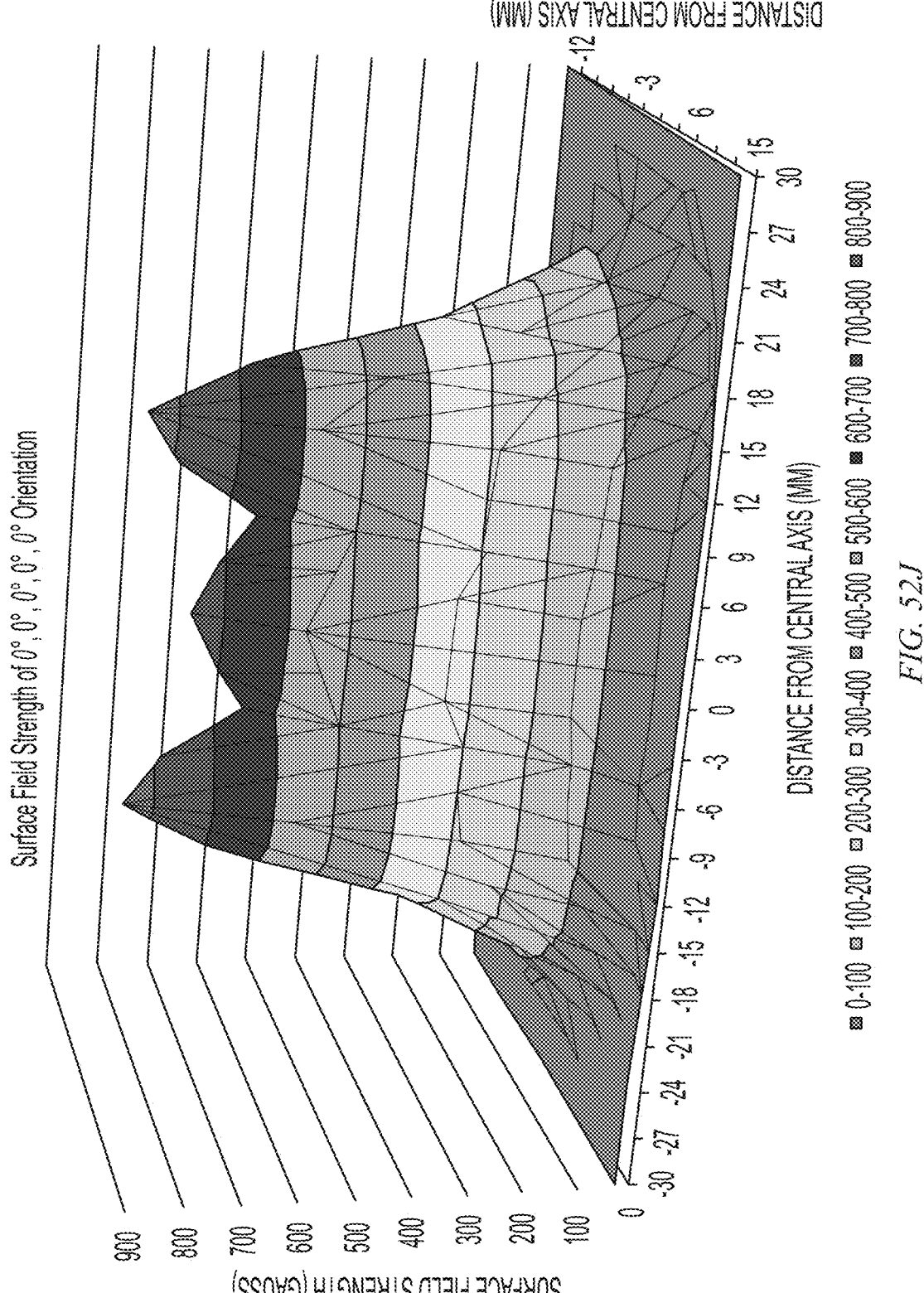
FIG. 52J shows surface field strength of a configuration having orientations of 0°, 0°, 0°, 0°, 0° with the height of the first, third, and fifth SMSs increased by 100% relative to the other SMSs.

FIG. 52J shows surface field strength of a configuration having orientations of 0°, 0°, 0°, 0°, 0° with the height of the first, third, and fifth SMSs increased by 100% relative to the other SMSs.

Figure 52K:
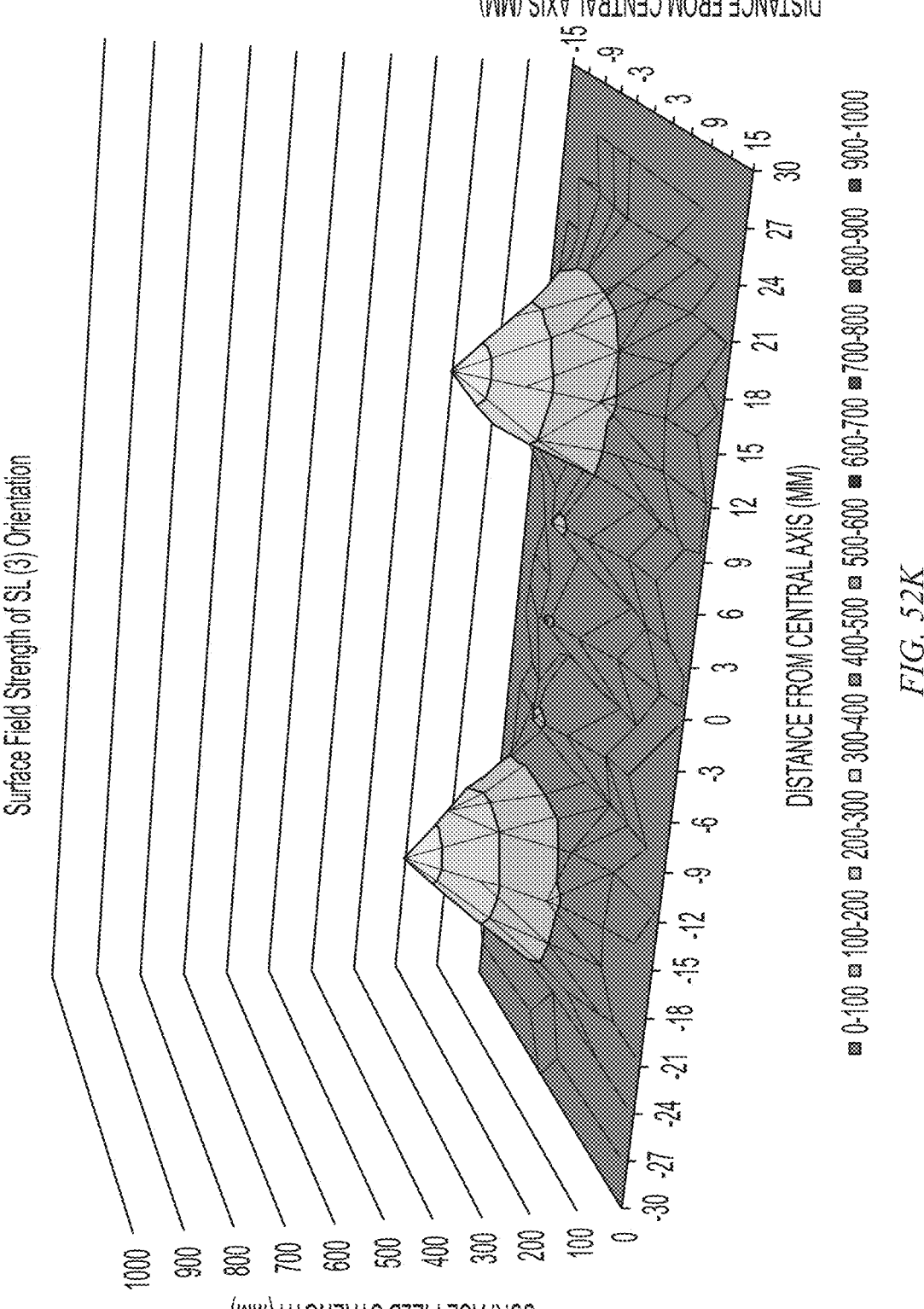
FIG. 52K shows surface field strength of the SL[3] configuration as a baseline for comparison with the other configurations.

FIG. 52K shows surface field strength of the SL[3] configuration as a baseline for comparison with the other configurations.

As shown, the shape of the surface field strength greatly differs between each FCMA configuration. Without being limited to any theory, the inventors attribute this to the different FCMA polar configurations (e.g., SMSs configured in the 0°, 45°, 90°, 135°, 180°, 225°, 270°, 315°, or 360° orientation) as well as to the different thicknesses and heights of the SMSs in conjunction with the different polar orientations. As shown, each FCMA configuration has different peak surface field strength values occurring at varying distances from the central axis (i.e., the location at which the surface field strength is at its maximum varies between FCMA configurations). Generally speaking, the distance at which each pair of magnetic arrays can detect each other increases as the surface field strength increases and vice versa.

Figure 53:
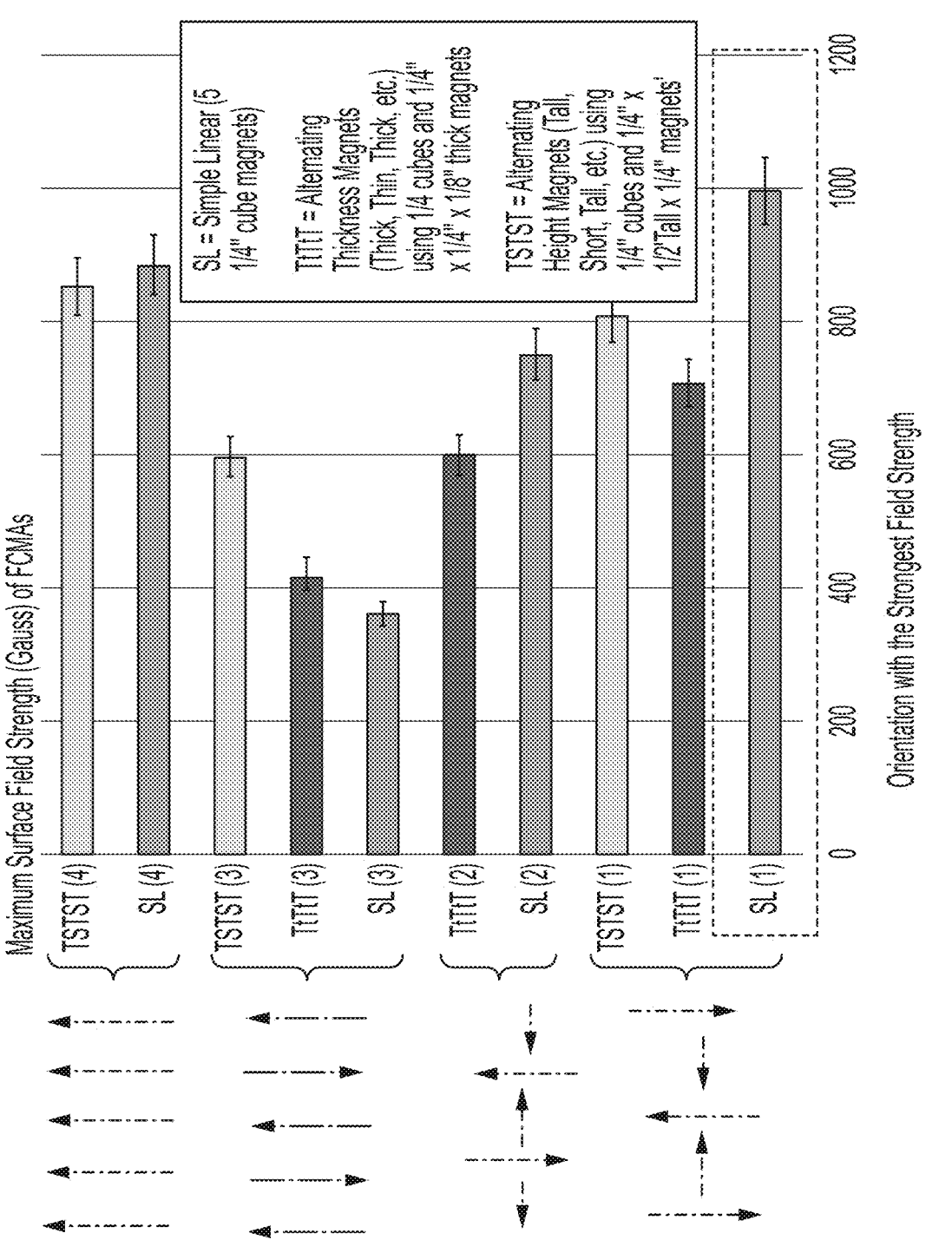
FIG. 53 shows maximum surface field strength (Gauss) for FCMAs of various simple linear, thick/thin, and tall/short configurations as indicated by the arrows including tall/short/tall/short/tall (TSTST) and thick/thin/thick/thin/thick (TtTtT) configurations.

FIG. 53 shows maximum surface field strength (Gauss) for FCMAs of various simple linear, thick/thin, and tall/short configurations as indicated by the arrows including tall/short/tall/short/tall (TSTST) and thick/thin/thick/thin/thick (TtTtT) configurations.

Figure 54:
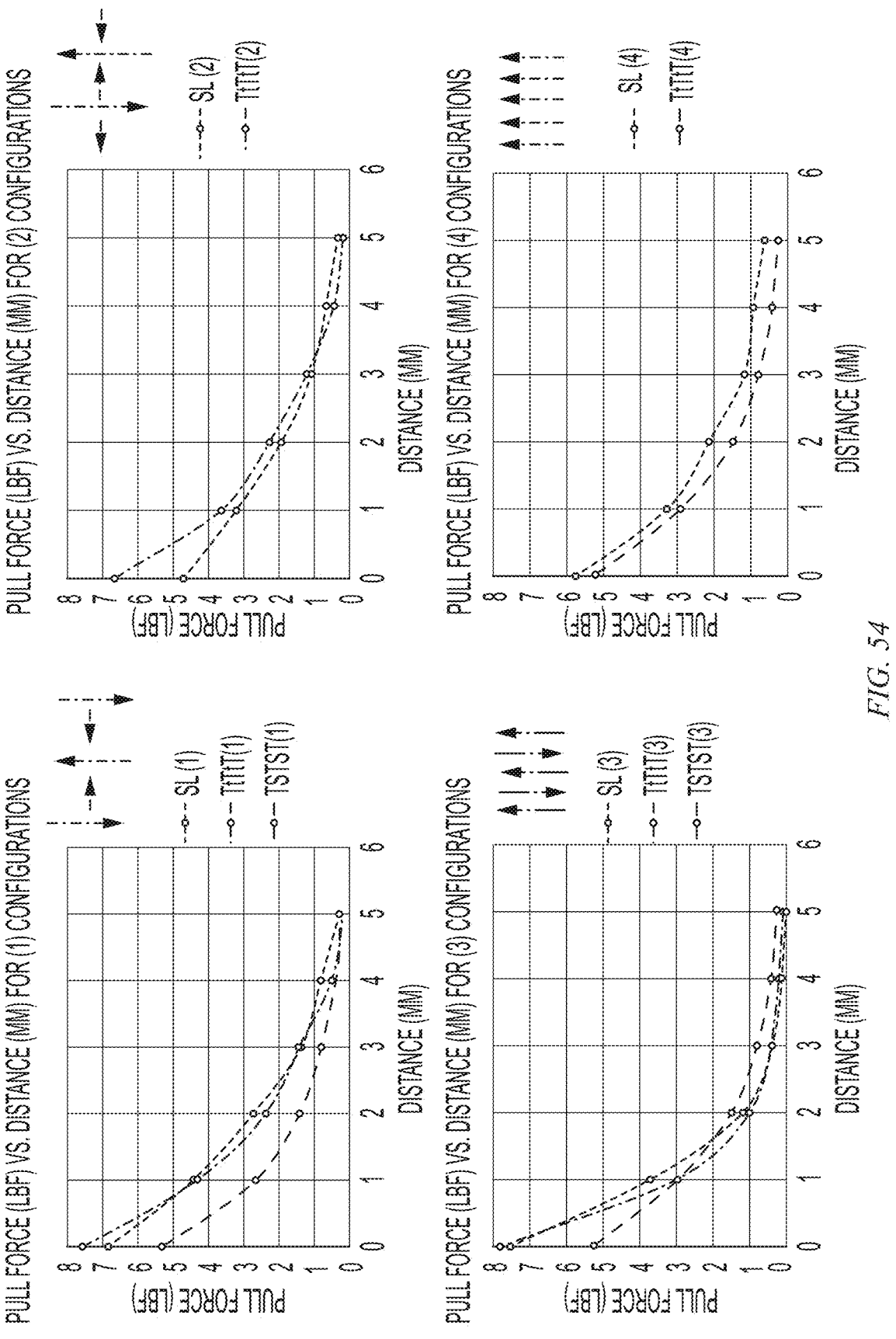
FIG. 54 shows pull forces against a steel plate for FCMAs of various simple linear, thick/thin, and tall/short configurations.

FIG. 54 shows pull forces against a steel plate for FCMAs of various simple linear, thick/thin, and tall/short configurations. As shown, the SL[3] configuration decays quicker after 1 mm. Other configurations are 2× stronger at further distances.

Figure 55:
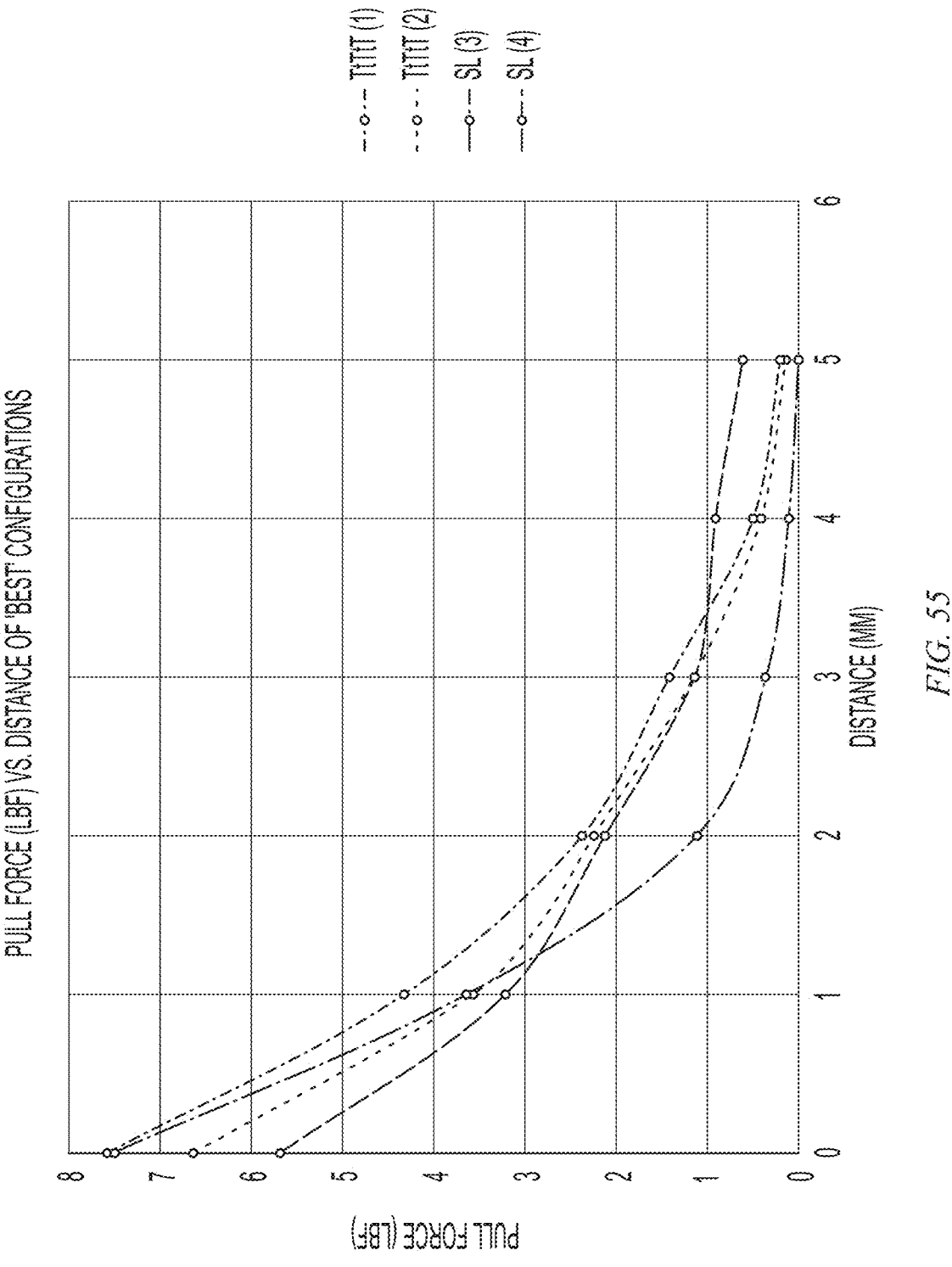
FIG. 55 shows pull forces for various "best" performing configurations.

FIG. 55 shows pull forces for various "best" performing configurations. As shown, thick/thin/thick/thin/thick (TtTtT) and SL[4] configurations perform better than the SL[3] configuration at maintaining attraction at largest distances, potentially allowing for coupling through thicker tissues.

Figure 56:
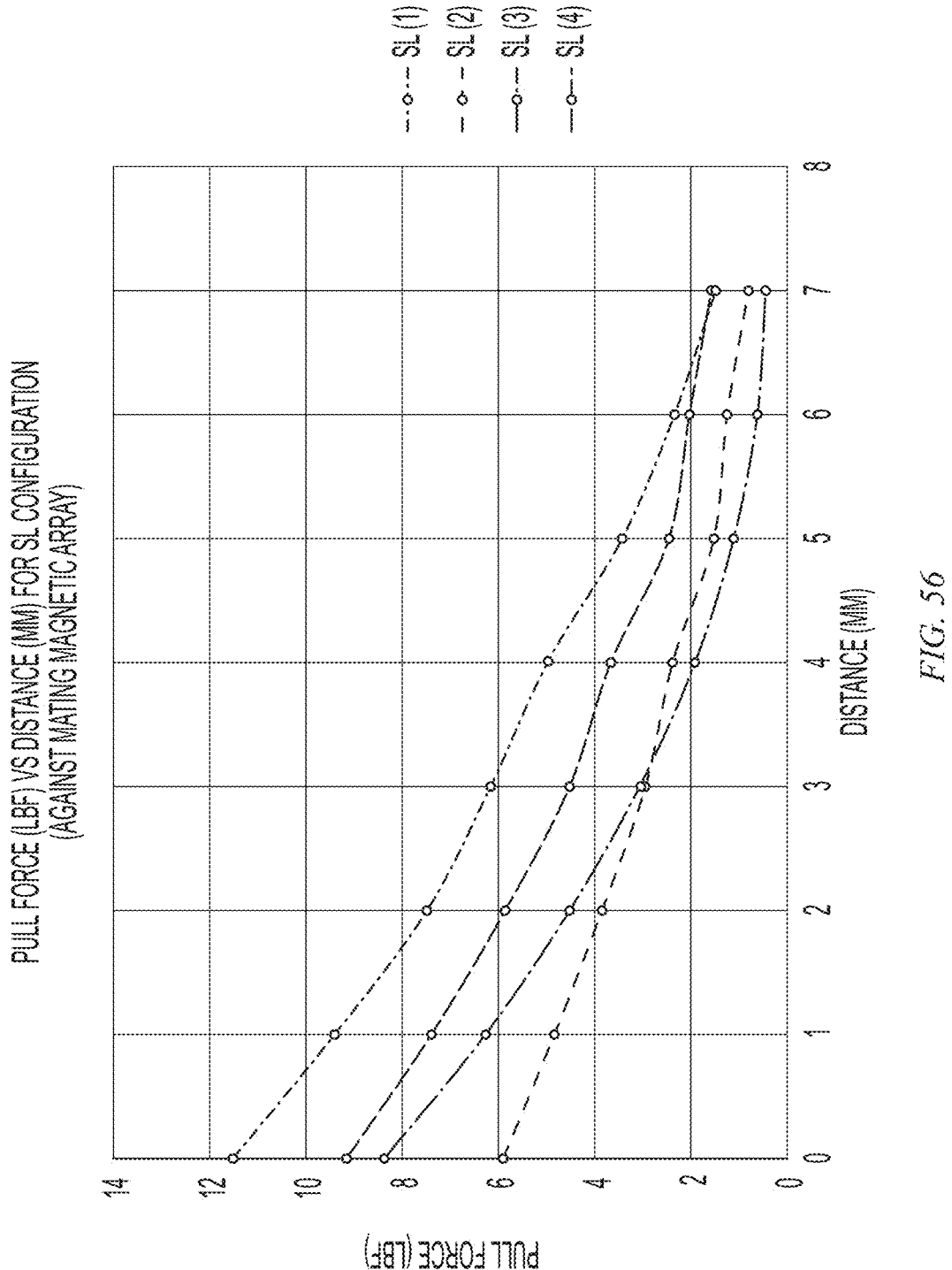
FIG. 56 shows pull force against a mating array for some simple matching linear configurations.

FIG. 56 shows pull force against a mating array for some simple matching linear configurations. As shown, SL[1] and SL[4] greatly outperform SL[3] in terms of pull force over distance. For example, there is a higher force at 0 mm and a lower rate of decay as distance increased. The tall/short (male/female) nesting shows particularly promising results.

Among other things, by selecting a particular FCMA configuration, a surgeon can "tune" the surface field strength between devices for desired performance. Thus, for example, if it is necessary to maximize the surface field strength, e.g., in order to facilitate bringing tissue together, the surgeon may use different FCMA configurations in order to increase the distance at which the mating assemblies are able to attract to each other. This can be useful, for example, when dealing with organs or patients with thicker tissue (e.g., greater than 5 mm) and can create a better compression anastomosis.

It should be noted that although example FCMAs 343 having five SMSs 344 are shown and described herein, embodiments are not limited to FCMAs 343 having five SMSs 344 and instead FCMAs 343 can have other numbers of SMSs 344.

Figure 57A:
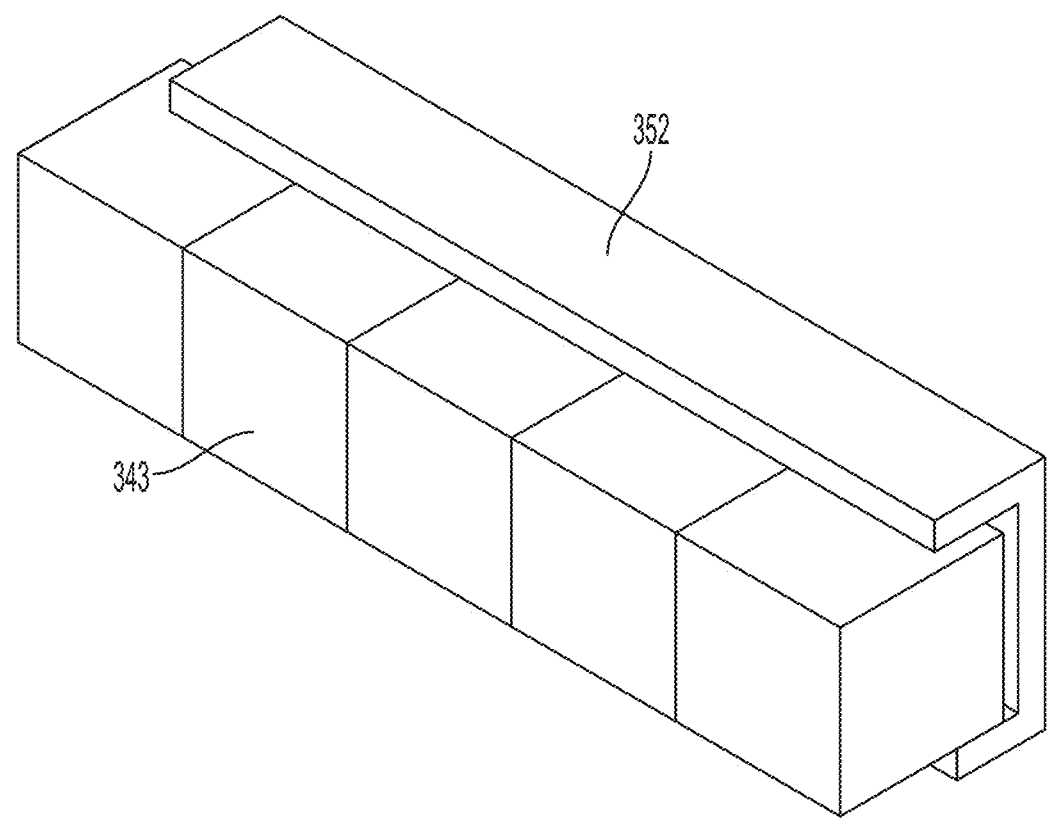
FIG. 57A is a schematic diagram showing a perspective view of a portion of an exoskeleton, backbone, or guide including a recess, channel, or slot configured to secure an FCMA having a number of SMSs, in accordance with various exemplary embodiments.
Figure 57B:
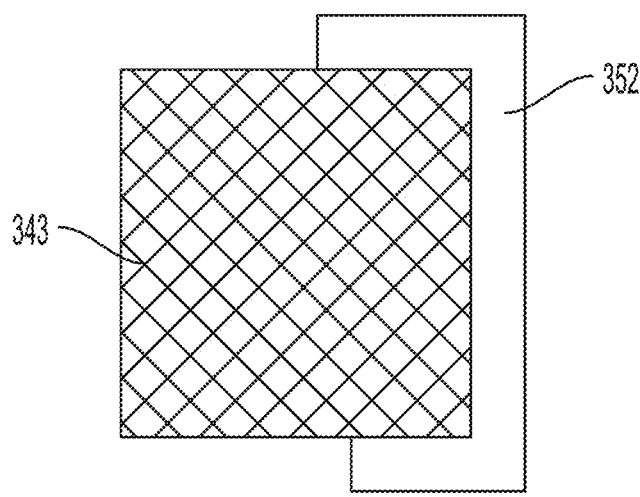
FIG. 57B shows a cross-sectional end view of the configuration of FIG. 57A.

It also should be noted that an FCMA 343 does not need to be secured within a pocket 346 of the types shown in FIGS. 46A-46D but instead could be secured in other anastomosis device structures such as, for example, in a recess, channel, or slot such as in an anastomosis device exoskeleton 352, backbone, or guide of the type described herein with reference to FIG. 42, e.g., where one or more of the magnetic segments 202 can be an FCMA 343 having a plurality of SMSs 344 rather than a single magnet such that a given flexible exoskeleton element 352 can secure an FCMA 343 rather than a single magnet. FIG. 57A is a schematic diagram showing a perspective view of a portion of an exoskeleton 352, backbone, or guide including a recess, channel, or slot configured to secure an FCMA 343 having a number of SMSs 344, in accordance with various exemplary embodiments. FIG. 57B shows a cross-sectional end view of the configuration of FIG. 57A.

Figure 58:
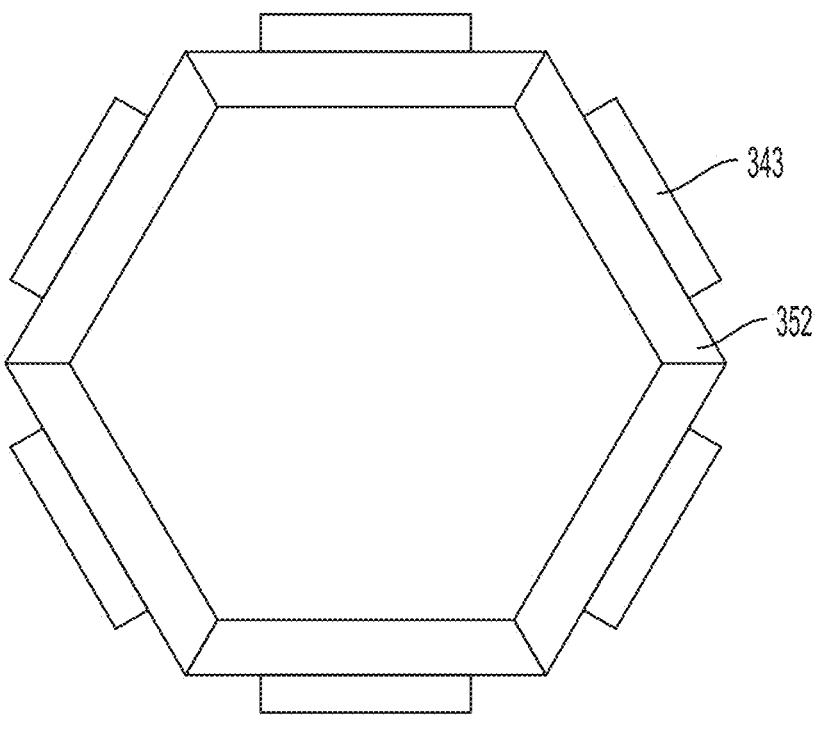
FIG. 58 is a schematic diagram showing an exemplary anastomosis device in which the segments of the exoskeleton are assembled to form a hexagon with the FCMAs on the outside of the hexagon.
Figure 59:
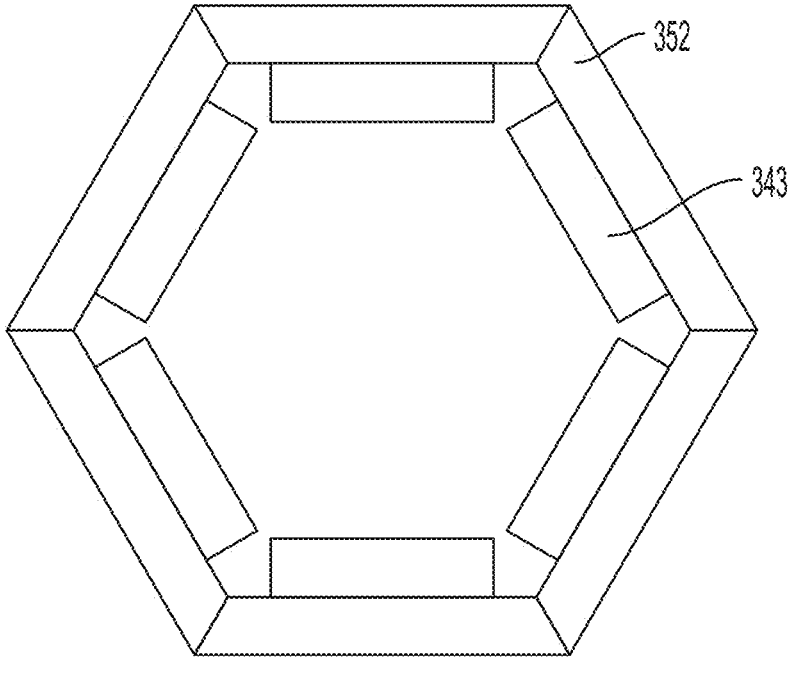
FIG. 59 is a schematic diagram showing an exemplary anastomosis device in which the segments of the exoskeleton are assembled to form a hexagon with the FCMAs on the inside of the hexagon.

FIG. 58 is a schematic diagram showing an exemplary anastomosis device in which the segments of the exoskeleton 352 are assembled to form a hexagon with the FCMAs 343 on the outside of the hexagon. FIG. 59 is a schematic diagram showing an exemplary anastomosis device in which the segments of the exoskeleton 352 are assembled to form a hexagon with the FCMAs 343 on the inside of the hexagon. Of course, the anastomosis device is not limited to any particular shape or to any particular structure for securing the SMSs 344 of an FCMA 343.

Figure 60:
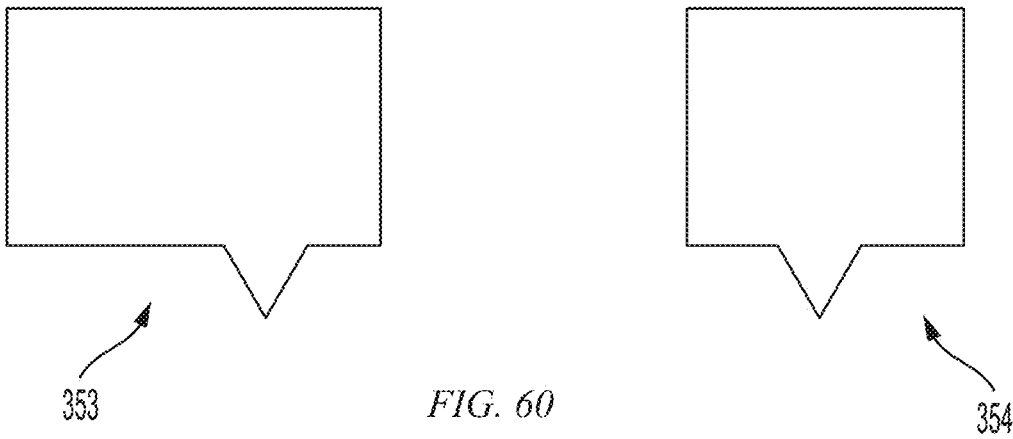
FIG. 60 is a schematic diagram showing the concept of keyed features that can be used to secure SMSs, in accordance with various exemplary embodiments.
Figure 61:
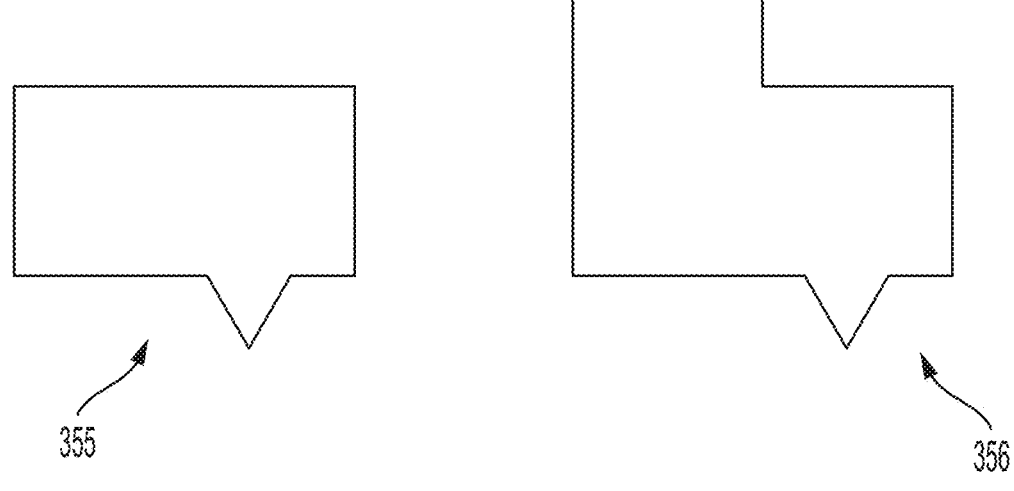
FIG. 61 is a schematic diagram showing how SMSs of the type shown in FIG. 60 may be configured to support arrangements of tall and short magnets, in accordance with various exemplary embodiments.

The SMSs 344 of an FCMA 343 may be secured within a pocket 346, recess, channel, or slot in any of a number of ways such as using particular materials (e.g., an elastic or conforming material that can hold SMSs in place within a pocket 346, recess, channel, or slot), mechanical fasteners, glue/cement, friction fit, snap fit, and/or keyed features, and the present invention is not limited to any particular way of securing the SMSs. FIG. 60 is a schematic diagram showing the concept of keyed features that can be used to secure SMSs, e.g., the keyed element on the SMS 353 is configured to mate with corresponding receptacle 354 in the segment and in this example the SMS 353 may be slid into the segment 354 with the keyed element 354 helping to secure the SMS 353 within the segment 354. FIG. 61 is a schematic diagram showing how SMSs 344 of the type shown in FIG. 60 may be configured to support arrangements of tall 356 and short 355 magnets, in accordance with various exemplary embodiments. In this example, since the insertion axis of the SMSs is normal to the mating axis, a tall SMS might have an extension in the mating axis direction rather than simply being longer in the insertion axis direction.

Figure 62:
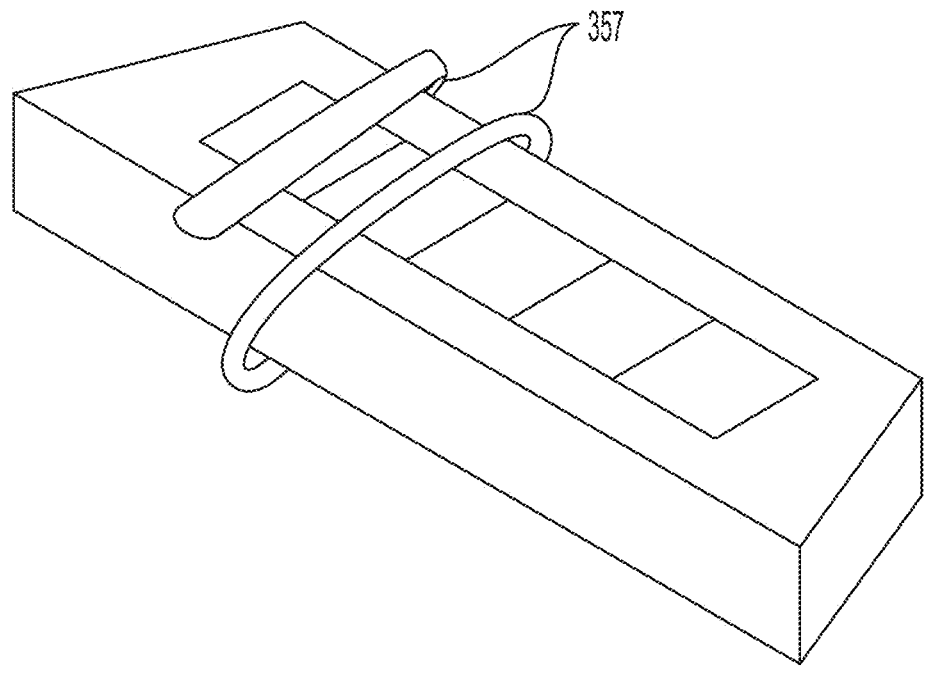
FIG. 62 is a schematic diagram showing the concept of mechanical bindings to help secure magnets of an FCMA, in accordance with various exemplary embodiments.
Figure 63:
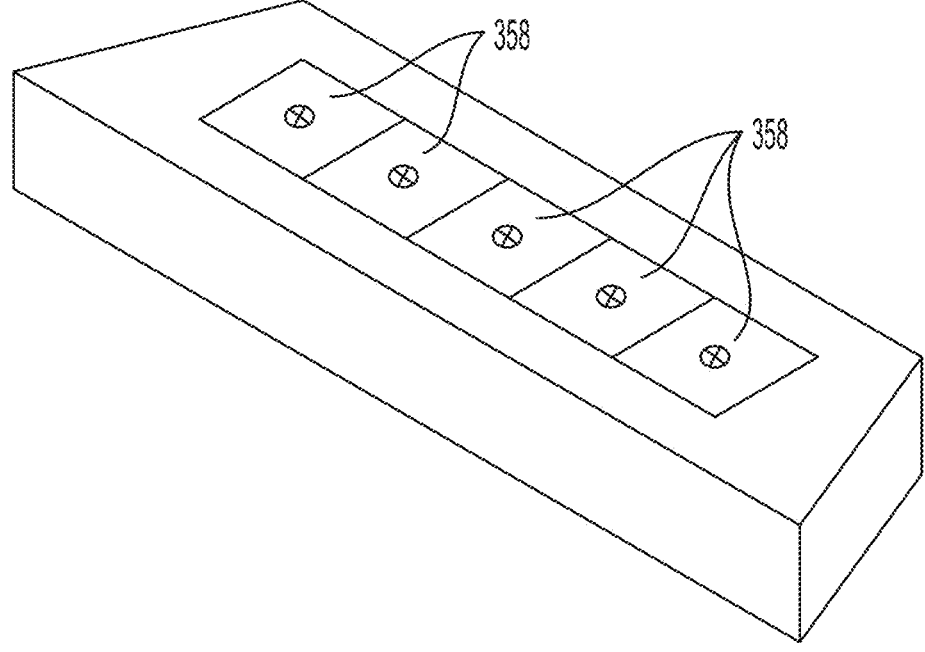
FIG. 63 is a schematic diagram showing the concept of mechanical fasteners to help secure magnets of an FCMA, in accordance with various exemplary embodiments.

Additional elements may be provided for helping to secure SMSs within a pocket 346, recess, channel, slot, or other holder, e.g., end blocks (e.g., plastic or non-magnetic metal) to prevent the SMSs from sliding out of the ends of a channel (e.g., due to repelling magnetic forces), mechanical fasteners 358 (e.g., screws as depicted in FIG. 63), mechanical bindings 357 (e.g., bands, clips, belts, harnesses, as depicted in FIG. 62), or other elements.

Potential Claims

Various embodiments of the present invention may be characterized by the potential claims listed in the paragraphs following this paragraph (and before the actual claims provided at the end of the application). These potential claims form a part of the written description of the application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public. Nor are these potential claims intended to limit various pursued claims.

Without limitation, potential subject matter that may be claimed (prefaced with the letter "P" so as to avoid confusion with the actual claims presented below) includes:

P1. An assembly for magnetic compression anastomosis comprising a field controlled magnetic array (FCMA) including a plurality of smaller magnetic segments (SMSs).

P2. An assembly according to claim P1, wherein the magnetic segments have magnetic orientations of 0°, 45°, 90°, 135°, 180°, 225°, 270°, 315°, or 360°.

P3. An assembly according to any one of claims P1-P2, wherein the starting and ending SMSs of the FCMA have the same magnetic/polar orientation.

P4. An assembly according to any one of claims P1-P3, wherein the SMSs in the FCMA are arranged linearly.

P5. An assembly according to any one of claims P1-P3, wherein the SMSs in the FCMA are arranged non-linearly.

P6. An assembly according to any one of claims P1-P5, wherein at least two SMSs in the FCMA are arranged at different heights.

P7. An assembly according to claim P6, wherein the at least two SMSs are different height SMSs.

P8. An assembly according to claim P6, further comprising a jig or form that places the at least two SMSs at different heights.

P9. An assembly according to any one of claims P1-P8, wherein at least two SMSs in the FCMA are different width SMSs.

P10. An assembly according to any one of claims P1-P9, wherein the SMSs in the FCMA are configured to form a unidirectional magnetic array (UDMA).

P11. An assembly according to any one of claims P1-P10, wherein the assembly includes a pocket in which the SMSs of the FCMA are held.

P12. An assembly according to claim P11, wherein the pocket comprises indentations or other elements to secure the SMSs.

P13. An assembly according to any one of claims P11-P12, wherein the assembly is a magnetic segment for a magnetic compression anastomosis device.

P14. An assembly according to claim P13, wherein the magnetic compression anastomosis device is shaped as a polygon and wherein the magnetic segment is configured to form one side of the polygon.

P15. A magnetic compression anastomosis device comprising an assembly according to any one of claims P1-P14.

P16. A method for magnetic compression anastomosis using an assembly according to any of one claims P1-P15 in which an operator selects and configures the SMSs to achieve a desired surface field strength for a given compression anastomosis procedure including at least one of the magnetic orientations of the SMSs, the heights of the SMSs, or the widths of the SMSs.

Without limitation, additional potential subject matter that may be claimed (prefaced with the letter "P" so as to avoid confusion with the actual claims presented below) includes:

P1. An apparatus for forming a compression anastomosis, the apparatus comprising at least one field controlled magnetic array (FCMA), wherein each FCMA includes a support structure having a receptacle configured to receive and secure a plurality of small magnetic segments each having a north magnetic pole individually oriented within the FCMA.

P2. The apparatus described in claim P1, wherein the receptacle is configured to allow each small magnetic segment to be individually oriented within the FCMA with the north magnetic pole at an orientation of 0°, 90°, 180°, or 270°, with respect to a plane in the FCMA.

P3. The apparatus described in any one of claims P1-P2, wherein the receptacle is configured to allow each small magnetic segment to be individually oriented within the FCMA with the north magnetic pole at an orientation of 0°, 45°, 90°, 135°, 180°, 225°, 270°, or 315° with respect to a plane in the FCMA.

P4. The apparatus as described in any one of claims P1-P3, wherein the receptacle is configured to allow each small magnetic segment to be individually oriented within the FCMA with the north magnetic pole at an orientation of 0°, 45°, 90°, 135°, 180°, 225°, 270°, or 315° with respect to a second plane in the FCMA.

P5. The apparatus as described in any one of claims P1-P4, wherein two or more of the plurality of small magnetic segments are different heights.

P6. The apparatus as described in any one of claims P1-P5, wherein two or more of the plurality of small magnetic segments are different widths.

P7. The apparatus as described in any one of claims P1-P6, wherein two or more of the plurality of small magnetic segments have different magnetic strengths.

P8. The apparatus as described in any one of claims P1-P7, wherein two or more of the plurality of small magnetic segments have different shapes.

P9. The apparatus as described in any one of claims P1-P8, further comprising an exoskeleton comprising a pocket capable of receiving a field controlled magnetic array.

P10. The apparatus as described in claim P9, wherein the pocket has an indentation capable of holding the field controlled magnetic array in place.

P11. The apparatus as described in any one of claims P1-P10, further comprising an exoskeleton configured to secure the field controlled magnetic array in place.

P12. The apparatus as described in any one of claims P9-P11, further comprising a securement device configured to secure the field controlled magnetic array within the exoskeleton.

P13. The apparatus as described in claim P12, wherein the securement device is a screw.

P14. The apparatus as described in claim P12, wherein the securement device is a band.

P15. The apparatus as described in any one of claims P1-P14, wherein the small magnetic segments are arranged linearly.

P16. The apparatus as described in any one of claims P1-P15, wherein the one or more field controlled magnetic arrays are arranged in a polygonal shape.

P17. The apparatus as described in claim P16, wherein the shape is an octagon.

P18. The apparatus as described in any one of claims P16-P17, wherein the field controlled magnetic arrays are positioned on an exterior circumference of the polygon.

P19. The apparatus as described in any one of claims P16-P17, wherein the field controlled magnetic arrays are positioned on an interior circumference of the polygon.

P20. The apparatus as described in any one of claims P1-P19, wherein at least one of the small magnetic segments is rounded.

P21. The apparatus as described in any one of claims P1-P20, wherein at least one of the small magnetic segments is rectangular.

P22. A system for forming a compression anastomosis, the system comprising a plurality of small magnetic segments; and a support structure having a receptable configured to receive and secure the plurality of small magnetic segments in any of a plurality of individually-selected magnetic orientations to form a field controlled magnetic array (FCMA).

P23. The system as described in claim P22, wherein the small magnetic segments are individually oriented with a north magnetic pole at orientations of 0°, 45°, 90°, 135°, 180°, 225°, 270°, and 315° with respect to a plane in the FCMA.

P24. The apparatus as described in any one of claims P22-P23, wherein the receptacle is configured to allow each small magnetic segment to be individually oriented within the FCMA with the north magnetic pole at an orientation of 0°, 45°, 90°, 135°, 180°, 270°, or 315° with respect to a second plane in the FCMA.

P25. The apparatus as described in any one of claims P22-P24, wherein two or more of the plurality of small magnetic segments are different heights.

P26. The apparatus as described in any one of claims P22-P25, wherein two or more of the plurality of small magnetic segments are different widths.

P27. The apparatus as described in any one of claims P22-P26, wherein two or more of the plurality of small magnetic segments have different magnetic strengths.

P28. The apparatus as described in any one of claims P22-P27, wherein two or more of the plurality of small magnetic segments have different shapes.

P29. A system for forming a compression anastomosis, the system comprising two field controlled magnetic arrays (FCMAs), wherein each FCMA is configured to secure a plurality of small magnetic segments (SMSs), wherein the SMSs are different heights and arranged in an alternating short/tall/short/tall configuration so as to allow the FCMAs to interlock.

P30. A system for forming a compression anastomosis, the system comprising an exoskeleton configured to secure a field controlled magnetic array (FCMA), wherein each FCMA is configured to secure a plurality of small magnetic segments (SMSs).

P31. The system as described in claim P30, wherein the SMSs are individually oriented within the FCMA.

P32. The system as described in any one of claims P30-P31, further comprising a securement device configured to secure the field controlled magnetic array within the exoskeleton.

P33. The apparatus as described in claim P32, wherein the securement device is a screw.

P34. The apparatus as described in claim P32, wherein the securement device is a band.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A magnetic compression anastomosis device comprising:
   a plurality of interconnected support structures configured to form an magnetic compression anastomosis device having an annular or polygon deployed configuration, wherein each support structure of the plurality of interconnected support structures includes a receptacle configured to receive and secure a plurality of small magnetic segments each having a north magnetic pole individually orientable within the receptacle to form a field controlled magnetic array (FCMA), the magnetic compression anastomosis device including a plurality of field programmable magnetic arrays each having a configurable surface field strength.

2. The device of claim 1, wherein the small magnetic segments are individually orientable substantially in a plane of the receptacle.

3. The device of claim 1, wherein the small magnetic segments are individually orientable substantially perpendicular to a plane of the receptacle.

4. The device of claim 1, wherein the receptacle is configured to allow each small magnetic segment to be individually oriented within the FCMA with the north magnetic pole at an orientation of 0°, 90°, 180°, or 270°, with respect to a mating surface of the FCMA.

5. The device of claim 1, wherein the receptacle is configured to allow each small magnetic segment to be individually oriented within the FCMA with the north magnetic pole at an orientation of 0°, 45°, 90°, 135°, 180°, 225°, 270°, or 315° with respect to a mating surface of the FCMA.

6. The device of claim 1, wherein the receptacle is substantially rectangular.

7. The device of claim 1, further comprising:
   the plurality of small magnetic segments individually oriented within the receptacle.

8. The device of claim 7, wherein two or more of the plurality of small magnetic segments are different heights.

9. The device of claim 7, wherein two or more of the plurality of small magnetic segments are different widths.

10. The device of claim 7, wherein two or more of the plurality of small magnetic segments have different magnetic strengths.

11. The device of claim 7, wherein two or more of the plurality of small magnetic segments have different shapes.

12. The device of claim 7, wherein at least one of the small magnetic segments is rounded.

13. The device of claim 7, wherein at least one of the small magnetic segments is rectangular.

14. The device of claim 7, further comprising:
   means for securing the plurality of individually oriented small magnetic segments within the receptacle.

15. The device of claim 1, wherein the plurality of interconnected support structures are configured to transition from a delivery configuration to the annular or polygon deployed configuration.

16. The device of claim 15, wherein the delivery configuration is substantially linear.

17. The device of claim 16, wherein the plurality of interconnected support structures are configured to self-assemble into the annular or polygon deployed configuration.

18. The device of claim 15, further comprising:
   an exoskeleton interconnecting the plurality of support structures and biasing the plurality of support structures toward the deployed configuration.

19. The device of claim 1, wherein at least one field controlled magnetic array of the plurality of field controlled magnetic arrays is positioned on an exterior circumference of the annular or polygon deployed configuration.

20. The device of claim 1, wherein at least one field controlled magnetic array of the plurality of field controlled magnetic arrays is positioned on an interior circumference of the annular or polygon deployed configuration.

* * * * *